US011421239B2

(12) United States Patent
Mattozzi et al.

(10) Patent No.: US 11,421,239 B2
(45) Date of Patent: Aug. 23, 2022

(54) PLASMID ADDICTION SYSTEM TO DRIVE DESIRED GENE EXPRESSION

(71) Applicant: Conagen, Inc., Bedford, MA (US)

(72) Inventors: Matthew de la Pena Mattozzi, Boston, MA (US); Daniel Kim, Carlisle, MA (US); Sonya Clarkson, Beverley, MA (US)

(73) Assignee: Conagen Inc., Bedford, MA (US)

( * ) Notice: Subject to any disclaimer, the term of this patent is extended or adjusted under 35 U.S.C. 154(b) by 747 days.

(21) Appl. No.: 16/036,261

(22) Filed: Jul. 16, 2018

(65) Prior Publication Data

US 2019/0024097 A1    Jan. 24, 2019

Related U.S. Application Data

(60) Provisional application No. 62/535,596, filed on Jul. 21, 2017, provisional application No. 62/697,531, filed on Jul. 13, 2018.

(51) Int. Cl.
*C12N 1/21* (2006.01)
*C12N 15/70* (2006.01)
*C12P 21/00* (2006.01)
*C12P 21/02* (2006.01)

(52) U.S. Cl.
CPC .............. *C12N 15/70* (2013.01); *C12P 21/00* (2013.01); *C12P 21/02* (2013.01); *C12N 2840/002* (2013.01)

(58) Field of Classification Search
None
See application file for complete search history.

(56) References Cited

U.S. PATENT DOCUMENTS

2017/0306337 A1* 10/2017 Tabita .................... C12N 15/64

OTHER PUBLICATIONS

Baba, T., et al., Construction of Escherichia coli K-12 in-frame, single-gene knockout mutants: the Keio collection, Mol. Syst. Biol. 2, 2006.
Balbas, P., et al; Understanding the Art of Producing Protein and Nonprotein Molecules in Escherichia coli; Molecular Biotechnology (2001) vol. 19, (3) pp. 251-267.
Balbas, P. et al; Plasmid vector pBR322 and its special purpose derivatives—a review; Gene (1986) vol. 50 pp. 3-40.
Beck, C. F. et al; A Multifunctional Gene (tetR) Controls Tn10-encoded Tetracycline Resistance; Journal of Bacteriology (1982) vol. 150 No. 2 pp. 633-642.
Brantl, S., Antisense RNAs in plasmids: control of replication and maintenance, Academic Press, Plasmid 48 (2002) pp. 165-173.
Brosius, J., et al; Construction and Fine Mapping of Recombinant Plasmids Containing the rrnB Ribosomal RNA Operon of E. coli; Plasmid (1981) vol. 6 No 1 pp. 112-118.
Chang, A. C. Y., et al., Construction and Characterization of Amplifiable Multicopy DNA Cloning Vehicles Derived for the P15A Cryptic Miniplasmid; J. Bacteriology (1978) vol. 134 No. 3 pp. 1141-1156.
Choi Y. J., et al; Novel, Versatile, and Tightly Regulated Expression System for Escherichia coli Strains. Applied and Environmental Microbiology (2010) vol. 76,No. 15, pp. 5058-5066.
Cranenburgh, R.M. et al., Escherichia coli strains that allow antibiotic-free plasmid selection and maintenance by repressor titration, Nucleic Acids Research, 2001 vol 29, No. 5, 1-6.
Datsenko, K.A., and Wanner, B.L., One-step inactivation of chromosomal genes in Escherichia coli K-12 using PCR products, Proc. Natl. Acad. Sci. U. S. A. 97, 6640-5 (2000).
Deboy, R.T., et al; Target Site Selection by Tn7: attTn7 Transcription and Target Activity; Journal of Bacteriology (2000) vol. 182 No. 11 pp. 3310-3313.
Del Solar, Gloria et al.,Replication and Control of Circular Bacterial Plasmids, Microbiology and Molecular Biology Reviews (1998) vol. 62, No. 2, pp. 434-464.
Eguchi, Yutaka., et al., Complexes Formed by Complementary RNA Stem-loops. Their Formation, Structure and Interaction with ColE1 Rom Protein, Journal Molecular Biology (1991) vol. 220 pp. 831-842.
Fu X., et al., Development of a Chromosome-Plasmid Balanced Lethal System of Lactobacillus Acidophilus with thyA Gene as Selective Marker, Microbiol. Immunol., 44(7) p. 551-56 (2000).
Funke, M. et al., The baffled microtiter plate: Increased oxygen transfer and improved online monitoring in small scale fermentations, Biotechnol. Bioeng. (2009) 103, 1118-28.
Furste, J.P., et al., Molecular Cloning of the Plasmid RP4 Primase Region in a Multi-Host-Range tacP Expression Vector, Gene (1986) vol. 48 pp. 119-131.
Gerdes K., et al., Mechanism of post-segregational killing by the hok/sok system of plasmid R1: sok antisense RNA regulates formation of a hok mRNA species correlated with killing of plasmid-free cells, Mol. Microbiol. (1990) 4 (11): 1807-18.
Gerdes, S.Y., et al., Experimental Determination and System Level Analysis of Essential Genes in Escherichia coli MG1655, Journal of Bacteriology (2003) vol. 185 No. 19 pp. 5673-5684.
Haegg, P., et al., A Host/Plasmid System that is not Dependent on Antibiotics and Antibiotic Genes for Stable Plasmid Maintenance in Eschericia coli., Journal of Biotechnology (2004) vol. 111 pp. 17-30.
Helinski, D.R., et al; Replication Control and Other Stable Maintenance Mechanisms of Plasmids (1996) American Society for Microbiology Press, Washington, DC, pp. 2295-2324.
Hiszczynska-Sawicka, Elzbieta., et al., Effect of Integration Host Factor on RNA II Synthesis in Replication of Plasmid Containing orip15A, Plasmid (1998) vol. 40 pp. 150-157.

(Continued)

*Primary Examiner* — Celine X Qian
(74) *Attorney, Agent, or Firm* — Wolf, Greenfield & Sacks, P.C.; W. John Keyes

(57) ABSTRACT

The present invention relates to a Plasmid Addiction System for the stabilization of expression plasmids encoding proteins of interest. The invention uses a succinate cycle optimization to ensure the expression of plasmid(s) of interest. By ensuring that plasmids of interest contain genes necessary in the succinate cycle, the system ensures that the passage of the plasmid to daughters and therefore improves the efficiency of production and expression of genes and/or products of interest.

11 Claims, 16 Drawing Sheets

Specification includes a Sequence Listing.

(56) References Cited

OTHER PUBLICATIONS

Herring, Christopher D., et al., Conditional Lethal Amber Mutations in Essential *Escherichia coli* Genes, Journal of Bacteriology (2004) vol. 186, No. 9 pp. 2673-2681.

Jensen, L. Bogo., et al., A Substrate-Dependent Biological Containment System for Pseudonomas Putida Based on the *Escherichia coli* gef Gene, Applied and Environmental Microbiology (1993) vol. 59, No. 11 pp. 3713-3717.

Knudsen, Steen., et al., Development and Testing of Improved Suicide Functions for Biological Containment of Bacteria, Applied and Environmental Microbiology (1995) vol. 61, No. 3 pp. 985-991.

Kroll, J., et al., Plasmid Addiction Systems: Perspectives and Applications in Biotechnology, Microb. Biotechnol., 3(6) pp. 634-657 (2010).

Kues, U., et al., Replication of Plasmids in Gram-Negative Bacteria, Microbiological Reviews (1989) vol. 53, No. 4 pp. 491-516.

Mairhofer, Jurgen et al.; A novel antibotic free plasmid selection system: Advances in safe and efficient DNA therapy, Biotechnology Journal (2008) 3, pp. 83-89.

Mattozzi, M.D. et al., Expression of the sub-pathways of the Chloroflexus aurantiacus 3-hydroxypropionate carbon fixation bicycle in *E. coli*: Toward horizontal transfer of autotrophic growth, Metab. Eng. 16, 130-139. (2013).

Merlin, S., et al., Assessment of Quantitative Models for Plasmid ColE1 Copy Number Control, J. Mol. Biol. (1995) vol. 248 pp. 211-219.

Michel, Gerhard and Dietmar Schomberg; Metabolic Pathways. (2012) John Wiley and Sons, New York, Poster.

O'Kennedy, R.D., et al., Effects of Fermentation Strategy on the Characteristics of Plasmid DNA Production, Biotechnol. Appl. Biochem. (2003) vol. 37 pp. 83-90.

O'Kennedy, R.D., et al., Effects of Growth Medium Selection on Plasmid DNA Production and Initial Processing Steps, Journal of Biotechnology (2000) vol. 76 pp. 175-183.

Postle, K., et al; Nucleotide Sequence of the Repressor Gene of the TN10 Tetracycline Resistance Determinant; Nucleic Acids Research (1984) vol. 12, No. 12 pp. 4849-4863.

Pfaffenzeller, I., Using ColE1-derived RNA I for suppression of a bacterially encoded gene: implication for a novel plasmid addiction system, Biotech. J. (2006), pp. 1-7.

Rawlings, D.E.; Protein Toxin-Antitoxin, Bacterial Plasmid Addiction Systems and their evolution with Special reference to the pas System of pTF-FC2; FEMS Microbiology Letters (1999) vol. 176 pp. 269-277.

Reinikainen, P., et al; *Escherichia coli* Plasmid Production in Fermenter; Biotechnology Bioenginering (1988) vol. 33 pp. 386-393.

Ronchel, M. Carmen., et al; Characterization of Cell Lysis in Pseudomonas putida induced Upon Expression of Heterologous Killing Genes, Applied and Environmental Microbiology, (1998) vol. 64, No. 12 pp. 4904-4911.

Germán L. Rosano and Eduardo A. Ceccarelli, Recombinant protein expression in *Escherichia coli*: advances and challenges, Microbiol. (2014); 5:172.

Schumacher M.A., Bacterial plasmid partition machinery: a minimalist approach to survival, Curr Opin Struct Biol., Feb. 2012;22(1):72-9.

Tomizawa, Jun-Ichi., et al; Plasmid ColE1 Incompatibility Determined by Interaction of RNA I with Primer Transcript; Proc. Natl. Acad. Sci. USA (1981) vol. 78, No. 10 pp. 6096-6100.

Tomizawa, Jun-Ichi, Control of ColE1 Plasmid replication: The Process of Binding of RNA I to the Primer Transcript, Cell (1984) vol. 38 pp. 861-870.

Tomizawa, Jun-Ichi; Control of ColE1 Plasmid Replication: Binding of RNA I to RNA II and Inhibition of Primer Formation, Cell (1986) vol. 47 pp. 89-97.

Torres, B., et al., As Gene Containment Strategy Based on a Restriction-Modification System, Environmental Microbiology (2000) vol. 2, No. 5 pp. 555-563.

Vieira, J., et al; The pUC Plasmids, an M13mp7-Derived System for Insertion Mutagenesis and Sequencing with Synthetic Universal Primers; Gene (1982) vol. 19 pp. 259-268.

Williams, S.G., et al.. Repressor Titration: A Novel System for Selection and Stable Maintenance of Recombinant Plasmids, Nucleic Acids Research (1998) vol. 26, No. 9 pp. 2120-2124.

Yu., B.J., et al., sucAB and sucCD are mutually essential genes in *Escherichia coli*., FEMS Microbiol. Lett. (2005) 254, 245-50.

Yu, D., et al.; An Efficient Recombination System for Chromosome Engineering in *Escherichia coli*; PNAS (2000) vol. 97, No. 11 pp. 5978-5983.

* cited by examiner

PLASMID ADDICTION SYSTEM TO DRIVE DESIRED GENE EXPRESSION

CROSS-REFERENCE TO RELATED APPLICATIONS

This application claims priority to U.S. Provisional Patent Applications No. 62/697,531, filed Jul. 13, 2018, entitled PLASMID ADDICTION SYSTEM TO DRIVE DESIRED GENE EXPRESSION; and No. 62/535,596, filed Jul. 21, 2017, entitled PLASMID ADDICTION SYSTEM TO DRIVE DESIRED GENE EXPRESSION, the disclosures of both of which are hereby incorporated by reference in their entirety.

FIELD OF THE INVENTION

The field of the invention relates to methods and processes useful in maintaining extrachromosomal elements of interest in a microbial production strain using genes from the succinate pathway to ensure inclusion and expression of the elements in daughter cells. More specifically, it relates to the use of a plasmid addiction system that ensures that modified microbial cells will maintain plasmids carrying genes involved in producing desired expression products.

BACKGROUND OF THE INVENTION

The present invention is directed to a method of manipulating microbial cells in culture to maintain at least one extrachromosomal element of interest containing at least one gene of interest. Typically, this extrachromosomal element is a plasmid, though phages, prophages, phagemids, cosmids, bacterial artificial chromosomes (BACs) also contain extrachromosomal elements to contain transgenes of heterologous interest. Though naturally occurring in bacteria, not all wild type plasmids contain genetic information that is required to maintain the viability of the host cell in normal conditions. However, plasmids can contain genetic information that provides selective advantages to the host under specific environmental challenges such as antibiotic resistance or resistance to noxious compounds present in the environment. However, in those situations where adverse environmental conditions are not present, the presence of the plasmid is, in fact, a metabolic burden upon the cell (Nordstrom and Austin, 1989). In other words, the metabolic activity required to maintain plasmids exerts a small but real metabolic cost to the host cell relative to those cells not carrying the plasmid in question. This metabolic burden is why many daughter cells tend to 'lose' the plasmid of interest over time if they can continue to exist or reproduce without it. This process of loss or limited replication of the extrachromosomal element(s) also leads to diminished efficiency in those experiments that require the presence of a plasmid genetic component to produce a product of interest and therefore cultures with significant amounts of daughter cells that do not have the plasmid(s) of interest provide a reduced efficiency for the experiment being conducted. This is particularly acute in those fermentation experiments that rely upon economies of scale and consistent production of a molecule of interest to make their cost targets. Daughter cells deficient in the desired plasmids or extrachromosomal elements represent a media and energy sink in overall production and contribute to the economic benefits of fermentation costs.

In the biotechnology industry, plasmids and similar extrachromosomal elements have become very important tools in the genetic engineering of microbes and in the expression of proteins of interest and commercial synthetic biology. Such elements can be manipulated and designed to force the host cell to carry them forward or perish. (Balbas 2001; Baba 2006). In this sense, the cells become irreversibly 'addicted' to maintaining the extrachromosomal element in the cell despite the consequent metabolic burden (hence the term, Plasmid Addiction System or "PAS"). With such a system in hand the researcher can then focus on driving the host cell culture not just to maintain and express the PAS system genes, but to express all the genes contained on such an extrachromosomal element. According to the current invention, this can entail the expression of a number of genes and potential gene products of interest in microbial systems.

Plasmid Addiction Systems and Alternatives

Given the power of such techniques to drive the expression of proteins of interest, it is not surprising that a variety of approaches have been developed to ensure the stable maintenance of plasmids in cells (Nordstrom and Austin, 1989). This includes: (i) site-specific recombination systems functioning as plasmid maintenance systems for high-copy plasmid systems (Grindley et al., 2006); (ii) active partition systems (Funnell and Slavcev, 2004); and, as mentioned above, (iii) plasmid addiction systems (PAS), like the invention provided herein, that prevent the continuing survival/replication of cells not containing and expressing the genes of the plasmid of interest (Gerdes et al., 2005).

Site-Specific Recombination Control Systems

Site-specific recombination is a type of genetic recombination in which a DNA strand exchange takes place between segments possessing at least a certain degree of sequence homology. In this system, a site-specific recombinase(s) (SSRs) performs rearrangements of DNA segments by recognizing and binding to short DNA sequences (sites), at which they cleave the DNA backbone, exchange the two DNA helices involved and then rejoin the DNA strands. (Datsenko and Wanner, 2000). While in some site-specific recombination systems just a single recombinase enzyme and the corresponding recombination sites is enough to perform all these reactions, in other systems a number of accessory proteins and/or accessory sites are also needed—each addition adding to the complexity and thereby decreasing both the reliability and versatility of this system. (Baba et al., 2006). In addition, the constitutive expression of the required recombinases can also lead to undesired genotypic changes and the use of the system in terms of its initial development can be challenging in terms of the transfer of the recombinases genes to progeny.

Plasmid Instability

As mentioned above, microbes tend towards eliminating plasmids or limiting the reproduction of plasmids in cells due to the ongoing metabolic burden of both maintaining the plasmid itself and of expressing the gene(s) contained therein. (Rosano et al., 2014). Additionally, cells may not favor plasmid replication and expression when the plasmids in question may contain genes, that when expressed, produce toxic products in the cell or in its immediate environment of the cell. Of course, the interest to those utilizing such microbial systems is the maintenance of the engineered genetic changes and consequent expression of the inserted genes. In this sense, stable inheritance of the plasmid and host generally requires that: (1) the plasmid must replicate once each generation; (2) copy number deviations must be rapidly corrected before cell division; and, (3) upon cell division, the products of plasmid replication must be distributed to both daughter cells in a reliable and consistent manner. (Balbas et al., 1986).

In general, the stable maintenance of low-copy-number plasmids in bacteria is actively driven by partition mechanisms that are responsible for the positioning of plasmids inside the cell prior to replication. Various such partition systems are ubiquitous in the microbial world and are encoded by many bacterial chromosomes as well as plasmids. These systems, although different in sequence and mechanism, typically consist of two proteins and a DNA partition site or prokaryotic centromere on the plasmid in question. One protein binds to the centromere to form a partition complex, and the other protein uses the energy of nucleotide binding and hydrolysis to transport the plasmid as needed. For plasmids, this minimal cassette is sufficient to conduct appropriate segregation. In an optimal setting the strain selected to carry a plasmid of interest will have a partition system that provides or consistent and reliable plasmid reproduction. (Balbas et al., 1986; Rawlings 1999).

Engineered Plasmid Stabilization Systems

There are systems engineered to stably maintain the plasmids of interest. One particularly common system is the use of antibiotics as selection tools. In such systems, the antibiotic resistance gene in the plasmid of interest protects the cell carrying it, at the same time it effectively "forces" the cell to maintain it when the bacterial cell is grown in a media-enriched with the corresponding antibiotic. (Cranenburgh, R. M. et al., 2001). However, this method is subject to a number of difficulties and concerns. The antibiotic resistance approach is expensive, requiring the use of costly antibiotics and some may find it objectionable as a culture method in when used in industrial production methods could be a way that accelerates and/or spreads the development of bacterial antibiotic resistance that could affect human and/or animal populations negatively. Moreover, in large-scale production applications, the use of antibiotics may impose other limitations. With respect to commercial bioreactors, antibiotic resistance mechanisms can degrade the antibiotic itself and permit a substantial population of plasmid-less cells to persist in the culture. Such plasmid-less cells are unproductive and decrease the overall output of the bioreactor, thereby increasing cost and decreasing efficiency. (Balbas 2001; Baba 2006).

Segregational Plasmid Maintenance Functions

Stable lower copy number plasmids typically employ a partitioning function that actively distributes plasmid copies between daughter cells. Examples of partitioning mechanisms include: pSC101, F factor, P1 prophage, and IncFII drug resistance plasmids. Such functions act to physically segregate plasmids during replication. In terms of functionality many small plasmids rely on a high copy number, distributed throughout the cell, to ensure at least one copy is maintained by each daughter cell upon division. Many large, low-copy number plasmids, on the other hand, encode active segregation systems to avoid stochastic loss. A variety of partitioning systems exist, but most rely on three components: a centromeric DNA region, a cytomotive filament, and an adaptor protein linking the two. In type II segregation bacterial actin-like protein (ALP) filaments drive plasmid separation. (Balbas et al., 2001; Balbas 1986; Schumacher 2014).

Post-Segregational Killing (PSK) Functions

Naturally occurring PSK plasmid maintenance functions typically employ a two-component toxin-antitoxin system and generally operate as follows: The plasmid encodes both a toxin and an antitoxin. The antitoxins are less stable than the toxins, which tend to be quite stable. In a plasmid-less daughter cell, the toxins and anti-toxins are no longer being produced; however, the less stable antitoxins quickly degrade, thereby freeing the toxin to kill the cells in the surrounding area without the antitoxins being present. (Gerdes 1990).

The toxins are generally small proteins and the antitoxins are either small proteins or antisense RNAs which bind to the toxin-encoding mRNAs preventing their synthesis (EX: antisense systems such as hok-sok). In antisense maintenance systems, the antitoxins are antisense RNAs that inhibit translation of toxin-encoding mRNAs. Like the antitoxin peptides, the antisense RNAs are less stable than the toxin-encoding mRNA. Loss of the plasmid permits existing antitoxins to degrade, thereby permitting synthesis of the toxin which kills the host cell. A limitation of the hok-sok system is that a significant number of plasmid-less cells can arise when the hok-sok system is inactivated by mutations within the Hok open reading frame. (Gerdes 1990).

Balanced Lethal Systems

In a balanced-lethal system (a PSK function), a chromosomal gene encoding an essential structural protein or enzyme is deleted from the bacterial chromosome or is mutated such that the gene can no longer operate (Fu., 2000). The removed or damaged gene is then replaced by a plasmid comprising a fully operating gene. Loss of the plasmid results in an insufficiency of the essential protein and the death of the plasmid-less cell. Balanced-lethal systems based on catalytic enzyme production are subject to a number of deficiencies. In particular, since complementation of the chromosomal gene deletion requires only a single gene copy, it is inherently difficult to maintain more than a few copies of an expression plasmid. The plasmid less host strain must be grown on special media to chemically complement the existing metabolic deficiency. (Fu 2000).

Commercial Efforts & Need

Biotechnical production processes often operate with plasmid-based expression systems in well-established prokaryotic and eukaryotic hosts such as *Escherichia coli* or *Saccharomyces cerevisiae*, respectively. Genetically engineered organisms produce important chemicals, biopolymers, biofuels and high-value proteins like insulin. In those bioprocesses plasmids in recombinant hosts have an essential impact on productivity. (Kroll J., 2010). Plasmid-free cells lead to losses in the entire product recovery and decrease the profitability of the whole process (Table 1). Often, the use of antibiotics in industrial fermentations is not an available or desirable option to maintain plasmid stability. Especially in pharmaceutical or GMP-based fermentation processes, deployed antibiotics must be inactivated and removed. As stated above, they are also costly. Several plasmid addiction systems (PAS) have been described in the literature and referenced above. The current PAS provides a new method that is antibiotic free, remains absolutely necessary for cellular replication and homestasis and allows multiple gene carrying plasmids, or the like, to be maintained efficiently in culture.

Given the above, there remains a need in the art for a new PAS that is reliant on a balanced lethal system, not requiring antibiotics is useful to industry and can drive the production of high volumes of compounds of interest in a commercially efficient way.

SUMMARY OF THE INVENTION

The present invention encompasses improved methods of devising a plasmid addiction system that can enhance the production of proteins of interest and do so at commercial scale.

According to the current invention, a biosynthetic method is provided for the production of one or more proteins of interest in a microbial system.

Recombinant plasmids carrying the gene of interest are obtained by cultivation of bacteria. For selecting bacterial transformants, and in order to ensure the maintenance of the plasmids in the bacterial host cell, an antibiotic resistance gene is traditionally included in the plasmid backbone. Selection for plasmids is achieved by growing the cells in a medium containing the respective antibiotic, in which only plasmid bearing cells are able to grow, often with a marker gene included. A number of plasmid addiction systems (PAS) already exist, mainly as toxin-antitoxin systems that limit the plasmids to single copy or aimed for use in open environments like bioremediation contexts. However, there are few examples of nutrition-based plasmid addiction systems, or ones exhibiting long-term stability in an industrial setting. The current invention provides both.

According to the current invention a plasmid addiction system utilizing the succinate pathway as the conditional mutant where key chromosomal genes have been removed and placed in the plasmids to be expressed and maintained in daughter cells. Such a system could be used for the production of specific amylases, pathway genes, lipases, proteases, vitamins or antibiotics, and according to the current invention could be forced to maintain up to four different plasmids.

According to the preferred embodiments of the invention, the applicants provide a plasmid addiction system based on the synthetic lethal deletion of either the double mutant sucAD or the quadruple mutant sucABCD, wherein the native mutations are complemented on one or more plasmids. The plasmid(s) of interest allows for near wild-type growth without supplementation of DAP or any other intermediate and is retained for many generations in the absence of selective markers. It is useful in a laboratory context, as transformants can be grown LB plates without any additional supplementation; the parent strains cannot grow without supplementation with DAP. It is useful in an industrial context wherein neither antibiotics nor their requisite selection marker genes are wanted or desired. Given the inclusion of up to four required genes this means that four plasmids of different compositions can be retained in a fermentation of interest and at low cost. That is, a single plasmid can be maintained with a single gene of interest or up to four different plasmid types, each with one of the four required genes, carrying other genes of interest can be provided in the current system efficiently and with low cost.

BRIEF DESCRIPTION OF THE DRAWINGS

FIG. 2B provides a schematic of the genomic context of *E. coli* BW25113 ΔsucAD; and FIG. 2C provides a schematic of the genomic context of *E. coli* BW25113 ΔsucABCD.

DETAILED DESCRIPTION OF THE INVENTION

Figure 1A:
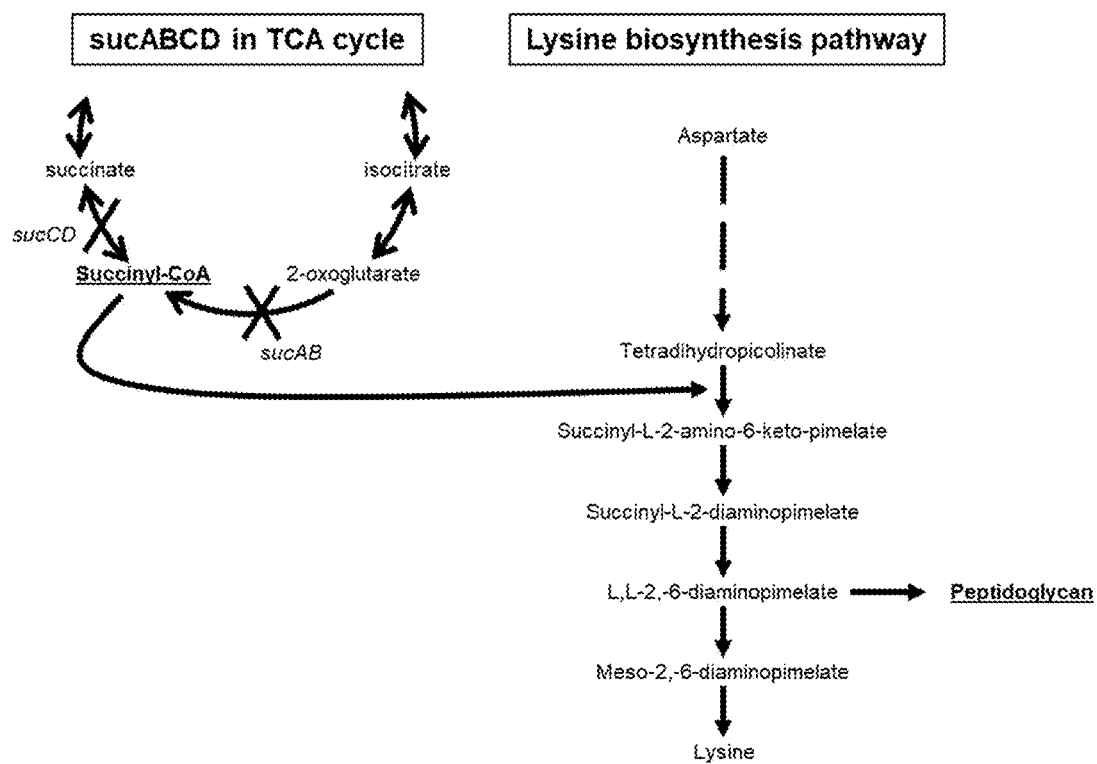
FIGS. 1A-1B. Show succinate and succinyl-CoA in context of central *E. coli* metabolism and cell wall biosynthesis (FIGS. 1A and 1B).

The following abbreviations have designated meanings in the specification:

Explanation of Terms:

Cellular system is any cells that provide for the expression of ectopic proteins. It included bacteria, yeast, plant cells and animal cells. It includes both prokaryotic and eukaryotic cells. It also includes the in vitro expression of proteins based on cellular components, such as ribosomes.

Growing the Cellular System. Growing includes providing an appropriate medium that would allow cells to multiply and divide given the changes to the succinate pathway. It also includes providing resources so that cells or cellular components can translate and make recombinant proteins. According to the current invention the cells grow on LB media. Such cells do not unless they are supplied with 120 µM DAP.

Protein Expression. Protein production can occur after requisite gene expression. It consists of the stages after DNA has been transcribed to messenger RNA (mRNA). The mRNA is then translated into polypeptide chains, which are ultimately folded into proteins. DNA is present in the cells through transfection—a process of deliberately introducing nucleic acids into cells. The term is often used for non-viral methods in eukaryotic cells. It may also refer to other methods and cell types, although other terms are preferred: "transformation" is more often used to describe non-viral DNA transfer in bacteria, non-animal eukaryotic cells, including plant cells. In animal cells, transfection is the preferred term as transformation is also used to refer to progression to a cancerous state (carcinogenesis) in these cells. Transduction is often used to describe virus-mediated DNA transfer. Transformation, transduction, and viral infection are included under the definition of transfection for this application.

Acronyms:

TCA—Tricarboxylic Acid

DAP—Diaminopimelic Acid

PAS—Plasmid addiction system

TB—Terrific Broth

LB—Luria Broth

Y(E)PD—Yeast Extract Peptone Dextrose (medium)

sucA—*E. coli* gene encoding the E1 component of the 2-oxoglutarate dehydrogenase enzyme sucB—*E. coli* gene encoding the E2 component of the 2-oxoglutarate dehydrogenase enzyme sucC—*E. coli* gene encoding the β subunit of the succinyl-CoA synthetase enzyme sucD—*E. coli* gene encoding the α subunit of the succinyl-CoA synthetase enzyme Alternative Marker Genes If marker genes are required for one or more genes of the current invention examples include: genes encoding restriction nucleases (e.g. CviAII, a restriction endonuclease originating from *Chlorella* virus PBCV-1; Zhang et al., 1992), EcoRI (Tones et al., 2000), genes encoding toxins that interact with proteins, e.g. streptavidin or stv13 (a truncated, easy soluble streptavidin variant), as described by Szafransky et al., 1997; Kaplan et al., 1999; Sano et al., 1995, which act by deprivation of biotin, an essential protein in cell growth); genes encoding proteins that damage membranes (the E gene protein of φX174 (Ronchel et al., 1998; Haidinger et al., 2002), gef (Jensen et al., 1993; Klemm et al., 1995), relF (Knudsen et al., 1995); genes that encode other bacterial toxins, e.g. the ccdb gene (Bernard and Couturier, 1992) that encodes a potent cell killing protein from the F-plasmid trapping the DNA gyrase or sacB from *Bacillus subtilis* (Gay et al., 1983); or genes that encode eukaryotic toxins that are toxic to the bacterial host (e.g. FUS; Crozat et al., 1993). When using toxic genes, it is essential that their expression can be modulated by an inducible promoter. This promoter must not be active without an inductor, but provide expression upon induction, sufficient to inhibit cell growth.

In certain embodiments, the marker gene is selected from genes encoding restriction nucleases, streptavidin or genes that have an indirect toxic effect, e.g. sacB, as described above.

A repressor is a protein that binds to an operator located within the promoter of an operon, thereby down-regulation transcription of the gene(s) located within said operon. Examples for repressors suitable in the present invention are the tetracycline repressor (tet) protein TetR, which regulates transcription of a family of tetracycline resistance determinants in Gram-negative bacteria and binds to tetracycline (Williams, et al., 1998; Beck, et al., 1982; Postle et al., 1984), the tryptophan repressor (trp), which binds to the operator of the trp operon, which contains the tryptophan biosynthesis gene (Yanofski et al., 1987).

Examples for inducible promoters are promoters, where transcription starts upon addition of a substance, thus being regulatable by the environment, e.g. the lac promoter, which is inducible by IPTG (Jacob and Monod, 1961), the arabinose-promoter (pBAD), inducible by arabinose (Guzman et al., 1995), copper-inducible promoters (Rouch and Brown, 1997), and cumate-inducible promoters (Choi et al 2010).

Alternately, constitutive promoters may be used, wherein transcription of the desired transgene is always driven on, regardless of the growth phase or environmental variables.

In an alternative embodiment, one could monitor the expression of a single gene of interest through the use of a marker gene as a reporter gene. Genes that could be used to provide this functionality include genes encoding GFP (Green Fluorescent Protein), hSOD (human superoxide dismutase), lacZ (beta-glucosidase), CAT (chloramphenicol acetyltransferase), nptII (neomycin phosphotransferase) or luciferase.

A reporter gene is useful in cultivation processes whenever information on the presence or absence of a plasmid in a host cell or on plasmid copy number is needed. Such information is particularly useful when fermentation processes are to be optimized with regard to control of plasmid copy number. A reporter gene may also serve as a surrogate of a toxic marker gene and may thus be used in experimental settings that aim at proving the functionality of constructs to be employed for the gene-regulating or silencing and to determine their effect on a toxic marker gene.

In certain embodiments of the invention, the marker gene may be an endogenous host gene, which may be any gene of interest that is intended to be regulated. In this case, the host cell is engineered such that the sequence encoding the sequence is operably associated with the relevant host gene.

While the disclosure is susceptible to various modifications and alternative forms, specific embodiments thereof are shown by way of example in the drawing and will herein be described in detail. It should be understood, however, that the drawings and detailed description presented herein are not intended to limit the disclosure to the particular embodiment disclosed, but on the contrary, the intention is to cover all modifications, equivalents, and alternatives falling within the spirit and scope of the present disclosure as defined by the appended claims.

Other features and advantages of this invention will become apparent in the following detailed description of preferred embodiments of this invention, taken with reference to the accompanying drawings.

The present invention relates to a system for an improved production method for proteins of interest in a microbial system that does not require markers, antibiotics and can produce proteins of interest at a high-level.

Bacterial Strains and Growth Conditions

BW25113 and the deletions for ΔsucA::KanR and ΔsucD::KanR were obtained from the *E. coli* Genetic Stock Center (CGSC). Cells were typically grown in Luria Broth (LB), but experiments were also performed in TB, YPD, YEPD, Nutrient Broth with corn steep liquor, and other rich media (Miller, 1972). Diaminopimelic acid (Sigma D1377) was used at 120 μM to aid in screening as the ΔsucAD double deletion is synthetic lethal (Mattozzi et al., 2013; Yu et al., 2006).

Construction of Strains with Chromosomal Mutations

P1vir transduction (Miller, 1972) was used to create kanamycin-resistant double knockout strains of *E. coli* BW25113 and screened with 120 μM DAP on LB kanamycin plates. These were screened for deletions of ΔsucA and ΔsucD via colony PCR. This KanR donor strain was also used to create double knockouts of *E. coli* strains BL21, BL21(DE3), MG1655, MG1655(DE3) ΔlacY, and W3110. Plasmid pCP20 was used to remove the kanamycin resistance markers using its FLP/FRT-based recombinase (Baba et al., 2006; Datsenko and Wanner, 2000). Since sucA and sucD are separated by only 6 kb, Kan sensitive cells exhibiting the quadruple deletion ΔsucABCD were usually isolated after the pCP20 FLP recombinase step (Datsenko and Wanner, 2000).

Construction of Recombinant Plasmids

Codon-optimized sequences encoding sucA, sucB, sucC, and sucD were synthesized (Quintara Bioworks, Emeryville Calif.). CIDAR *E. coli* Modular cloning (Iverson et al., 2016), was used to generate versions of sucABCD natural operon and the sucAD synthetic operon. Both versions were based on the *E. coli* MG1655 native sequence, but with illegal BsaI and BpiI sites replaced in-frame so as not to affect protein sequences. Additional codon optimization was performed to minimize recombination effects. Operons sucABCD and sucAD were identical except that the sequence between the start codon of sucB and the stop codon of sucC were deleted. (Yu et al., 2005).

According to the current invention, plasmids were transformed into ΔsucAD and ΔsucABCD strains via electroporation and selected on LB plates without any additional supplementation; the parent strains cannot grow without supplementation with DAP. Clones were confirmed by sequence.

Cultivation of Plasmid-Addicted Strains

Plasmid-bearing *E. coli* strains were grown in LB without additional supplementation in 24-well plates and in a Bio-Lector flower plates (Funke et al., 2009).

The present invention can be widely used in state-of-the-art fermentations, both for plasmid DNA production and for producing recombinant proteins.

Several approaches for fermentation of pDNA have been described that are useful for applying the present invention. The methods for plasmid DNA production differ with regard to the level of control imposed upon the cells and the numerous factors that influence fermentation.

To obtain higher quantities of plasmids, the cells can be cultivated in controlled fermenters in so-called "batch fermentations", in which all nutrients are provided at the beginning and in which no nutrients are added during cultivation. (Reinikainen, P., et al; 1988). Cultivations of this type may be carried out with culture media containing so called "complex components" as carbon and nitrogen sources, as described e.g. by O'Kennedy et al., 2003, and Lahijani et al., 1996, and in WO 96/40905, U.S. Pat. No. 5,487,986 and WO 02/064752. Alternatively, synthetic media may be used for pDNA production, e.g. defined culture media that are specifically designed for pDNA production (Wang et al., 2001; WO 02/064752).

The present invention may also be used in fed batch fermentations of *E. coli*, in which one or more nutrients are supplied to the culture by feeding, typically by using a feed-back control algorithm by feeding nutrients in order to control a process parameter at a defined set point. Feed-back control is hence directly related to cell activities throughout fermentation. Control parameters which may be used for feed-back control of fermentations include pH value, on line measured cell density or dissolved oxygen tension (DOT). A feed-back algorithm for controlling the dissolved oxygen tension at a defined set point by the feeding rate was described in WO 99/61633.

Alternatively, the invention may be applied in a process for producing plasmid DNA, in which *E. coli* cells are first grown in a pre-culture and subsequently fermented in a main culture, the main culture being a fed-batch process comprising a batch phase and a feeding phase. The culture media of the batch phase and the culture medium added during the feeding phase are chemically defined, and the culture medium of the feeding phase contains a growth-limiting substrate and is added at a feeding rate that follows a pre-defined exponential function, thereby controlling the specific growth rate at a pre-defined value.

When the marker gene is under the control of an inducible promoter, the inducer may be added to the batch at the beginning and/or pulse-wise (both in a batch and in fed-batch cultivations). During the feed phase, the inducer may be added pulse-wise or continuously.

At the end of the fermentation process, the cells are harvested and the plasmid DNA is isolated and purified according to processes known in the art, e.g. by methods based on anion exchange and gel permeation chromatography, as described in U.S. Pat. No. 5,981,735 or by using two chromatographic steps, i.e. an anion exchange chromatography as the first step and reversed phase chromatography as the second step, as described in U.S. Pat. No. 6,197,553. Another suitable method for manufacturing plasmid DNA is described in WO 03/051483, which uses two different chromatographic steps, combined with a monolithic support.

In addition to applying the invention for plasmid production, e.g. for production of plasmids for gene therapy applications, it is also useful for recombinant protein production. (Rawlings 1999).

With regard to recombinant protein production, in principle, any method may be used that has proven useful for expressing a gene of interest in *E. coli*, in particular from a ColE1 type plasmid (see, for review, e.g. Jonasson et al., 2002; Balbas, 2001). The protein may be obtained intracellularly (completely or partially soluble or as inclusion bodies) or by secretion (into the cell culture medium or the periplasmic space) from batch fermentations or, preferably, fed-batch cultivations, using complex, synthetic or semisynthetic media.

In plasmid DNA production, usually plasmid DNA for gene therapy applications, the gene of interest is not expressed in the bacterial host cell. In view of its application in mammals, preferably in humans, where it is to be ultimately expressed, the gene of interest is usually operably associated with a eukaryotic promoter. In contrast, for recombinant production of proteins in *E. coli*, the gene of interest is to be expressed in the host cell therefore under the control of a prokaryotic promoter.

For recombinant protein production, the two promoters, i.e. the promoter controlling the marker gene and the promoter controlling the gene of interest, may be different or the same, as long as no interference occurs that disturbs expression of either one.

Advantageously, since their activity is independent of each other concerning time-point and level of transcription, the promoters are differently regulated. Preferably, the promoter controlling the marker gene is active at the start of the fermentation process and produces moderate amounts of mRNA, while the promoter of the gene of interest is rather strong and activated at a chosen time-point during fermentation. If inducible promoters are used for both the gene of interest and the marker gene, they are usually chosen such that they are turned on by different inducers. Alternatively, the marker gene may be under an inducible promoter and the gene of interest under a constitutive promoter, or vice versa. This applies both for methods in which the marker gene construct is integrated in the bacterial host genome and in which the marker gene construct is contained in a plasmid or phage, as described above.

With regard to induction of the promoter in the various phases of fermentation, the principle described above for plasmid DNA production applies.

The invention has the great advantage that all replicated plasmids are devoid of antibiotic resistance genes and are therefore, in addition to gene therapy applications, suitable for all applications for which the absence of antibiotic resistance genes is required or desirable, e.g. for the generation of recombinant yeast strains that are intended for human and animal food production or for the generation of recombinant plants.

Expression and Maintenance During Fermentation

Maintenance of heterologous DNA presents a major challenge in industrial systems. A number of systems already exist, but there are drawbacks to each of them. Integrating genes into the genome can be slow, require extensive screening, and is limited to a single copy per cell. Larger DNA loops like cosmids and bacterial artificial chromosomes (BACs) can be difficult to isolate from chromosomal DNA or cell debris pellets, and again are limited by copy number. Phages can be difficult to keep contained to the cell types of interest. They could become lytic unexpectedly, causing drastic consequences on a factory-scale. Thus, the most common way to introduce and maintain heterologous DNA into *E. coli* and other bacterial cultures is via plasmid, wherein the gene(s) of interest are maintained on a small loop of DNA containing sequences comprising an origin of replication and, typically, an antibiotic resistance marker. This marker can be problematic: antibiotics in the media can be expensive and can contaminate final small-molecule products with similar chemical properties. As well, the genes encoding these markers pose a biosafety issue: the antibiotics used in fermentation are the same or similar to the ones used in clinical settings. Though laboratory containment is usually good, large-scale use of antibiotic resistance genes could encourage the spread of dangerous resistant bacteria like methicillin-resistant *Staphylococcus aureus* (MRSA).

The principle of the invention, i.e. the metabolic context of the succinyl-CoA synthetic lethal deletions is shown in FIG. 1.

In embodiments of the invention, the following components are useful:

Host Cells

Since their replication depends on the host machinery, many plasmids are plasmids with a narrow host range. Replication is often limited to *E. coli* and related bacteria such as *Salmonella* and *Klebsiella* (Kues and Stahl, 1989). However, according to the current invention a great variety of functional hosts are available including eukaryotic systems. Other suitable hosts include: cells of the genera *Corynebacterium, Bacillus, Pseudomonas, Vibrio, Bulkholderia*, and really any other bacterium that can stably maintain a heterologous plasmid and has a peptidoglycan cell wall.

Preferred genetic features of the host cell are mutations that improve plasmid stability and quality or recovery of intact recombinant protein. Examples of desirable genetic deletions are:

sucA—*E. coli* gene encoding the E1 component of the 2-oxoglutarate dehydrogenase enzyme
sucB—*E. coli* gene encoding the E2 component of the 2-oxoglutarate dehydrogenase enzyme
sucC—*E. coli* gene encoding the β subunit of the succinyl-CoA synthetase enzyme
sucD—*E. coli* gene encoding the α subunit of the succinyl-CoA synthetase enzyme.

Each of the genes in this operon encodes part of a heterodimeric enzyme within the TCA cycle. Since sucAB and sucCD are synthetic lethal (Yu et al 2006), either sucAB OR sucCD pair may be deleted and still allow cell growth; albeit with reduced growth rates due to the inability of the cells to use oxygen as a terminal electron acceptor. This can eventually cause cell death, a reduced growth rate, low maximum cell density, and inefficient usage of carbon source. Deletion of at least three of the genes within the sucABCD cluster (or two from opposite conjugate pairs, e.g. ΔsucAD) creates a cell that is auxotrophic for succinyl-CoA. Because succinyl-CoA itself is unstable and expensive to procure commercially, it was discovered that supplementation of DAP in the medium can allow the cells to grow. This is because the external DAP can be incorporated into the cell walls, negating the need for the succinyl-CoA cofactor (FIG. 1). The cells can still grow, but albeit with a growth defect due to their inability to fully utilize oxygen as a terminal electron acceptor.

Constructs for Engineering the Host Cells

The principle of a construct suitable for engineering the host cells is shown in FIG. 2: The host strains were generated via P1 transduction (above), and the plasmids were produced via Gibson assembly, cloning, Golden Gate and/or modular cloning.

Characteristics of Plasmids for the System

The plasmids are required to express the genes specifically deleted in the host strain. In this example, codon-optimized versions of *E. coli* sucAD and sucABCD are expressed on plasmids, complementing the deletions made to BW25113 ΔsucAD and ΔsucABCD respectively.

EXAMPLES

Two or four key genes expressing essential proteins for the tricarboxylic acid (TCA) cycle were deleted from the *E. coli* genome. Previously these genes have been shown to be synthetic lethal (Yu et al., 2006). These cells are thus auxotrophic for succinyl-CoA. The cells can make up the energetic needs of the TCA cycle simply through fermentative growth, but the lack of a complete TCA cycle causes inefficient growth, and accumulation of toxic fermentative byproducts ethanol and acetate because the cells are unable to effectively use oxygen as a terminal electron acceptor. This can eventually cause cell death, a reduced growth rate, low maximum cell density, and inefficient usage of carbon source. In addition to the TCA cycle, succinyl-CoA is also used as a cofactor in many metabolic pathways. Perhaps the most important is the lysine synthesis pathway, wherein succinyl-CoA is required as an essential cofactor for generating diaminopimelic acid (DAP). DAP is a key monomer in the murein or peptidoglycan cell wall and was thus required for growth.

Previously, we built a system taking advantage of this fact (Mattozzi et al., 2013), as a test of a carbon fixation system. However, the knockouts were only used as a proxy for cell metabolic processes from *Chloroflexus aurantiacus*, not the ability of the cells to retain the plasmid or drive the production of proteins of interest. Double mutant ΔsucAD cells containing a plasmid expressing a succinyl-CoA:(S)-malyl-CoA transferase operon reduced but did not entirely remove the need for DAP in the system.

Bacterial Strains and Growth Conditions

BW25113 and the deletions for ΔsucA::KanR and ΔsucD::KanR were obtained from the *E. coli* Genetic Stock Center (CGSC) at Yale University. Cells were typically grown in Luria Broth (LB), but experiments were also performed in TB, YPD, YEPD, Nutrient Broth with corn steep liquor, and other rich media (Miller, 1972). Diaminopimelic acid (Sigma D1377) was used at 120 µM to aid in screening as the ΔsucA(B) Δsuc(C)D double deletion is synthetic lethal (Mattozzi et al., 2013; Yu et al., 2006).

Construction of Strains with Chromosomal Mutations

P1vir transduction (Miller, 1972) was used to create kanamycin-resistant double knockout strains of *E. coli* BW25113 and screened with 120 µM DAP on LB kanamycin plates. These were screened for deletions of ΔsucA and ΔsucD via colony PCR. This KanR donor strain was also used to create double knockouts of *E. coli* strains BL21, BL21(DE3), BL21*(DE3), MG1655, MG1655(DE3) ΔlacY, C41, and W3110. Plasmid pCP20 was used to remove the kanamycin resistance markers using its FLP/FRT-based recombinase (Baba et al., 2006; Datsenko and Wanner, 2000). Since sucA and sucD are separated by only 6 kb, Kan sensitive cells exhibiting the quadruple deletion ΔsucABCD were usually isolated after the pCP20 FLP recombinase step (Datsenko and Wanner, 2000).

Construction of Recombinant Plasmids

CIDAR *E. coli* Modular cloning (Iverson et al., 2016), a Golden Gate based technology, was used to generate versions of sucABCD natural operon and the sucAD synthetic operon. Both versions were based on the *E. coli* MG1655 native sequence, but with illegal BsaI and BpiI sites replaced in-frame so as not to affect protein sequences. Operons sucABCD and sucAD were identical except that the sequence between the start codon of sucB and the stop codon of sucC were deleted. Plasmids were transformed into sucAD and sucABCD strains via electroporation and selected on LB plates without any additional supplementation; the parent strains cannot grow without supplementation with DAP. Clones were confirmed by sequence.

Plasmids were transformed into ΔsucAD and ΔsucABCD strains via electroporation and selected on LB plates without any additional supplementation; the parent strains cannot grow without supplementation with DAP. Clones were confirmed by sequence.

Figure 1B:
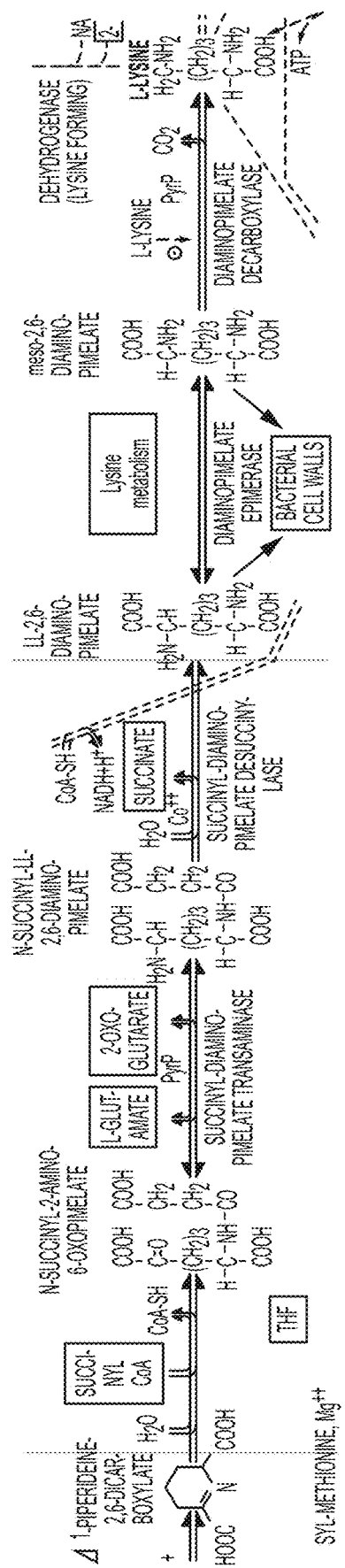
Figure 2A:
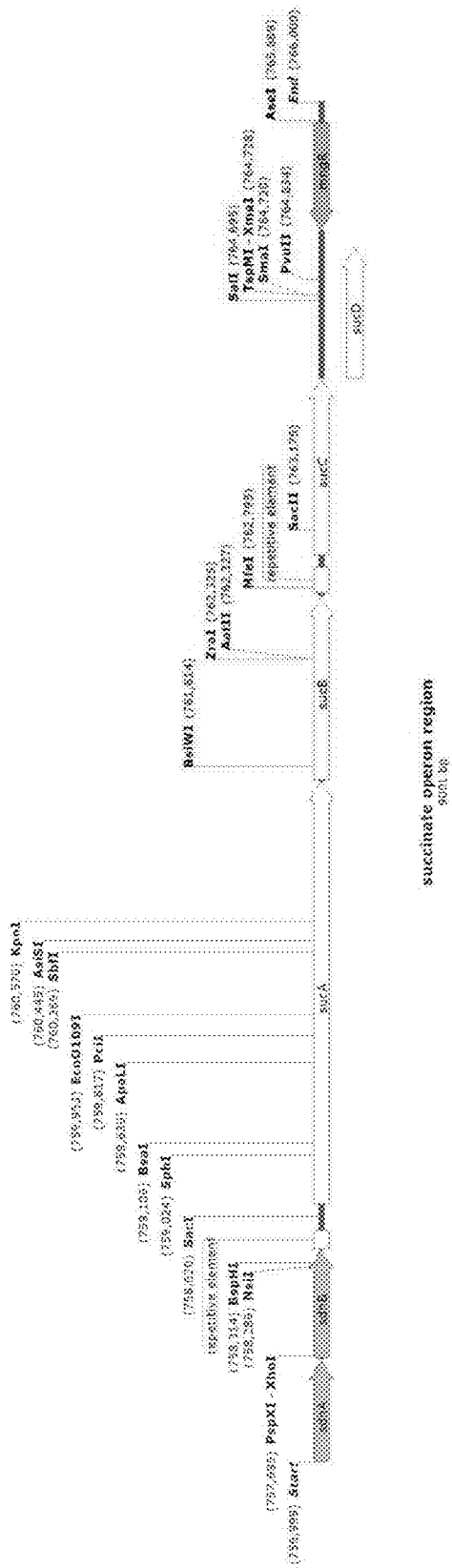
FIGS. 2A-2C. Show the multiple deletions sucAD (FIG. 2B) and sucABCD (FIG. 2C), which are synthetic lethal in the *E. coli* chromosome. The genomic context for the native *E. coli* strain of the invention—BW25113 and its succinyl-CoA operon is shown in FIG. 2A.

In FIG. 1A, we see the general metabolic context of succinyl-CoA, diaminopimelic acid, and peptidoglycan on murein cell walls. Succinyl-CoA generated by the gene products of sucAB and sucCD is used to produce lysine and its immediate biochemical precursor, diaminopimelate (DAP), critically required for *E. coli* cell wall (peptidoglycan or murein) biosynthesis. FIG. 1B provides the detailed metabolic context of the succinyl-CoA cofactor in diaminopimelate and lysine metabolism (Excerpted from Michel and Schomberg 2012). In FIG. 2A, the genomic context for the native *E. coli* strain of the invention—BW25113 and its succinyl-CoA operon are provided. According to the current invention the DNA sequence for this is (SEQ ID NO: 1).

Figure 2B:
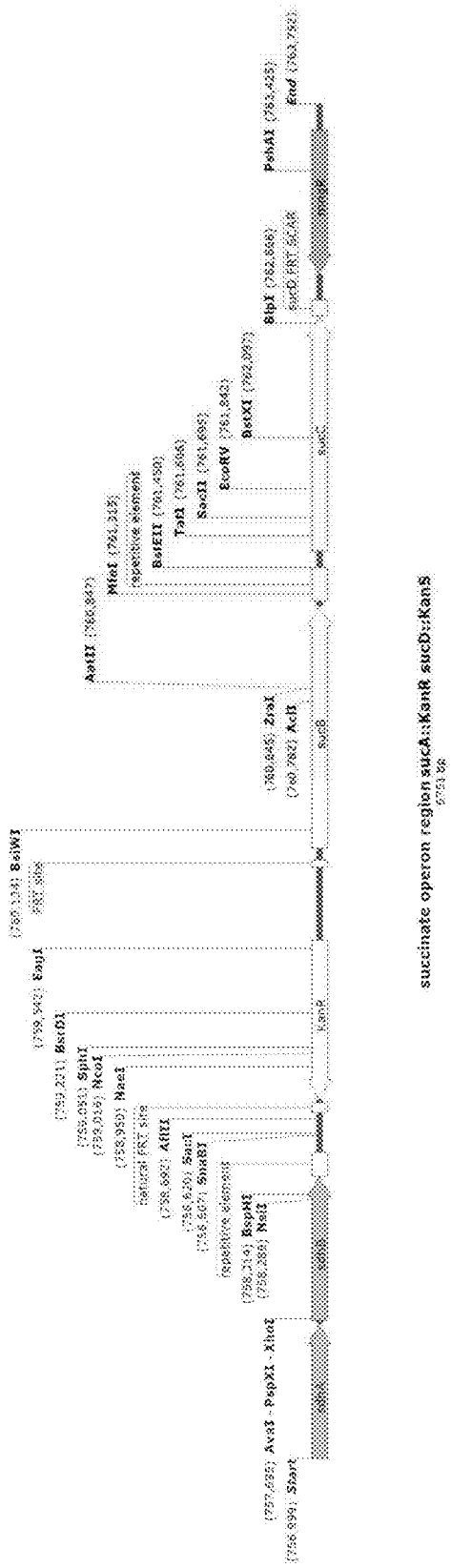
Figure 2C:
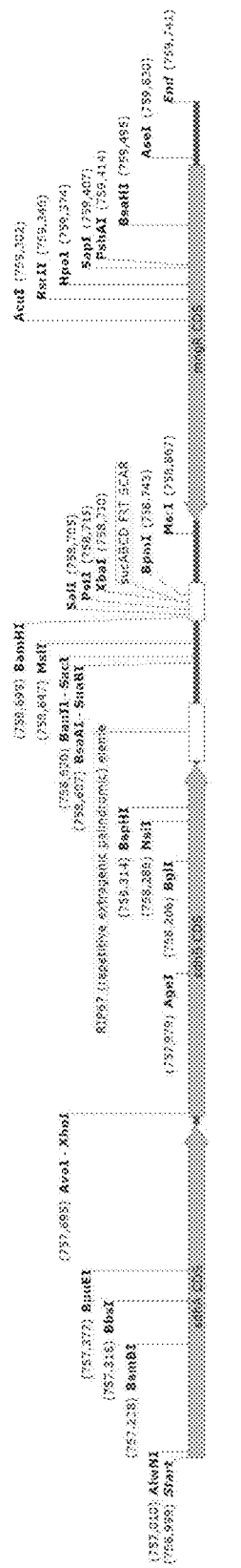

FIG. 2B provides a schematic of the genomic context of *E. coli* BW25113 ΔsucAD. This is the result of a P1 transduction in the *E. coli* genome wherein ΔsucA::kanR was used as a donor. Recipient strain was *E. coli* BW25113 ΔsucD::kanS, generated by removing kanamycin resistance via pCP20-mediated FRT excision (thereby providing SEQ ID NO: 2). FIG. 2C provides a schematic of the genomic context of *E. coli* BW25113 ΔsucABCD. The result is the removal of kanamycin resistance via pCP20-mediated FRT excision. Since sucA and sucD are within 6 kb, deletions of the entire sucABCD operon were isolated in the purification process (SEQ ID NO: 3).

Figure 3A:
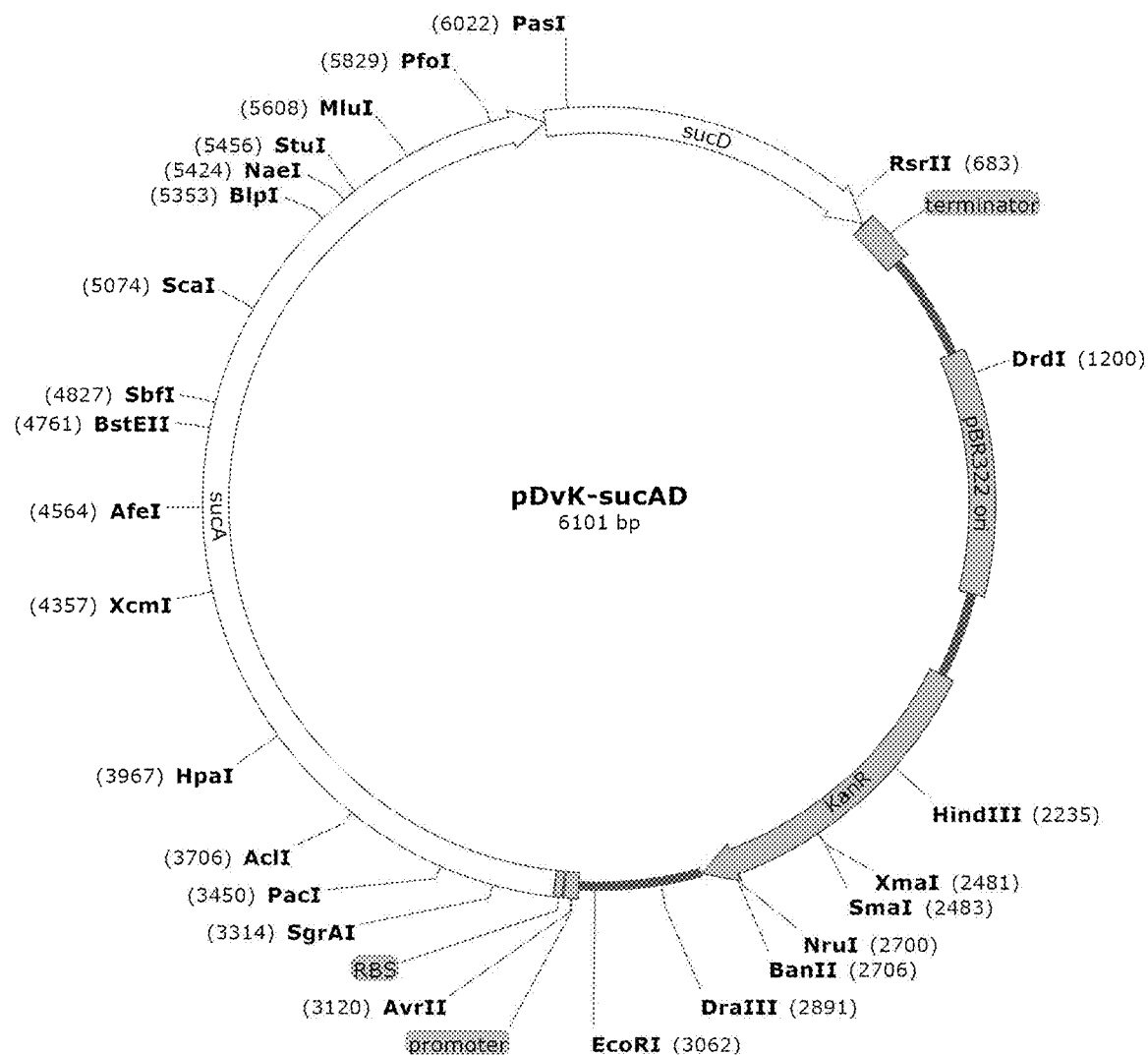
FIGS. 3A-3E. Show plasmid maps of pDvS and pDvQ plasmids, cloning vectors designed to express sucAB and sucABCD complements rather than antibiotic resistance markers. pDvK-sucAD (FIG. 3A); pDvK-sucABCD (FIG. 3B); pDvS-Kan-dropout (FIG. 3C); and pDvQ-Kan-dropout (FIG. 3D); pDvK-sucBC (FIG. 3E)
Figure 3B:
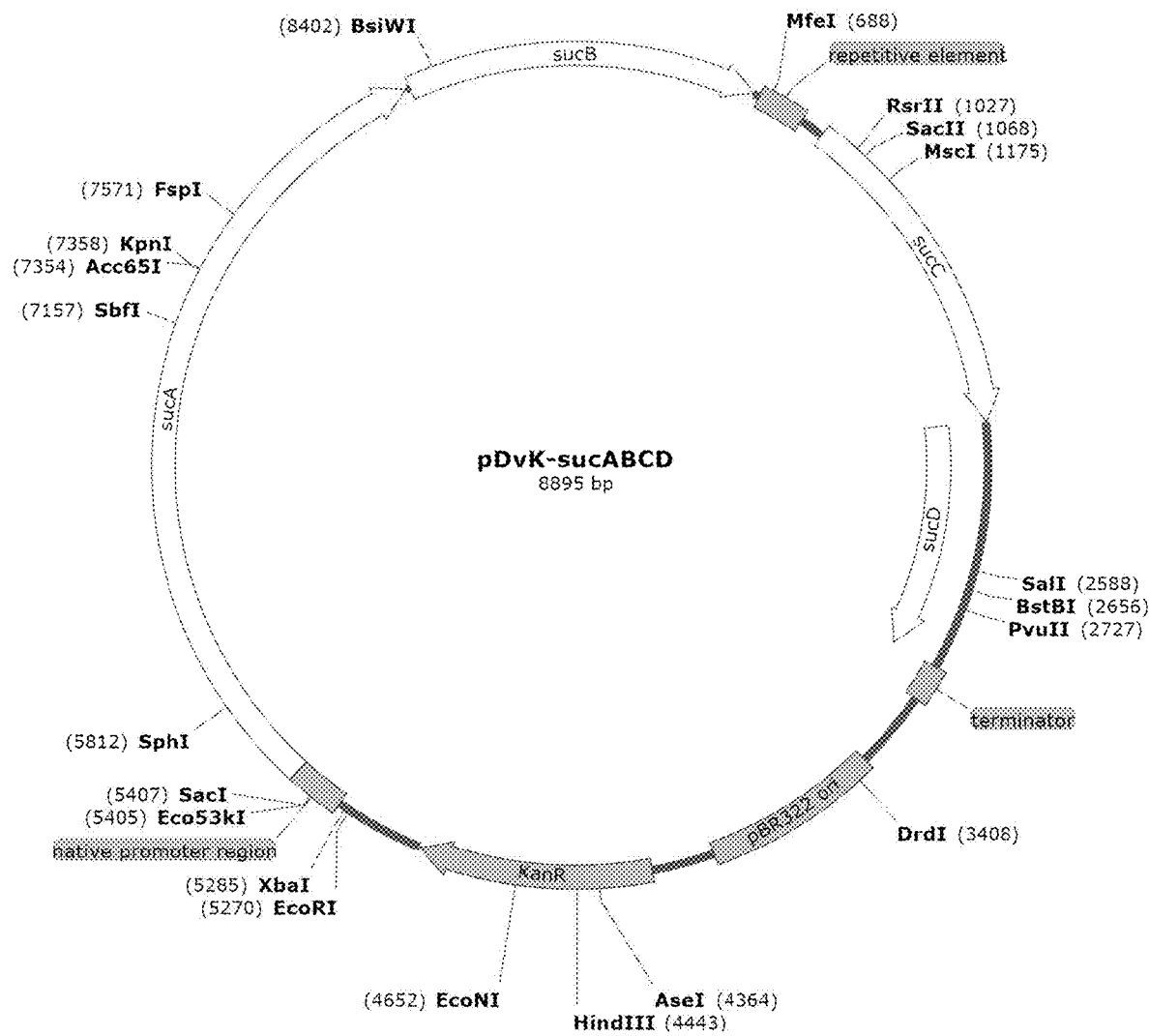
Figure 3C:
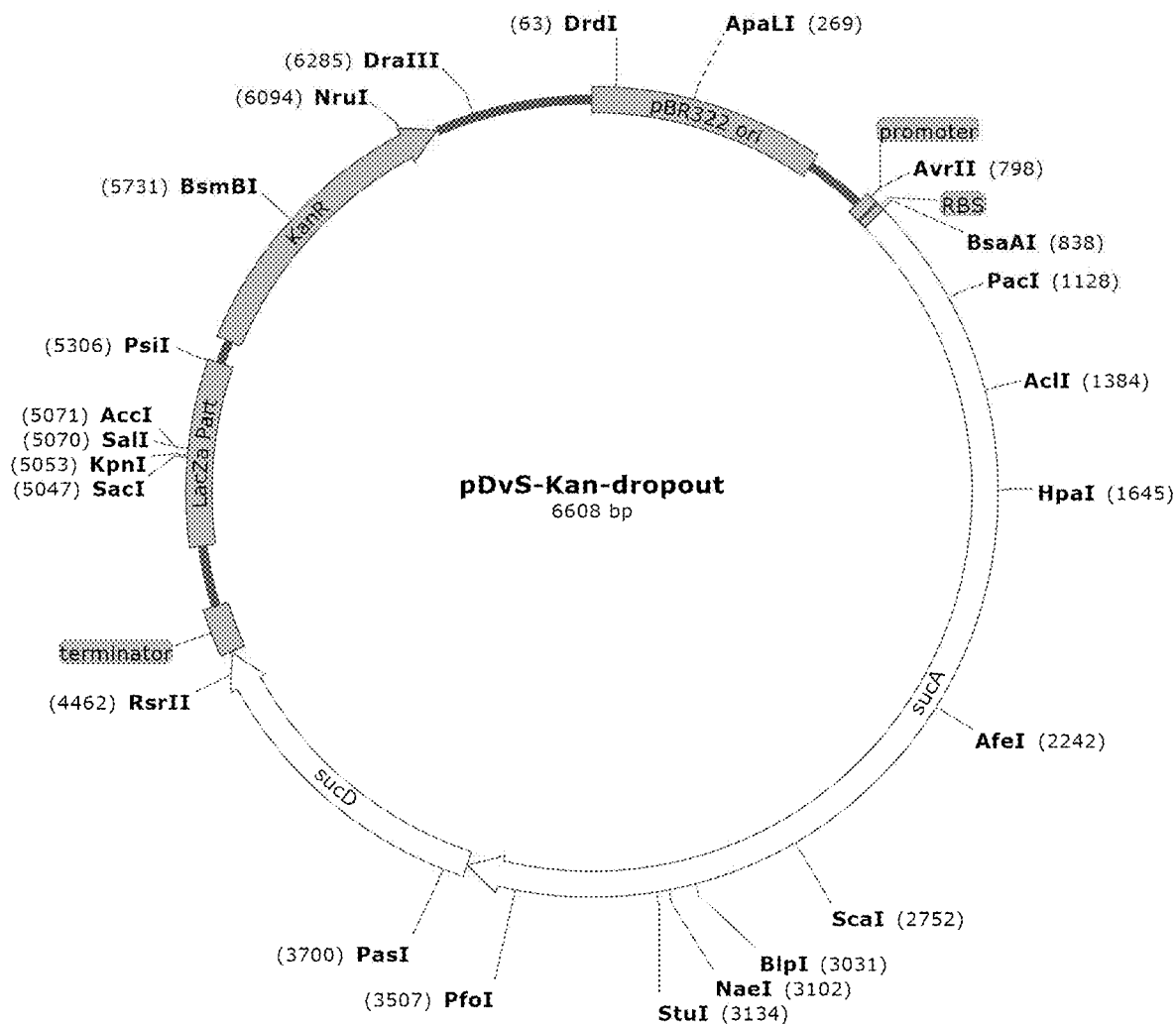
Figure 3D:
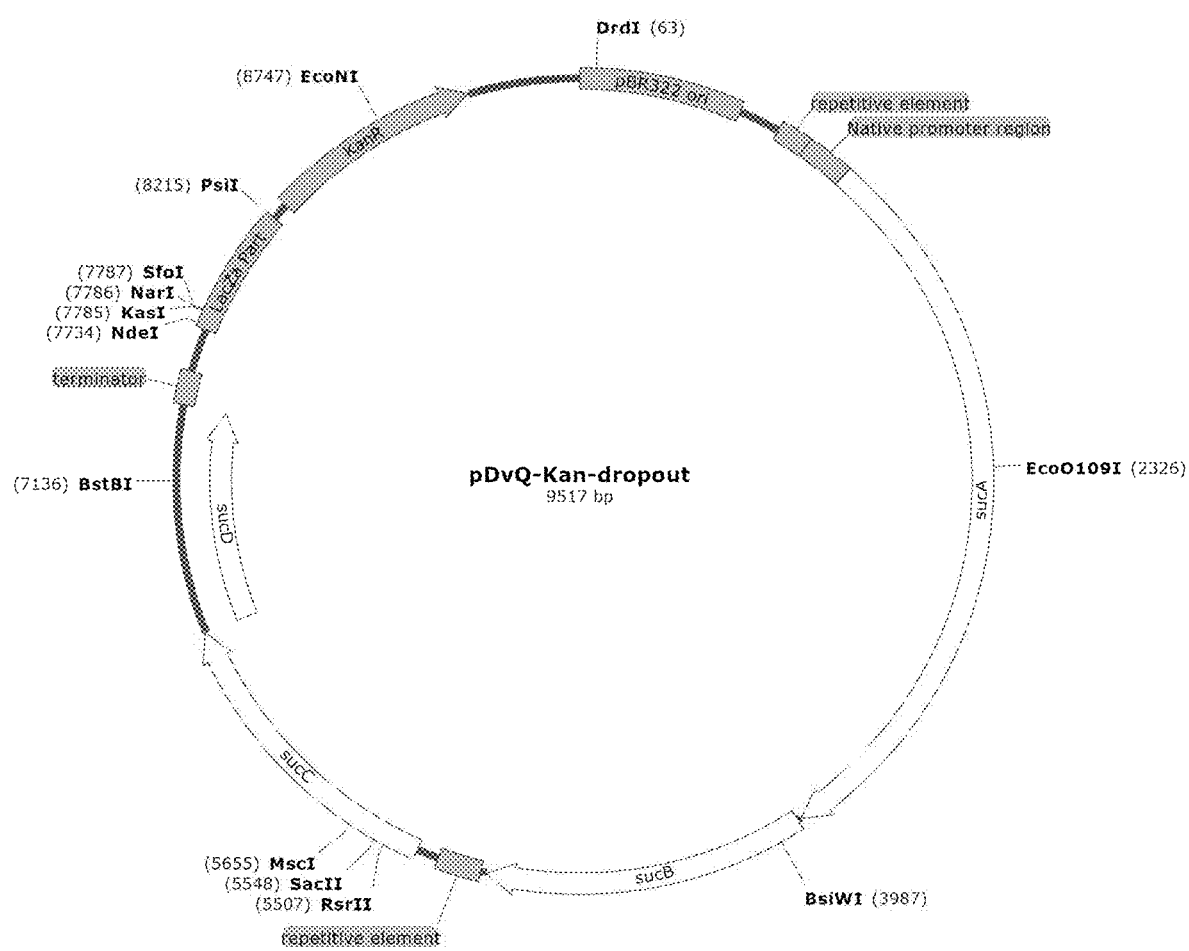
Figure 3E:
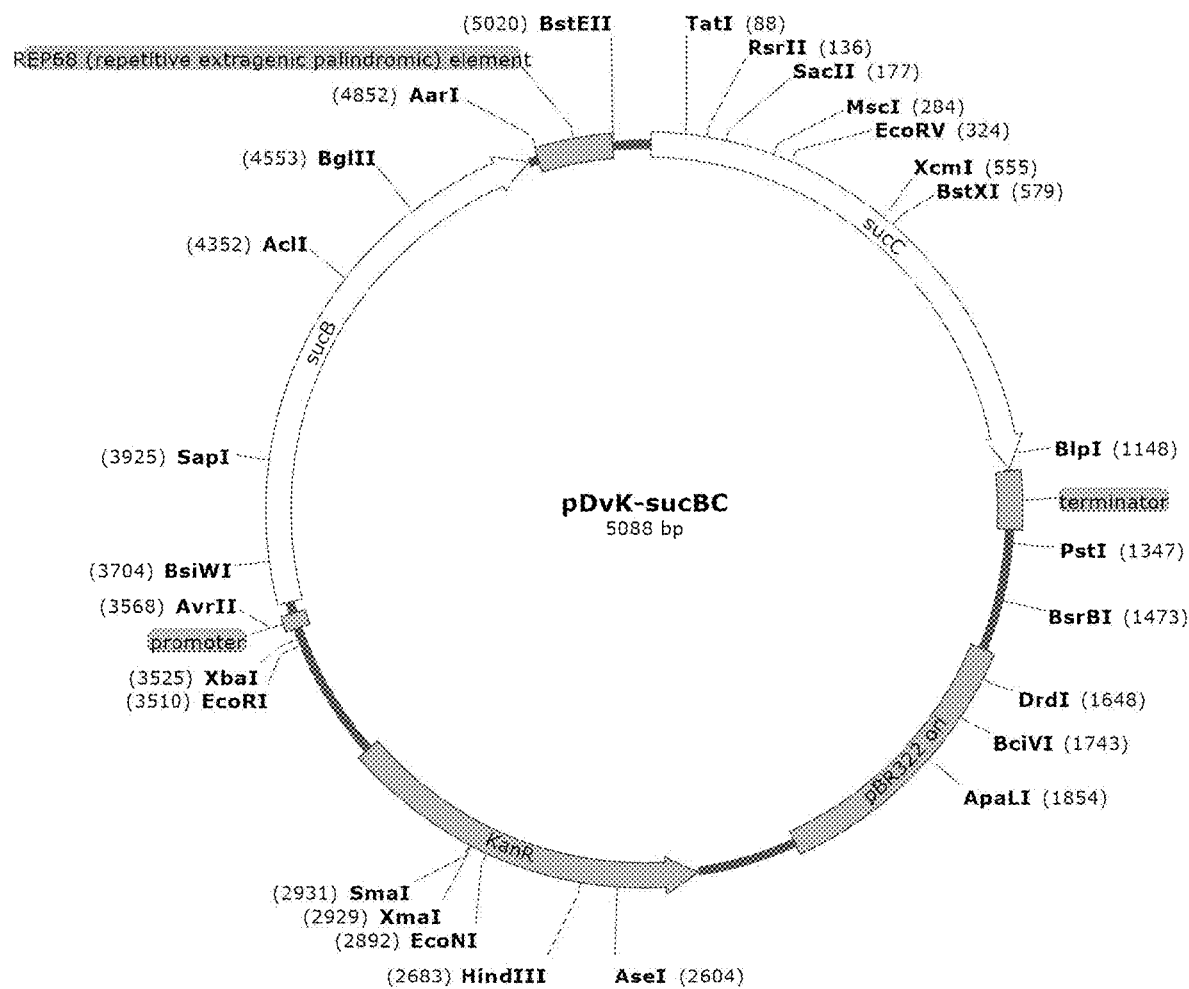

In FIG. 3A, a map of plasmid pDvK-SucAD, according to the current invention is provided. It was used to test for plasmid retention in nonselective media, as hosted in ΔsucAD cells. In this case, the plasmid retains kanamycin resistance markers for later testing. Although promoters, RBS, and terminators are specifically enumerated here, the experiments have shown effectively no difference in expression upon varying these (SEQ ID NO: 4). In FIG. 3B, we provide a map of plasmid pDvK-SucABCD, used to test for plasmid retention in nonselective media, as hosted in ΔsucABCD cells. According to the current invention, the plasmid retains kanamycin resistance markers for later testing. Although promoters, RBS, and terminators are specifically enumerated here, the experiments have shown effectively no difference in expression upon varying these (SEQ ID NO: 5). In FIG. 3C, we see the plasmid map of pDvS-Kan of the invention, wherein the kanamycin resistance marker is easily removed by the gene of interest, and the genes sucAD can instead be used as a selection marker. Although promoters, RBS, and terminators are specifically enumerated here, the experiments have shown effectively no difference in expression upon varying these (SEQ ID NO: 6). In FIG. 3E, a map of plasmid pDvK-SucBC, according to the current invention is provided. It was used to test for plasmid retention in nonselective media, as hosted in ΔsucABCD cells in combination with pDvK-SucAD. In this case, the plasmid retains kanamycin resistance markers for later testing. Although promoters, RBS, and terminators are specifically enumerated here, the experiments have shown effectively no difference in expression upon varying these sequences (SEQ ID NO: 10).

Figure 4A:
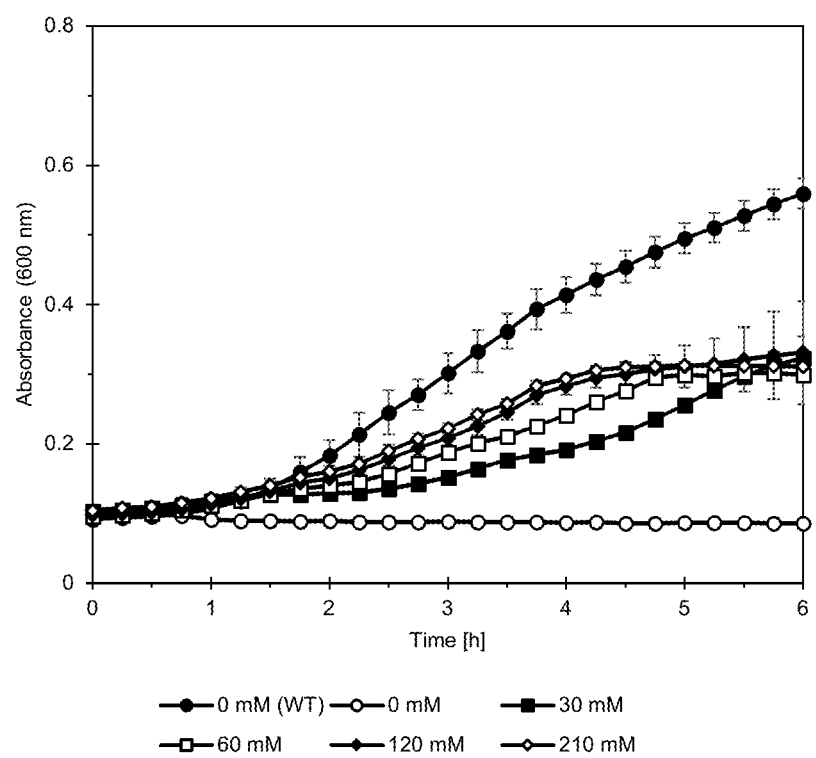
FIGS. 4A-4B. Show succinate pathway knockout mutants, such as BW25113 ΔsucAD (FIG. 4A) and BW25113 ΔsucABCD (FIG. 4B), cannot grow on rich fermentation media.
Figure 4B:
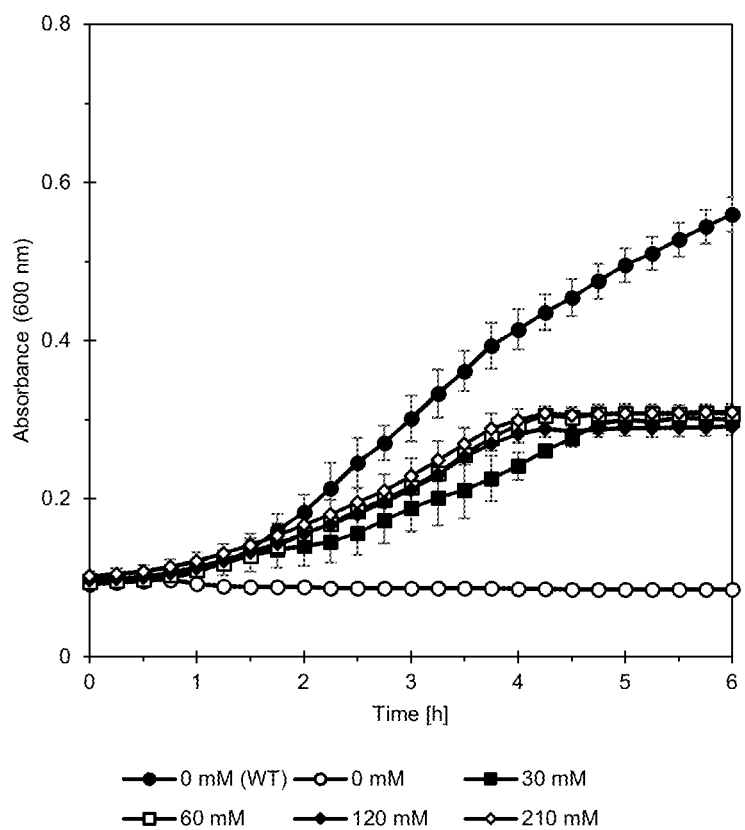

In FIG. 4A, applicants show the succinate pathway knockout mutant BW25113 ΔsucAD cannot grow on rich fermentation media Luria Broth. However, supplanting the media with diaminopimelic acid (DAP) allows for an increase in growth rate, correlating to the concentration of DAP provided. According to the current invention, the plasmid map of pDvQ-Kan is provided in FIG. 3D, wherein the kanamycin resistance marker is easily removed by the gene of interest, and the genes sucABCD can instead be used as a selection marker. Although promoters, RBS, and terminators are specifically enumerated here, the experiments have shown effectively no difference in expression upon varying these (SEQ ID NO: 7). In FIG. 4B, applicants demonstrate that the succinate pathway knockout mutant BW25113 ΔsucABCD cannot grow on rich fermentation media Luria Broth. However, supplanting the media with diaminopimelic acid (DAP) allows for an increase in growth rate, correlating to the concentration of DAP provided.

Figure 5:
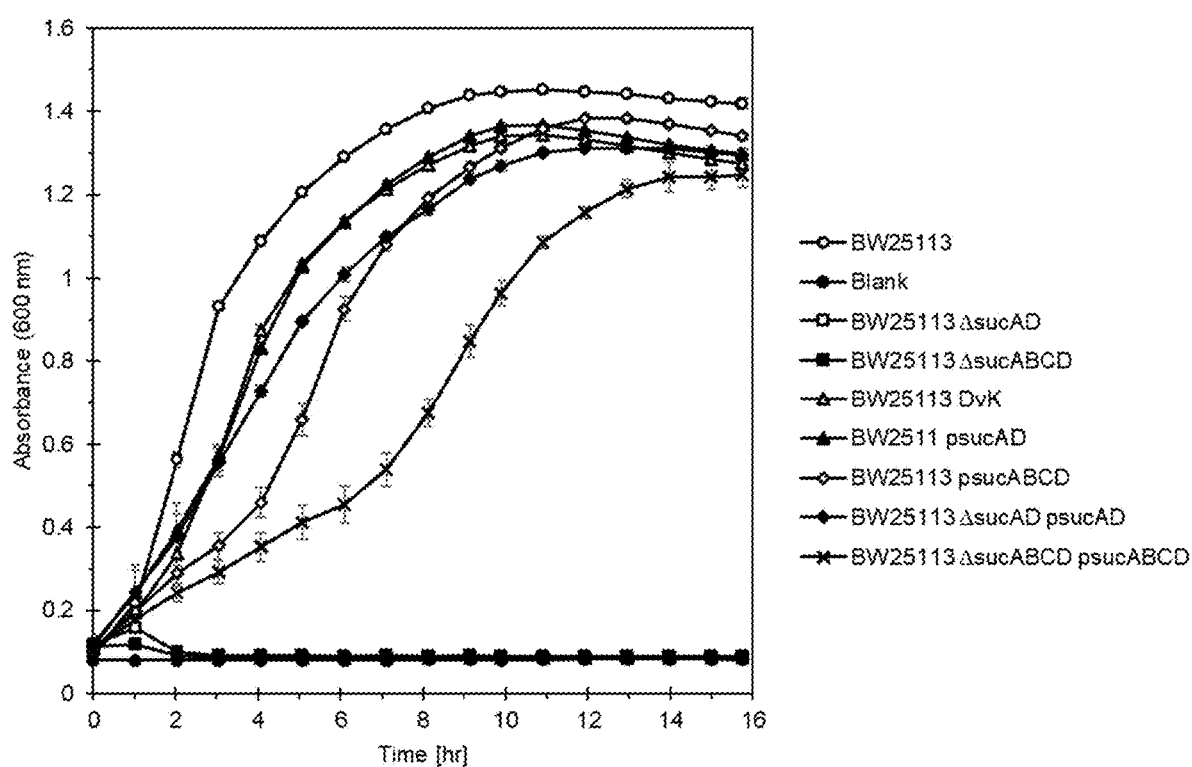
FIG. 5. Growth curves of relevant cells on nonselective media. Shows differences between complementation of double- or quadruple knockouts FIGS. 6A-6B. Plasmid maps of succinate addiction vectors engineered to express GFP. dvp-a8-skb-sfgfp (FIG. 6A); and pDvQ-GFP (FIG. 6B).
Figure 6A:
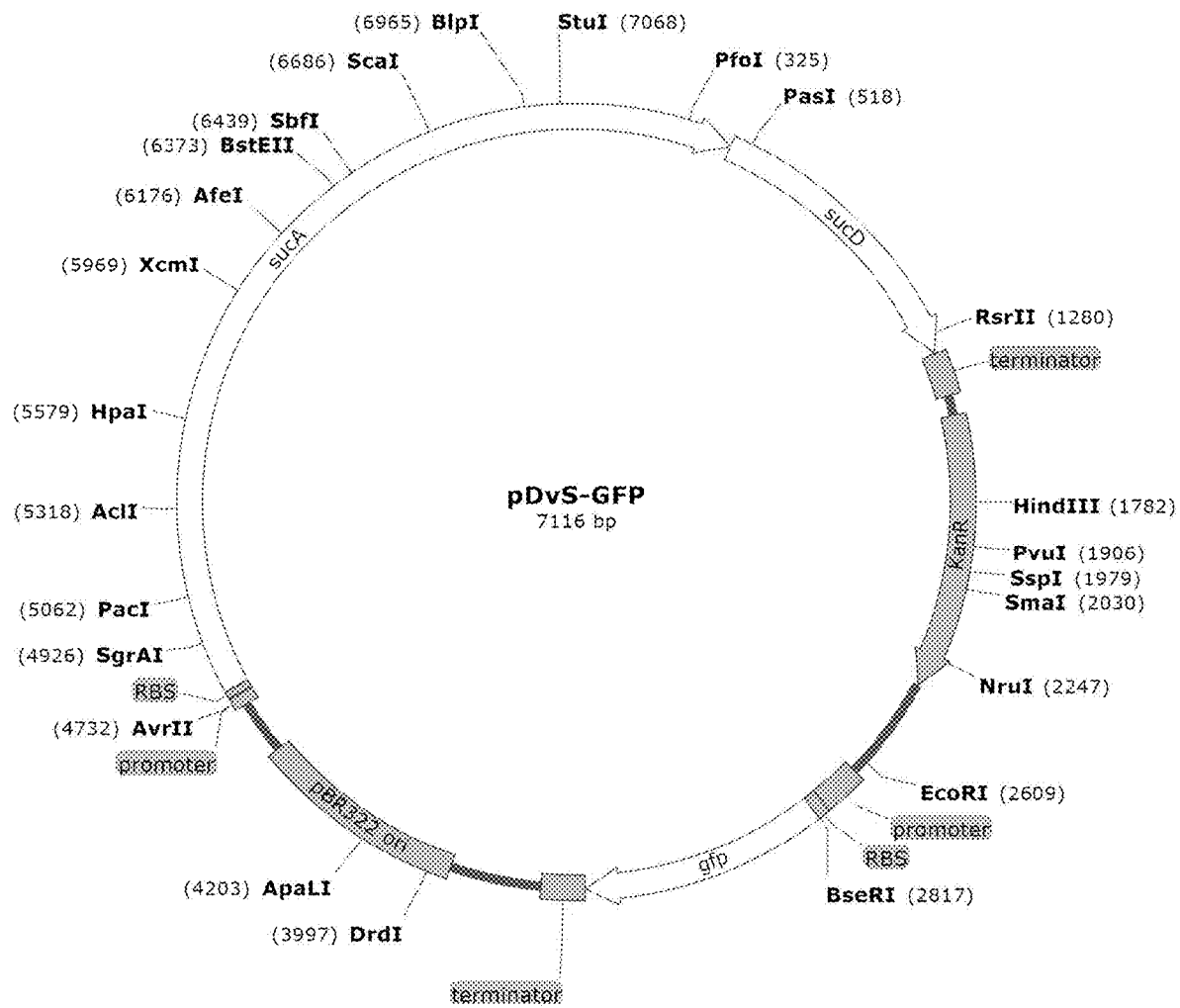
Figure 6B:
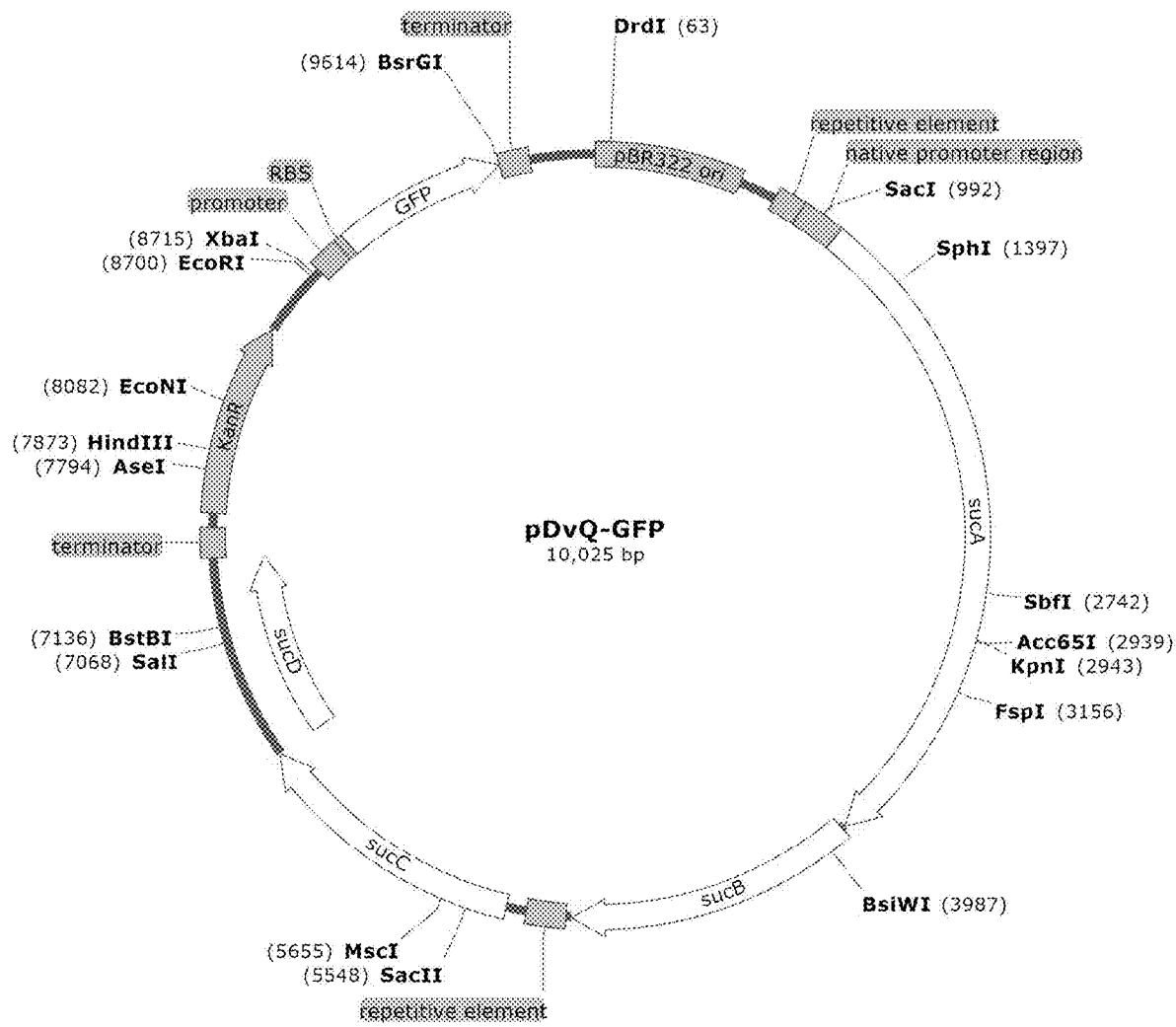
Figure 7:
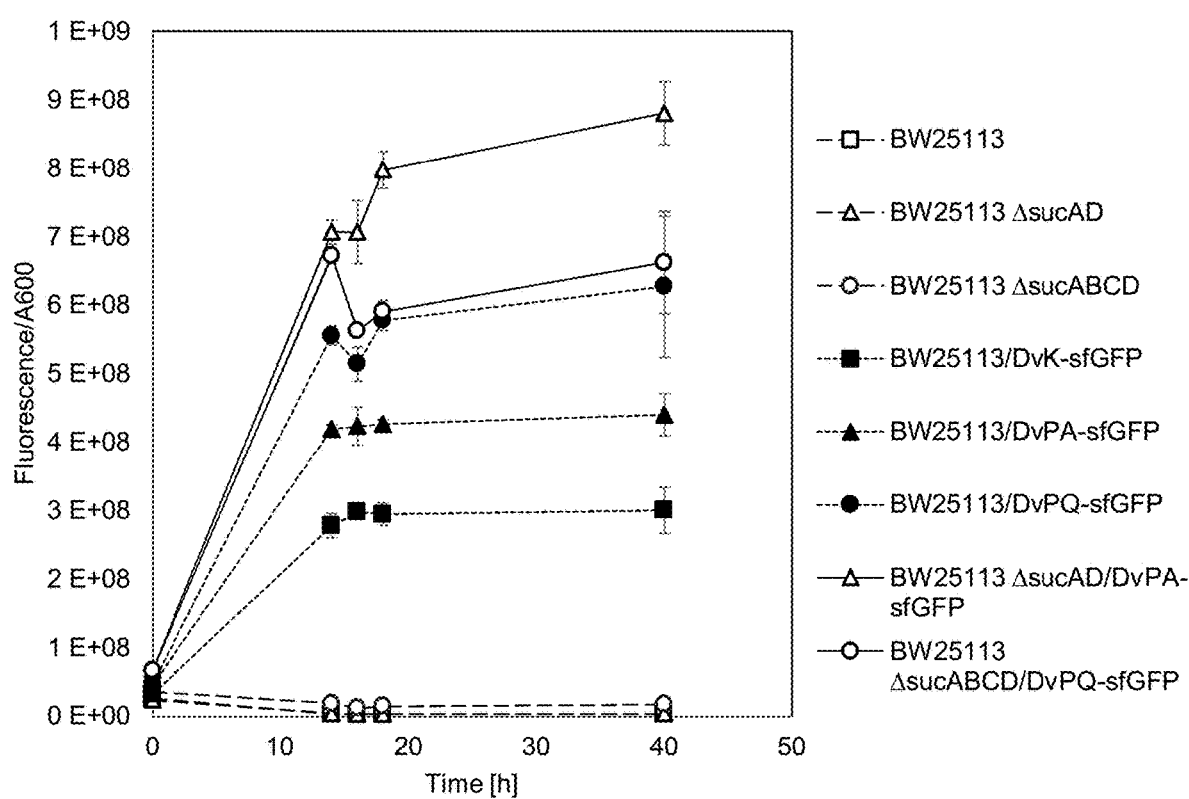
FIG. 7. Shows the production levels of GFP according to the transformed cellular system of the invention.

In FIG. 5, we provide the rescue of growth phenotypes with plasmid-borne sucA(BC)D in artificial operons. Deletions of sucAD and sucABCD from *E. coli* BW25113 do not grow at all on rich fermentation media Luria Broth. However, supplying the cells with plasmids pDvK-SucAD and pDvK-SucABCD, respectively, allows the cells to reach densities of close to that of wild-type BW25113. In FIG. 6A, the plasmid map of pDvS-GFP contains a sequence encoding the green fluorescent protein cloned into the pDvS vector, wherein the kanamycin resistance marker is easily removed by the gene of interest. (SEQ ID NO: 8) is provided. In FIG. 6B, a plasmid map of pDvQ-GFP containing a sequence encoding the green fluorescent protein cloned into the pDvQ vector (SEQ ID NO: 9) is provided. In FIG. 7, we see the production levels of green fluorescent protein (GFP), normalized by cell density according to the transformed cellular system of the invention. The cells containing the deletions and corresponding complements (open symbols, solid lines) exhibit more GFP per unit cell density than those with wild-type backgrounds (filled symbols, dotted lines), or those without plasmids (open symbols, dashed lines). In Table 1 we see that over time in the absence of kanamycin selection, the cells lacking the deletions lose kanamycin resistance (borne on the plasmids) within a few days, whereas the deletion mutants retain their resistance and their plasmids over the entire course of the study.

In addition, in Table 1, Applicants demonstrate that the Fraction of colony forming units (cfu) that retains a KanR plasmid over days. *E. coli* BW25113 was transformed with three Kan resistant plasmids (pDvK-sucAD, pDvK-sucABCD, and pDvK, rows A-D). *E. coli* BW25113 deletions in sucAD and sucABCD were also transformed with complement plasmids (pDvK-sucAD, pDvK-sucABCD, respectively, rows E-F). 50-mL cultures were grown in LB without kanamycin as selective pressure. Aliquots of cells were plated on kanamycin and non-selective plates and cfu calculated daily. The fraction of KanR cfu over total cfu is reported.

Over time in the absence of kanamycin selection, the cells lacking the deletions lose kanamycin resistance (borne on the plasmids) within a few days, whereas the deletion mutants retain their resistance and their plasmids over the entire course of the study.

TABLE 1

Table of growth characteristics for the retention of a single plasmid in the system. Fraction of cfu that retain kanamycin sensitivity (and thus maintain the plasmid expressing succinate pathway and kanamycin resistance genes) over time.

| Strain | Plasmid | Day 1 | Day 2 | Day 3 | Day 4 | Day 5 | Day 6 | Day 7 | Day 8 |
|---|---|---|---|---|---|---|---|---|---|
| BW25113 | | 0 | 0 | 0 | 0 | 0 | 0 | 0 | 0 |
| BW25113 ΔsucAD | | 0 | 0 | 0 | 0 | 0 | 0 | 0 | 0 |
| BW25113 ΔsucABCD | | 0 | 0 | 0 | 0 | 0 | 0 | 0 | 0 |
| BW25113 | pDvK-sucAD | <1.0 | 1.35 ± 0.53 | 0.75 ± 0.17 | 0.48 ± 0.03 | 0.09 ± 0.03 | 0.08 ± 0.08 | ~0 | ~0 |
| BW25113 | pDvK-sucABCD | <1.0 | <1.0 | 0.04 ± 0.06 | 0.04 ± 0.00 | 0.16 ± 0.05 | ~0 | ~0 | ~0 |
| BW25113 | pDvK | <1.0 | 0.96 ± 0.12 | 0.63 ± 0.17 | 0.55 ± 0.19 | 0.44 ± 0.15 | 0.50 ± 0.37 | 0.08 ± 0.07 | 0.12 ± 0.15 |
| BW25113 ΔsucAD | pDvK-sucAD | 0.99 ± 0.23 | 1.93 ± 0.12 | 0.84 ± 0.17 | 1.05 ± 0.42 | 1.06 ± 0.04 | 1.30 ± 0.61 | 1.15 ± 0.30 | 1.11 ± 0.19 |
| BW25113 ΔsucABCD | pDvK-sucABCD | 0.86 ± 0.02 | 0.99 ± 0.27 | 0.98 ± 0.17 | 1.26 ± 0.44 | 1.02 ± 0.02 | 0.94 ± 0.21 | 1.23 ± 0.24 | 1.19 ± 0.01 |

Maintenance of Multiple Plasmids in the System

A similar experiment was performed to test the maintenance of multiple plasmids in the system. Cells of BW25113 ΔsucABCD should not be able to grow in LB without supplementation of DAP, unless at least two of the genes sucAB and sucCD are expressed on plasmids. Plasmids pDVK-sucAD and pDVK-sucBC, were constructed. Neither of these plasmids has a sufficient set of genes to allow growth of BW25113 ΔsucABCD without DAP supplementation, but they will in combination. Without supplementation with DAP, the cells retained their kanamycin resistance, and thus their ability to maintain both plasmids (Tables 2, 3).

TABLE 2

Retention of Two-Plasmids. Fraction of cfu that retain kanamycin sensitivity (and thus maintain the plasmids expressing succinate pathway and kanamycin resistance genes) over time).

| Strain | Plasmid(s) | Day 1 |
|---|---|---|
| BW25113 | pDVK | 0.49 ± 0.27 |
| BW25113 ΔsucABCD | pDVK-sucBC and pDVP-sucAD | 0.69 ± 0.37 |

Retention of both plasmids utilized according to the current invention is shown in patch plates, wherein colonies of each strain/plasmid combination were struck on LB agar plates of different media conditions. Only with a complimentary and/or complete set of genes sucAB sucCD can *E. coli* BW25113 ΔsucABCD grow without DAP supplementation. Kanamycin resistance shows maintenance of the plasmids, here two, as KanR is linked to the succinate operon genes.

TABLE 3

Retention of Two-Plasmids. Patch growth of plasmids on different media. Cultures of each strain/plasmid were grown in LB + DAP overnight and diluted to $OD_{600}$ = 1.0. Ten μL of this dilution (and serial 50-fold dilutions) were plated onto the media conditions in each column. − = no growth. + = growth patch observed with $OD_{600}$ = 1.0 cells. ++ = growth patch observed from 50-fold serial dilution ($OD_{600}$ = 0.02). +++ = growth patch observed from 2500-fold serial dilution ($OD_{600}$ = 0.0004). ++++ = growth patch observed from 125,000-fold serial dilution ($OD_{600}$ = 0.000008).

| Strain | Plasmid(s) | LB | LB + Kan | LB + DAP | LB + $Kan_{50}$ + DAP |
|---|---|---|---|---|---|
| BW25113 | | ++++ | − | ++++ | − |
| BW25113 ΔsucABCD | | − | − | ++++ | − |
| BW25113 ΔsucABCD | pDVK-sucAD | + | − | ++++ | ++++ |
| BW25113 ΔsucABCD | pDVK-sucBC | − | − | ++++ | ++++ |
| BW25113 ΔsucABCD | pDVK-sucAD and pDVK-sucBC | +++ | +++ | ++++ | +++ |

Cultivation of Plasmid-Addicted Strains

Plasmid-bearing *E. coli* strains were grown in LB without additional supplementation in 24-well plates and in a Bio-Lector flower plates (Funke et al., 2009).

To achieve tight regulation of toxic gene expression, a tightly regulable promoter like the arabinose-inducible PBAD promoter (Guzman et al., 1995) is preferably used, in particular in the case that the marker protein is per se toxic to the cells.

Another way to control expression of the marker gene is by using constitutive promoters in combination with a gene that is non-toxic (e.g. a reporter gene) or only toxic under defined conditions, e.g. the *Bacillus subtilis* sacB gene, which is only toxic to *E. coli* when sucrose is present.

The promoter is chosen in coordination with the effect of the marker gene product and the required efficiency of down-regulation or silencing effect. For example, for a construct containing a non-toxic or less toxic marker gene, a stronger promoter is desirable.

Additional Embodiments

As is evident from the foregoing description, certain aspects of the present disclosure are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the present disclosure.

Moreover, unless defined otherwise, all technical and scientific terms used herein have the same meaning as commonly understood by one of ordinary skill in the art to which the disclosure belongs. Although any methods and materials equivalent to or those described herein can be used in the practice or testing of the present disclosure, the preferred methods and materials are described above.

Although the foregoing invention has been described in some detail by way of illustration and example for purposes of understanding, it will be apparent to those skilled in the art that certain changes and modifications may be practiced. Therefore, the description and examples should not be construed as limiting the scope of the invention, which is delineated by the appended claims.

Accordingly, it is to be understood that the embodiments of the invention herein providing for the production of specific molecules are merely illustrative of the application of the principles of the invention. It will be evident from the foregoing description that changes in the form, methods of use, and applications of the elements of the disclosed production methods and selected microbial strains may be resorted to without departing from the spirit of the invention, or the scope of the appended claims.

STATEMENT OF INDUSTRIAL APPLICABILITY/TECHNICAL FIELD

This disclosure has applicability in the commercial production of food ingredients, fragrances, medicines and pharmaceuticals. This disclosure relates generally to a method for enhanced and more precisely controlled biosynthetic production of desired end products via selected microbial strains.

LITERATURE CITED AND INCORPORATED BY REFERENCE

Baba, T., et al., *Construction of Escherichia coli K-12 in-frame, single-gene knockout mutants: the Keio collection*, MOL. SYST. BIOL. 2, 2006.

Balbas, P., et al; *Understanding the Art of Producing Protein and Nonprotein Molecules in Escherichia coli*; MOLECULAR BIOTECHNOLOGY (2001) vol. 19, (3) pp. 251-67.

Balbas, P. et al; *Plasmid vector pBR322 and its special purpose derivatives—a review*; GENE (1986) vol. 50 pp. 3-40.

Beck, C. F. et al; *A Multifunctional Gene (tetR) Controls Tn10-encoded Tetracycline Resistance*; JOURNAL OF BACTERIOLOGY (1982) vol. 150 No. 2 pp. 633-42.

Brantl, S., *Antisense RNAs in plasmids: control of replication and maintenance*, Academic Press, PLASMID 48 (2002) pp. 165-173.

Brosius, J., et al; *Construction and Fine Mapping of Recombinant Plasmids Containing the rrnB Ribosomal RNA Operon of E. coli*; PLASMID (1981) vol. 6 No. 1 pp. 112-18.

Chang, A. C. Y., et al., *Construction and Characterization of Amplifiable Multicopy DNA Cloning Vehicles Derived for the P15A Cryptic Miniplasmid*; J. BACTERIOLOGY (1978) vol. 134 No. 3 pp. 1141-56.

Choi Y. J., et al; *Novel, Versatile, and Tightly Regulated Expression System for Escherichia coli Strains*. APPLIED AND ENVIRONMENTAL MICROBIOLOGY (2010) vol 76, No. 15, pp. 5058-66.

Cranenburgh, R. M. et al., *Escherichia coli strains that allow antibiotic free plasmid selection and maintenance by repressor titration*, NUCLEIC ACIDS RESEARCH, 2001 vol. 29, No. 5, 1-6.

Datsenko, K. A., and Wanner, B. L., *One-step inactivation of chromosomal genes in Escherichia coli K-12 using PCR products*, PROC. NATL. ACAD. SCI. U.S.A. 97, 6640-5. (2000)

Deboy, R. T., et al; *Target Site Selection by Tn7: attTn7 Transcription and Target Activity*; JOURNAL OF BACTERIOLOGY (2000) vol. 182 No. 11 pp. 3310-3313.

Del Solar, Gloria et al., *Replication and Control of Circular Bacterial Plasmids*, MICROBIOLOGY AND MOLECULAR BIOLOGY REVIEWS (1998) vol. 62, No. 2, pp. 434-64.

Eguchi, Yutaka., et al., *Complexes Formed by Complementary RNA Stem-loops. Their Formation, Structure and Interaction with ColE1 Rom Protein*, JOURNAL MOLECULAR BIOLOGY (1991) vol. 220 pp. 831-842.

Fu X., et al., *Development of a Chromosome-Plasmid Balanced Lethal System of Lactobacillus Acidophilus with thyA Gene as Selective Marker*, MICROBIOL. IMMUNOL., 44(7) p 551-56 (2000).

Funke, M. et al., *The baffled microtiter plate: Increased oxygen transfer and improved online monitoring in small scale fermentations*, BIOTECHNOL. BIOENG. (2009) 103, 1118-28.

Furste, J. P., et al., *Molecular Cloning of the Plasmid RP4 Primase Region in a Multi-Host-Range tacP Expression Vector*, GENE (1986) vol. 48 pp. 119-131.

Gerdes K., et al., *Mechanism of post-segregational killing by the hok/sok system of plasmid R1: sok antisense RNA regulates formation of a hok mRNA species correlated with killing of plasmid-free cells*, MOL. MICROBIOL. (1990) 4(11): 1807-18.

Gerdes, S. Y., et al., *Experimental Determination and System Level Analysis of Essential Genes in Escherichia coli MG1655*, JOURNAL OF BACTERIOLOGY (2003) vol. 185 No. 19 pp. 5673-5684.

Haegg, P., et al., *A Host/Plasmid System that is not Dependent on Antibiotics and Antibiotic Genes for Stable Plasmid Maintenance in Eschericia coli.*, JOURNAL OF BIO TECHNOLOGY (2004) vol. 111 pp. 17-30.

Helinski, D. R., et al; *Replication Control and Other Stable Maintenance Mechanisms of Plasmids* (1996) American Society for Microbiology Press, Washington, D.C., pp. 2295-2324.

Hiszczynska-Sawicka, Elzbieta., et al., *Effect of Integration Host Factor on RNA II Synthesis in Replication of Plasmid Containing orip15A*, PLASMID (1998) vol. 40 pp. 150-157.

Herring, Christopher D., et al., *Conditional Lethal Amber Mutations in Essential Escherichia coli Genes*, JOURNAL OF BACTERIOLOGY (2004) vol. 186, No. 9 pp. 2673-2681.

Jensen, L. Bogo., et al., *A Substrate-Dependent Biological Containment System for Pseudonomas Putida Based on the Escherichia coli gef Gene*, APPLIED AND ENVIRONMENTAL MICROBIOLOGY (1993) vol. 59, No. 11 pp. 3713-3717.

Knudsen, Steen., et al., *Development and Testing of Improved Suicide Functions for Biological Containment of Bacteria*, APPLIED AND ENVIRONMENTAL MICROBIOLOGY (1995) vol. 61, No. 3 pp. 985-991.

Kroll, J., et al., *Plasmid Addiction Systems: Perspectives and Applications in Biotechnology*, MICROB. BIOTECHNOL., 3(6) pp 634-57 (2010).

Kues, U., et al., *Replication of Plasmids in Gram-Negative Bacteria*, MICROBIOLOGICAL REVIEWS (1989) vol. 53, No. 4 pp. 491-516.

Mairhofer, Jurgen et al.; *A novel antibotic free plasmid selection system: Advances in safe and efficient DNA therapy*, BIOTECHNOLOGY JOURNAL (2008) 3, pp. 83-89.

Mattozzi, M. D. et al., *Expression of the sub pathways of the Chloroflexus aurantiacus 3-hydroxypropionate carbon fixation bicycle in E. coli: Toward horizontal transfer of autotrophic growth*, METAB. ENG. 16, 130-139. (2013).

Merlin, S., et al., *Assessment of Quantitative Models for Plasmid ColE1 Copy Number Control*, J. MOL. BIOL. (1995) vol. 248 pp. 211-19.

Michel, Gerhard and Dietmar Schomberg; METABOLIC PATHWAYS. (2012) John Wiley and Sons, New York O'Kennedy, R. D., et al., *Effects of Fermentation Strategy on the Characteristics of Plasmid DNA Production*, BIOTECHNOLOGY APPL. BIOCHEM. (2003) vol. 37 pp. 83-90.

O'Kennedy, R. D., et al., *Effects of Growth Medium Selection on Plasmid DNA Production and Initial Processing Steps*, JOURNAL OF BIOTECHNOLOGY (2000) vol. 76 pp. 175-183.

Postle, K., et al; Nucleotide Sequence of the Repressor Gene of the TN10 Tetracycline Resistance Determinant; NUCLEIC ACIDS RESEARCH (1984) vol. 12, No. 12 pp. 4849-4863.

Pfaffenzeller, I., *Using ColE1-derived RNA I for suppression of a bacterially encoded gene: implication for a novel plasmid addiction system*, BIOTECH. J. (2006), pp. 1-7.

Rawlings, D. E.; *Protein Toxin-Antitoxin, Bacterial Plasmid Addiction Systems and their evolution with Special reference to the pas System of pTF-FC2*; FEMS Microbiology Letters (1999) vol. 176 pp. 269-77.

Reinikainen, P., et al; *Escherichia coli Plasmid Production in Fermenter*; BIOTECHNOLOGY BIOENGINERING (1988) vol. 33 pp. 386-93.

Ronchel, M. Carmen., et al; *Characterization of Cell Lysis in Pseudomonas putida induced Upon Expression of Heterologous Killing Genes*, APPLIED AND ENVIRONMENTAL MICROBIOLOGY, (1998) vol. 64, No. 12 pp. 4904-11.

Germán L. Rosano and Eduardo A. Ceccarelli, *Recombinant protein expression in Escherichia coli: advances and challenges*, MICROBIOL. (2014); 5:172.

Schumacher M. A., *Bacterial plasmid partition machinery: a minimalist approach to survival*, CURR OPIN STRUCT BIOL., (2012) Feb.;22(1):72-9

Tomizawa, Jun-Ichi., et al; *Plasmid ColE1 Incompatibility Determined by Interaction of RNA I with Primer Transcript*; PROC. NATL. ACAD. SCI. USA (1981) vol. 78, No. 10 pp. 6096-6100.

Tomizawa, Jun-Ichi, *Control of ColE1 Plasmid replication: The Process of Binding of RNA I to the Primer Transcript*, CELL (1984) vol. 38 pp. 861-870.

Tomizawa, Jun-Ichi; *Control of ColE1 Plasmid Replication: Binding of RNA I to RNA II and Inhibition of Primer Formation*, CELL (1986) vol. 47 pp. 89-97.

Torres, B., et al., *As Gene Containment Strategy Based on a Restriction Modification System*, ENVIRONMENTAL MICROBIOLOGY (2000) vol. 2, No. 5 pp. 555-63.

Vieira, J., et al; *The pUC Plasmids, an M13mp7-Derived System for Insertion Mutagenesis and Sequencing with Synthetic Universal Primers*; GENE (1982) vol. 19 pp. 259-68.

Williams, S. G., et al., *Repressor Titration: A Novel System for Selection and Stable Maintenance of Recombinant Plasmids*, NUCLEIC ACIDS RESEARCH (1998) vol. 26, No. 9 pp. 2120-24.

Yu., B. J., et al., *sucAB and sucCD are mutually essential genes in Escherichia coli*., FEMS MICROBIOL. LETT. (2005) 254, 245-50.

Yu, D., et al; *An Efficient Recombination System for Chromosome Engineering in Escherichia coli*; PNAS (2000) vol. 97, No. 11 pp. 5978-83.

---

Sequences of Interest:

```
SEQ ID NO: 1 SE operon and genomic context sequence
ccggtcaggcactgactgtgaatgagaaaggcgaagatgtggttgttccgggactgtttgccgttggtgaaatcgct
tgtgtatcggtacacggcgctaaccgtctgggcggcaactcgctgctggacctggtggtctttggtcgcgcggcagg
tctgcatctgcaagagtctatcgccgagcagggcgcactgcgcgatgccagcgagtctgatgttgaagcgtctctgg
atcgcctgaaccgctggaacaataatcgtaacggtgaagatccggtggcgatccgtaaagcgctgcaagaatgtatg
cagcataacttctcggtcttccgtgaaggtgatgcgatggcgaaagggcttgagcagttgaaagtgatccgcgagcg
tctgaaaaatgcccgtctggatgacacttccagcgagttcaacacccagcgcgttgagtgcctggaactggataacc
tgatggaaacggcgtatgcaacggctgtttctgccaacttccgtaccgaaagccgtggcgcgcatagccgcttcgac
ttcccggatcgtgatgatgaaaactggctgtgccactccctgtatctgccagagtcggaatccatgacgcgccgaag
cgtcaacatggaaccgaaactgcgcccggcattcccgccgaagattcgtacttactaatgcggagacaggaaaatga
gactcgagttttcaatttatcgctataacccggatgtttgatgatgctccgcgtatgcaggattacaccctggaagcg
gatgaaggtcgcgacatgatgctgctggatgcgcttatccagctaaaagagaaagatcccagcctgtcgttccgccg
ctcctgccgtgaaggtgtgtgcggttccgacggtctgaacatgaacggcaagaatggtctggcctgtattacccga
tttcggcactcaaccagccgggcaagaagattgtgattcgcccgctgccaggtttaccggtgatccgcgatttggtg
gtagacatgggacaattctatgcgcaatatgagaaaattaagccttacctgttgaataatggacaaaatccgccagc
tcgcgagcatttacagatgccagagcagcgcgaaaaactcgacgggctgtatgaatgtattctctgcgcatgttgtt
caacctcttgtccgtctttctggtggaatcccgataagtttatcggcccggcaggcttgttagcggcatatcgtttc
ctgattgatagccgtgataccgagactgacagccgcctcgacggtttgagtgatgcattcagcgtattccgctgtca
cagcatcatgaactgcgtcagtgtatgtccgaagggcctgaacccgacgcgcgccatcggccatatcaagtcgatgt
tgttgcaacgtaatgcgtaaaccgtaggcctgataagacgcgcaagcgtcgcatcaggcaaccagtgccggatgcgg
cgtgaacgccttatccggcctacaagtcattacccgtaggcctgataagcgcagcgcatcaggcgtaacaaagaaat
gcaggaaatctttaaaaactgccctgacactaagacagttttaaaggttccttcgcgagccactacgtagacaag
agctcgcaagtgaaccccggcacgcacatcactgtgcgtggtagtatccacggcgaagtaagcataaaaaagatgct
taagggatcacgatgcagaacagcgctttgaaagcctggttggactcttcttacctctctggcgcaaaccagagctg
gatagaacagctctatgaagacttcttaaccgatcctgactcggttgacgctaactggcgttcgacgttccagcagt
tacctggtacgggagtcaaaccggatcaattccactctcaaacgcgtgaatatttccgccgcctggcgaaagacgct
tcacgttactcttcaacgatctccgaccctgacaccaatgtgaagcaggttaaagtcctgcagctcattaacgcata
ccgcttccgtggtcaccagcatgcgaatctcgatccgctgggactgtggcagcaagataaagtggccgatctggatc
cgtctttccacgatctgaccgaagcagcttccaggagaccttcaacgtcggttcatttgccagcggcaaagaaacc
atgaaactcggcgagctgctggaagccctcaagcaaacctactgcggccgattggtgccgagtatatgcacattac
cagcaccgaagaaaaacgctggatccaacagcgtatcgagtctggtcgcgcgactttcaatagcgaagagaaaaac
gcttcttaagcgaactgaccgccgctgaaggtcttgaacgttacctcggcgcaaaattccctggcgcaaaacgcttc
tcgctggaaggcggtgacgcgttaatcccgatgcttaaagagatgatccgccacgctggcaacagcggcacccgcga
agtggttctcgggatggcgcaccgtggtcgtctgaacgtgctggtgaacgtgctgggtaaaaaaccgcaagacttgt
```

Sequences of Interest:

```
tcgacgagttcgccggtaaacataaagaacacctcggcacgggtgacgtgaaataccacatgggcttctcgtctgac
ttccagaccgatggcggcctggtgcacctggcgctggcgtttaacccgtctcaccttgagattgtaagcccggtagt
tatcggttctgttcgtgcccgtctggacagacttgatgagccgagcagcaacaaagtgctgccaatcaccatccacg
gtgacgccgcagtgaccgggcagggcgtggttcaggaaaccctgaacatgtcgaaagcgcgtggttatgaagttggc
ggtacggtacgtatcgttatcaacaaccaggttggtttcaccacctctaatccgctggatgcccgttctacgccgta
ctgtactgatatcggtaagatggttcaggccccgattttccacgttaacgcggacgatccggaagccgttgcctttg
tgaccgtctggcgctcgatttccgtaacacctttaaacgtgatgtcttcatcgacctggtgtgctaccgccgtcac
ggccacaacgaagccgacgagccgagcgcaacccagccgctgatgtatcagaaaatcaaaaaacatccgacaccgcg
caaaatctacgctgacaagctggagcaggaaaaagtggcgacgctggaagatgccaccgagatggttaacctgtacc
gcgatgcgctggatgctggcgattgcgtagtggcagagtggcgtccgatgaacatgcactctttcacctggtcgccg
tacctcaaccacgaatgggacgaagagtacccgaacaaagttgagatgaagcgcctgcaggagctggcgaaacgcat
cagcacggtgccggaagcagttgaaatgcagtctcgcgttgccaagatttatggcgatcgccaggcgatggctgcga
gtgagaaactgttcgactggggcggtgcggaaaacctcgcttacgccacgctggttgatgaaggcattccggttcgc
ctgtcgggtgaagactccggtcgcggtaccttcttccaccgccacgcggtgatccacaaccagtctaacggttccac
ttacacgccgctgcaacatatccataacgggcagggcgcgttccgtgtctgggactccgtactgtctgaagaagcag
tgctgcgttttgaatatggttatgccaccgcagaaccacgcactctgaccatctgggaagcgcagttcggttgacttc
gccaacggtgcgcaggtggttatcgaccagttcatctcctctgcgaacagaaatggggccggatgtgtggtctggt
gatgttgctgccgcacggttacgaagggcaggggccggagcactcctccgcgcgtctggaacgttatctgcaactt
gtgctgagcaaaacatgcaggtttgcgtaccgtctaccccggcacaggtttaccacatgctgcgtcgtcaggcgctg
cgcgggatgcgtcgtccgctggtcgtgatgtcgccgaaatccctgctggcggtcgtggtttccagcctcga
agaactggcgaacggcaccttcctgccagccatcggtgaaatcgacgagcttgatccgaagggcgtgaagcgcgtag
tgatgtgttctggtaaggtttattacgacctgctggaacagcgtcgtaagaacaatcaacacgatgtcgccattgtg
cgtatcgagcaactctaccgttcccgcataaagcgatgcaggaagtgttgcagcagtttgctcacgtcaaggattt
tgtctggtgccaggaagagccgctcaaccagggcgcatggtactgcagccagcatcattcgtgaagtgattccgt
ttggggcttctctgcgttatgcaggccgcccggcctccgcctctccggcggtagggtatatgtccgttcaccagaaa
cagcaacaagatctggttaatgacgcgctgaacgtcgaataaataaaggatacacaatgagtagcgtagatattctg
gtccctgacctgcctgaatccgtagccgatgccaccgtcgcaacctggcataaaaaaccggcgacgcagtcgtacg
tgatgaagtgctggtagaaatcgaaactgacaaagtggtactggaagtaccggcatcagcagacggcattctggatg
cggttctggaagatgaaggtacaacggtaacgtctcgtcagatccttggtcgcctgcgtgaaggcaacagcgccggt
aaagaaaccagcgccaaatctgaagagaaagcgtccactccggcgcaacgccagcaggcgtctctggaagagcaaaa
caacgatgcgttaagcccggcgatccgtcgcctgctggctgaacacaatctcgacgccagcgccattaaaggcaccg
gtgtgggtggtcgtctgactcgtgaagatgtggaaaaacatctggcgaaagccccggcgaaagagtctgctccggca
gcggctgctccggcggcgcaacccgctctggctgcacgtagtgaaaaacgtgcccgatgactcgcctgcgtaagcg
tgtggcagagcgtctgctggaagcgaaaaactccaccgccatgctgaccacgttcaacgaagtcaacatgaagccga
ttatggatctgcgtaagcagtacggtgaagcgtttgaaaaacgccacggcatccgtctgggctttatgtccttctac
gtgaaagcggtggttgaagccctgaaacgttaccggaagtgaacgcttctatcgacggcgatgacgtggtttacca
caactatttcgacgtcagcatggcggtttctacgccggcggcctggtgacgccggttctgcgtgatgtcgataccc
tcggcatggcagacatcgagaagaaaatcaaagagctggcagtcaaaggccgtgacggcaagctgaccgttgaagat
ctgaccggtggtaacttcaccatcaccaacggtggtgtgttcggttccctgatgtctacgccgatcatcaacccgcc
gcagagcgcaattctgggtatgcacgctatcaaagatcgtccgatggcggtgaatggtcaggttgagatcctgccga
tgatgtacctggcgctgtcctacgatcaccgtctgatcgatggtcgcgaatccgtgggcttcctggtaacgatcaaa
gagttgctggaagatccgacgcgtctgctgctggacgtgtagtagtttaagtttcacctgcactgtagaccggataa
ggcattatcgccttctccggcaattgaagcctgatgcgacgctgacgcgtcttatcaggcctacgggaccaccaatg
taggtcggataaggcgcaagcgccgcatccgacaagcgatgcctgatgtgacgtttaacgtgtcttatcaggcctac
gggtgaccgacaatgcccggaagcgatacgaaatattcGGTCTACGGTTTAAAAGATAACGATTACTGAAGGATGGA
CAGAACACatgaacttacatgaatatcaggcaaaacaacttttttgcccgctatggcttaccagcaccggtgggttat
gcctgtactactccgcgcgaagcagaagaagccgcttcaaaaatcggtgccggtccgtgggtagtgaaatgtcaggt
tcacgctggtggccgcggtaaagcgggcggtgtgaaagttgtaaacagcaaagaagacatccgtgcttttgcagaaa
actggctgggcaagcgtctggtaacgtatcaaacagatgccaatggccaacggttaaccagattctggttgaagca
gcgaccgatatcgctaaagagctgtatctcggtgccgttgttgaccgtagttcccgtcgtgtggtctttatggcctc
caccgaaggcggcgtggaaatcgaaaaagtggcggaagaaactccgcacctgatccataaagttgcgcttgatccgc
tgactggcccgatgccgtatcagggacgcgagctggcgttcaaactgggtctggaaggtaaactggttcagcagttc
accaaaatcttcatgggcctggcgaccattttcctggagcgcgacctggcgttgatcgaaatcaacccgctggtcat
caccaaacagggcgatctgatttgcctcgacggcaaactgggcgctgacggcaacgcactgttccgccagcctgatc
tgcgcgaaatgcgtgaccagtcgcaggaagatccgcgtgaagcacaggctgcacagtgggaactgaactacgttgcg
ctggacggtaacatcggttgtatggttaacggcgcaggtctggcgatgggtacgatggacatcgttaaactgcacgg
cggcgaaccggctaacttccttgacgttggcggcggcgcaaccaaagaacgtgtaaccgaagcgttcaaaatcatcc
tctctgacgacaaagtgaaagccgttctggttaacatcttcggcggtatcgttcgttgcaacctgatcgctgacggt
atcatcggcgcggtagcagaagtgggtgttaacgtaccggtcgtggtacgtctggaaggtaacaacgccgaactcgg
cgcgaagaaactggctgacagcggcctgaatattattgcagcaaaaggtctgacggatgcagctcagcaggttgttg
ccgcagtggaggggaaataatgtccattttaatcgataaaaacaccaaggttatctgccagggctttaccggtagcc
aggggacttttccactcagaacaggccattgcatacggcactaaaatggttggccgcgtaacccccaggtaaaggcggc
accacccacctcggcctgccggtgttcaacaccgtcgctgaagccgttgctgccactggcgctaccgcttctgttat
ctacgtaccagcaccgtctgcaaagactccattctggaagccatcgacgcaggcatcaaactgattatcaccatca
ctgaaggcatcccgacgctggatatgctgaccgtgaaagtgaagctggatgaagcaggcgttcgtatgatcggcccg
aactgcccaggcgttatcactccgggtgaatgcaaaatcggtatccagcctggtcacattcacaaaccgggtaaagt
gggtatcgtttcccgttccggtacactgacctatgaagcggtaaacaccgcataccgtttcggtcagtcga
cctgtctcggtatcggcggtgacccgatcccgggctctaactttatcgacattctcgaaatgttcgaaaaagatccg
cagaccgaagcgatcgtgatgatcggtgagatcggcggtagcgctgaagaagaagcagctgcgtacatcaaagagca
cgttaccaagccagttgtgggttacatcgctggtgtgactgcgccgaaaggcaaacgtatgggccacgcgggtgcca
tcattgccggtgggaaagggactgcggatgagaaattcgctgctctggaagccgcaggcgtgaaaaccgttcgcagc
ctggcggatatcggtgaagcactgaaaactgttctgaaataaatatctgtaataagaaatagccctcgccgcttccc
tctacaggaatggcgaagggctgtcggtttcgacatggttggccatcgtatgatggcctttttgtgcttatcgcga
tgatttcgctgcgctatcagggtaaattatagtcatcggtattaaaagcgttgcggctatattcaaacacccgac
catcaactaaatatccacgcgatactttttcaagaatcggctttgtctggctgatattaagcagacggctcatctct
tcggttggcatcagaggaatgatttcctgttcgctacgatcgataaccatttctcttcacttcttcgataaagtgata
tttcgaattttccatgacctgccaggtgagatccgggaacaacgcaagcggcatccaggtttcttccagcgccattg
```

Sequences of Interest:

gcttttgcttgcgatagcgcacgcgcttcacatgccacacacgatcctgcggggtgatttgtagctgttgctgaaga
aaatcgtcagccggaatcacttcgaatatcagaacttcactgtgtgtatcgacgtgacggtccgacagtttttcatc
aaaactggttaactgaaaaatatcgtaattgacccgctcttcttgacgtaagtcccgctgccctgaatgctttcga
ggatctgctgctcgactagctggcgcaaagcctgacgcaccgtaacccggctgacgccaaactctgtttgtagcgct
gattcagtgggtaacgcatcgccaggtttaagctcgccacgcgcaatttgttcacgaatgcgatcggcaatctgccg
gtataagggcttgtgtcccattttagtatctcattaatacgaatttaaccattatgcccgataaattcatcctgta
aataatacaaatacaatacaaataatttcaatcaagtgaaattgatcacataatggtattgttttatcg SEQ ID NO: 2. Sequence of the genomic context of *E. coli* BW25113 ΔsucAD.
ccggtcaggcactgactgtgaatgagaaaggcgaagatgtggttgttccgggactgtttgccgttggtgaaatcgct
tgtgtatcggtacacggcgctaaccgtctgggcggcaactcgctgctggacctggtggtcttggtcgcgcggcagg
tctgcatctgcaagagtctatcgccgagcagggcgcactgcgcgatgctgatgttgaagcgtctctgg
atcgcctgaaccgctgaacaataatcgtaacggtgaagatccggtggcgatccgtaaagcgctgcaagaatgtatg
cagcataacttctcggtcttccgtgaaggtgatgcgatggcgaaagggcttgagcagttgaaagtgatccgcgagcg
tctgaaaaatgcccgtctggatgacacttccagcgagttcaacacccagcgcgttgagtgcctggaactggataacc
tgatggaaacggcgtatgcaacggctgtttctgccaacttccgtaccgaaagccgtggcgcgcatagccgcttcgac
ttcccggatcgtgatgatgaaaactggctgtgccactccctgtatctgccagagtcggaatccatgacgcgccgaag
cgtcaacatggaaccgaaactgcgcccggcattcccgccgaagattcgtacttactaatgcggagacaggaaaatga
gactcgagttttcaatttatcgctataacccggatgttgatgatgctccgcgtatgcaggattacaccctggaagcg
gatgaaggtcgcgacatgatgctgctggatgcgcttatccagctaaaagagaaagatcccagcctgtcgttccgccg
ctcctgccgtgaaggtgtgtgcggttccgacggtctgaacatgaacggcaagaatggctcggcctgtattaccccga
tttcggcactcaaccagccgggcaagaagattgtgattcgccgctgccaggtttaccggtgatccgcgatttggtg
gtagacatgggacaattctatgcgcaatatgagaaaattaagcctacctgttgaataatggacaaaatccgccagc
tcgcgagcatttacagatgccagagcagcgcgaaaaactcgacgggcgtgtatgaatgtattctctgcgcatgttgtt
caacctcttgtccgtctttctggtggaatcccgataagtttatcggcccggcaggcttgttagcggcatatcgtttc
ctgattgatagccgtgataccgagactgacagccgcctcgacggtttgagtgatgcattcagcgtattccgctgtca
cagcatcatgaactgcgtcagtgtatgtccgaaggggctgaacccgacgcgcgccatcggccatatcaagtcgatgt
tgttgcaacgtaatgcgtaaaccgtaggcctgataagacgcgcaagcgtcgcatcaggcaaccagtgccggatgcgg
cgtgaacgccttatccggcctacaagtcattacccgtaggcctgataagcgcagcgcatcaggcgtaacaaagaaat
gcaggaaatcttttaaaaactgcccctgacactaagacagtttttaaaggttccttcgcgagccactacgtagacaag
agctcgcaagtgaacccggcacgcacatcactgtgcgtggtagtatccacggcgaagtaagcataaaaaagatgct
taagggatcacgagtgtaggctggagctgcttcgaagttcctatactttctagagaataggaacttcggaataggaa
cttcaagatccccttattagaagaactcgtcaagaaggcgatagaaggcgatgcgctgcgaatcgggagcggcgata
ccgtaaagcacgaggaagcggtcagcccattcgccgccaagctcttcagcaatatcacgggtagccaacgctatgtc
ctgatagcggtccgccacacccagccggccacagtcgatgaatccagaaaagcggccattttccaccatgatattcg
gcaagcaggcatcgccatgggtcacgacgagatcctcgccgtcgggcatgcgcgccttgagcctggcgaacagttcg
gctggcgcgagcccctgatgctcttcgtccagatcatcctgatcgacaagaccggcttccatccgagtacgtgctcg
ctcgatgcgatgtttcgcttggtggtcgaatgggcaggtagccggatcaagcgtatgcagccgccgcattgcatcag
ccatgatggatactttctcggcaggagcaaggtgagatgacaggagatcctgccccggcacttcgcccaatagcagc
cagtccctcccgcttcagtgacaacgtcgagcacagctgcgcaaggaacgcccgtcgtggccagccacgatagccg
cgctgcctcgtcctgcagttcattcagggcaccggacaggtcggtcttgacaaaaagaaccgggccctgcgctg
acagccggaacacggcggcatcagagcagccgattgtctgttgtgcccagtcatagccgaatagcctctccacccaa
gcggccggagaacctgcgtgcaatccatcttgttcaatcatgcgaaacgatcctcatcctgtctcttgatcagatct
tgatcccctgcgccatcagatccttggcggcaagaaagccatccagtttactttgcagggcttcccaaccttaccag
agggcgcccagctggcaattccggttcgcttgctgtccataaaaccgcccagtctagctatcgccatgtaagccca
ctgcaagctacctgctttctctttgcgcttgcgttttcccttgtccagatagcccagtagctgacattcatccgggg
tcagcaccgtttctgcggactggctttctacgtgttccgcttccttagcagccttgcgccctgagtgcttgcggc
agcgtgagcttcaaaagcgctctgaagttcctatactttctagagaataggaacttcgaactgcaggtcgacggatc
cccggaattaattctcatgtttgacagaaaggatacacaatgagtagcgtagatattctggtccctgacctgcctga
atccgtagccgatgccaccgtcgcaacctggcataaaaaacccggcgacgcagtcgtacgtgatgaagtgctggtag
aaatcgaaactgacaaagtggtactggaagtaccggcatcagcgacggcattctggatgcggttctggaagatgaa
ggtacaacggtaacgtctcgtcagatccttggtcgcctgcgtgaaggcaacagcgccggtaaagaaaccagcgccaa
atctgaagagaaagcgtccactccggcgcaacgccagcaggcgtctctggaagagcaaaacaacgatgcgttaagcc
cggcgatccgtcgcctgctggctgaacacaatctcgacgcgcagcgccattaaaggcaccggtgtgggtggtcgtctg
actcgtgaagatgtggaaaaacatctggcgaaagcccggcgaaagagtctgctccggcagcggctgctccggcggc
gcaaccggctctggctgcacgtagtgaaaaacgtgtcccgatgactcgcctgcgtaagcgtgtggcagagcgtctgc
tggaagcgaaaaactccaccgccatgctgaccacgttcaacgaagtcaacatgaagcgattatggatctgcgtaag
cagtacggtgaagcgtttgaaaaacgcacggcatccgtctgggctttatgtccttctacgtgaaagcggtggttga
agccctgaaacgttacccggaagtgaacgcttctatcgacgcgatgacgtggtttaccacaactatttcgacgtca
gcatggcggtttctacgccgcgcggcctggtgacgccggttctgcgtgatgtcgatccctcggcatggcagacatc
gagaagaaaatcaaagagctggcagtcaaaggccgtgacggcaagctgaccgttgaagatctgaccggtggtaactt
caccatcaccaacggtggtgtgttcggttcctgatgtctacgccgatactcaacccgccgcagagcgcaattctgg
gtatgcacgctatcaaagatcgtccgatggcggtgaatgtcaggttgagatcctgccgatgatgtacctggcgctg
tcctacgatcaccgtctgatcgatggtcgcgaatccgtgggcttcctggtaacgatcaaagagttgctgaagatcc
gacgcgtctgctgctggacgtgtagtagtttaagtttcacctgcactgtagaccggataaggcattatcgccttctc
cggcaattgaagcctgatgcgacgctgacgcgtcttatcaggcctacgggaccaccaatgtaggtcggataaggcgc
aagcgccgcatccgacaagcgatgcctgatgtgacgtttaacgtgctttatcaggcctacgggtgaccgacaatgcc
cggaagcgatacgaaatattcggtctacggtttaaaagataacgattactgaaggatggacagaacacatgaactta
catgaatatcaggcaaaacaacttttttgcccgctatggcttaccagcaccggtgggttatgcctgtactactccgcg
cgaagcagaagaagccgcttcaaaaatcggtgccggtccgtgggtagtgaaatgtcaggttcacgctggtggccgcg
gtaaagcgggcggtgtgaaagttgtaaacagcaaagaagacatccgtgcttttgcagaaaactggctgggcaagcgt
ctggtaacgtatcaaacagatgccaaccggttaaccagattctggttgaagcagcgaccgatatcgctaa
agagctgtatctcggtgccgttgttgaccgtagttcccgtcgtgtggctcttatggcctccaccgaaggcggcgtgg
aaatcgaaaagtggcggaagaaactccgcacctgatccataaagttgcgcttgatccgctgactggcccgatgccg
tatcagggacgcgagctggcgttcaaactgggtctggaaggtaaactggttcagcagttcaccaaaaatcttcatggg
cctggcgaccattttcctggagcgcgacctggcgttgatcgaaatcaacccgctggtcatcaccaaacagggcgatc
tgatttgcctcgacggcaaactgggcgctgacggcaacgcactgttccgccagcctgatctgcgcgaaatgcgtgac -continued Sequences of Interest:

cagtcgcaggaagatccgcgtgaagcacaggctgcacagtgggaactgaactacgttgcgctggacggtaacatcgg
ttgtatggttaacggcgcaggtctggcgatgggtacgatggacatcgttaaactgcacggcggcgaaccggctaact
tccttgacgttggcggcggcgcaaccaaagaacgtgtaaccgaagcgttcaaaatcatcctctctgacgacaaagtg
aaagccgttctggttaacatcttcggcggtatcgttcgttgcgacctgatcgctgacggtatcatcggcgcggtagc
agaagtgggtgttaacgtaccggtcgtggtacgtctggaaggtaacaacgccgaactcggcgcgaagaaactggctg
acagcggcctgaatattattgcagcaaaaggtctgacggatgcagctcagcaggttgttgccgcagtggaggggaaa
taatgATTCCGGGGATCCGTCGACCTGCAGTTCGAAGTTCCTATCTAGAAAGTATAGGAACTTCGAAGCAGCTCCAG
CCTACActgaaaactgttctgaaataaatatctgtaataagaaatagccctcgccgcttccctctacaggaatggcg
aagggctgtcggtttcgacatggttggccatcgtatgatggccttttttgtgcttatcgcgatgattttcgctgcgc
tatcagggtaaatttatagtcatcggtattaaaagcgttgcggctatattcaaacacccgaccatcaactaaatatc
cacgcgatacttttttcaagaatcggctttgtctggctgatattaagcagacggctcatctcttcggttggcatcaga
ggaatgatttcctgttcgctacgatcgataaccattttcttcacttcttcgataaagtgatatttcgaattttccat
gacctgccaggtgagatccgggaacaacgcaagcggcatccaggtttcttccagcgccattggcttttgcttgcgat
agcgcacgcgcttcacatgccacacacgatcctgcggggtgatttgtagctgttgctgaagaaaatcgtcagccgga
atcacttcgaatatcagaacttcactgtgtgtatcgacgtgacggtccgacagtttttcatcaaaactggttaactg
aaaaatatcgtaattgacccgctcttctttgacgtaagtcccgctgccctgaatgctttcgaggatctgctgctcga
ctagctggcgcaaagcctgacgcaccgtaacccggctgacgccaaactctgtttgtagcgctgattcagtgggtaac
gcatcgccaggtttaagctcgccacgcgcaatttgttcacgaatgcgatcggcaatctgccggtataagggcttgtg
tcccattttagtatctcattaatacgaatttaaccattatgcccgataaattcatcctgtaaataatacaaataca
atacaaataatttcaatcaagtgaaattgatcacataatggtattgttttatcg SEQ ID NO: 3. Sequence of the genomic context of E. coli BW25113 ΔsucABCD
ccggtcaggcactgactgtgaatgagaaaggcgaagatgtggttgttccgggactgtttgccgttggtgaaatcgct
tgtgtatcggtacacggcgctaaccgtctgggcggcaactccgctggacctggtggtcttttggtcgcggcagg
tctgcatctgcaagagtctatcgccgagcagggcgcactgcgcgatgccagcgagtctgatgttgaagcgtctctgg
atcgcctgaaccgctggaacaataatcgtaacggtgaagatccggtggcgatccgtaaagcgctgcaagaatgtatg
cagcataacttctcggtcttccgtgaaggtgatgcgatggcgaaagggcttgagcagttgaaagtgatccgcgagcg
tctgaaaaatgcccgtctggatgacacttccagcgagttcaacaccagcgcgttgagtgcctggaactggataacc
tgatggaaacggcgtatgcaacggctgtttctgccaacttccgtaccgaaagccgtggcgcgcatagccgcttcgac
ttcccggatcgtgatgatgaaaactggctgtgccactccctgtatctgccagagtcggaatccatgacgcgccgaag
cgtcaacatggaaccgaaactgcgcccggcattcccgccgaagattcgtacttactaatgcggagacaggaaaatga
gactcgagttttcaatttatcgctataacccggatgttgatgatgctccgcgtatgcaggattacaccctggaagcg
gatgaaggtcgcgacatgatgctgctggatgcgcttatccagctaaaagagaaagatcccagcctgtcgttccgccg
ctcctgccgtgaaggtgtgtgcggttccgacggtctgaacatgaacggcaagaatggctgcctgtattacccccga
tttcggcactcaaccagccgggcaagaagattgtgattcgcccgctgccaggtttaccggtgatccgcgatttggtg
gtagacatgggacaattctatgcgcaatatgagaaaattaagcctacctgttgaataatggacaaaatccgccagc
tcgcgagcatttacagatgccagagcagcgcgaaaaactcgacgggctgtatgaatgtattctctgcgcatgttgtt
caacctcttgtccgtctttctggtggaatcccgataagtttatcggcccggcaggcttgttagcggcatatcgtttc
ctgattgatagccgtgataccgagactgacagccgcctcgacggtttgagtgatgcattcagcgtattccgctgtca
cagcatcatgaactgcgtcagtgtatgtccgaaggggctgaacccgacgcgcgccatcggccatatcaagtcgatgt
tgttgcaacgtaatgcgtaaaccgtaggcctgataagacgcgcaagcgtcgcatcaggcacctcgcactcagtgccggatgcgg
cgtgaacgccttatccggcctacaagtcattacccgtaggcctgataagcgcagcgcatcaggcgtaacaaagaaat
gcaggaaatcttttaaaaactgcccctgacactaagacagttttaaaggttccttcgcgagccactacgtagacaag
agctcgcaagtgaaccccggcacgcacatcactgtgcgtggtagtatccacggcgaagtaagcataaaaaagatgAT
TCCGGGGATCCGTCGACCTGCAGTTCGAAGTTCCTATCTAGAAAGTATAGGAACTTCGAAGCAGCTCCAGCCTACAc
tgaaaactgttctgaaataaatatctgtaataagaaatagccctcgccgcttccctctacaggaatggcgaagggct
gtcggtttcgacatggttggccatcgtatgatggccttttttgtgcttatcgcgatgattttcgctgcgctatcagg
gtaaatttatagtcatcggtattaaaagcgttgcggctatattcaaacacccgaccatcaactaaatatccacgcga
tacttttttcaagaatcggctttgtctggctgatattaagcagacggctcatctcttcggttggcatcagaggaatga
tttcctgttcgctacgatcgataaccattttcttcacttcttcgataaagtgatatttcgaattttccatgacctgc
caggtgagatccgggaacaacgcaagcggcatccaggtttcttccagcgccattggcttttgcttgcgatagcgcac
gcgcttcacatgccacacacgatcctgcggggtgatttgtagctgttgctgaagaaaatcgtcagccggaatcactt
cgaatatcagaacttcactgtgtgtatcgacgtgacggtccgacagtttttcatcaaaactggttaactgaaaaata
tcgtaattgacccgctcttctttgacgtaagtcccgctgccctgaatgctttcgaggatctgctgctcgactagctg
gcgcaaagcctgacgcaccgtaacccggctgacgccaaactctgtttgtagcgctgattcagtgggtaacgcatcgc
caggtttaagctcgccacgcgcaatttgttcacgaatgcgatcggcaatctgccggtataagggcttgtgtcccatt
tttagtatctcattaatacgaatttaaccattatgcccgataaattcatcctgtaaataatacaaatacaatacaaa
taatttcaatcaagtgaaattgatcacataatggtattgttttatcg SEQ ID NO: 4. Sequence of Plasmid pDVK-SucAD, used for testing plasmid retention
in nonselective media
ccacccatctgggtttgccggtatttaataccgtgcgtgaggcggttgccgcaaccggtgccacggcttcagttatc
tatgttcctgccccatttgtaaagattcaattctggaagctattgatgcgggcatcaaattgattattacgattac
cgaaggtatccctacgctggatatgttgacggttaaagtgaaacttgatgaagcgggggtacgcatgattggtccga
attgtccgggcgttattactccaggtgagtgcaaaattggtattcagccgggtcatattcacaaacctgggaaagtc
ggaattgtgtctcgttctggcactctgacgtatgaggcagttaaacagaccacagattatggctttgggcagagtac
ctgtgtcggcatcggaggcgatcctattccggggagtaattttatcgatattctggaaatgtttgagaaagatccgc
agaccgaggcaatcgtcatgattggcgagattggcggttccgcggaagaagaagctgcagcctatatcaaagaacat
gtcacaaaaccggtagtgggctatatcgcggggagtcacggccccaaaaggtaaacgtatgggccatgccggagcgat
catcgcgggcggcaaaggcactgcagatgaaaaatttgcagcccttgaggccgctggcgtaaaaacggtccgttccc
ttgctgatattggtgaagcactgaaaccgtgttgaaataaAGGTccaggcatcaaatcaaaacgaaaggctcagtcg
aaagactgggccttttcgttttatctgtttggtcggtgaacgctctctactagagtcacactggtctcaccttcggg
tgggcctttctgcgtttatatgccatgtcttctactagtagcggccgctgcagtccggcaaaaaagggcaaggtgtc
accaccctgcccttttttcttttaaaaccgaaaagattacttcgcgttatgcaggcttcctcgctcactgactcgctgc
gctcggtcgttcggctgcggcgagcggtatcagctcactcaaaggcggtaatacggttatccacagaatcagggat
aacgcaggaaagaacatgtgagcaaaaggccagcaaaaggccaggaaccgtaaaaaggccgcgttgctggcgtttttt
ccacaggctccgcccccctgacgagcatcacaaaaatcgacgctcaagtcagaggtggcgaaacccgacaggactat

Sequences of Interest:

```
aaagataccaggcgtttccccctggaagctccctcgtgcgctctcctgttccgaccctgccgcttaccggatacctg
tccgcctttctcccttcggaagcgtggcgctttctcatagctcacgctgtaggtatctcagttcggtgtaggtcgt
tcgctccaagctgggctgtgtgcacgaaccccccgttcagcccgaccgctgcgccttatccggtaactatcgtcttg
agtccaacccggtaagacacgacttatcgccactggcagcagccactggtaacaggattagcagagcgaggtatgta
ggcggtgctacagagttcttgaagtggtggcctaactacggctacactagaagaacagtatttggtatctgcgctct
gctgaagccagttaccttcggaaaaagagttggtagctcttgatccggcaaacaaaccaccgctggtagcggtggtt
ttttgtttgcaagcagcagattacgcgcagaaaaaaaggatctcaagaagatcctttgatcttttctacggggtct
gacgctcagtggaacgaaaactcacgttaagggattttggtcatgagattatcaaaaaggatcttcacctagatcct
tttaaattaaaaatgaagttttaaatcaatctaaagtatatatgagtaaacttggtctgacagctcgagtcccgtca
agtcagcgtaatgctctgccagtgttacaaccaattaaccaattctgattagaaaaactcatcgagcatcaaatgaa
actgcaatttattcatatcaggattatcaataccatattttgaaaaagccgtttctgtaatgaaggagaaaactca
ccgaggcagttccataggatggcaagatcctggtatcggtctgcgattccgactcgtccaacatcaatacaacctat
taatttcccctcgtcaaaaataaggttatcaagtgagaaatcaccatgagtgacgactgaatccggtgagaatggca
aaagcttatgcatttctttccagacttgttcaacaggccagccattacgctcgtcatcaaaatcactcgcatcaacc
aaaccgttattcattcgtgattgcgcctgagcgagacgaaatacgcgatcgctgttaaaaggacaattacaaacagg
aatcgaatgcaaccggcgcaggaacactgccagcgcatcaacaatattttcacctgaatcaggatattcttctaata
cctggaatgctgttttcccggggatcgcagtggtgagtaaccatgcatcatcaggagtacggataaaatgcttgatg
gtcggaagaggcataaattccgtcagccagtttagtctgaccatctcatctgtaacatcattggcaacgctacctt
gccatgtttcagaaacaactctggcgcatcgggcttcccatacaatcgatagattgtcgcacctgattgcccgacat
tatcgcgagcccatttataccatataaatcagcatccatgttgaattaatcgcggcctggagcaagacgtttcc
cgttgaatatggctcataacacccccttgtattactgtttatgtaagcagacagttttattgttcatgatgatatatt
tttatcttgtgcaatgtaacatcgagattttgagacacaacgtggctttgttgaataaatcgaacttttgctgagt
tgaaggatcagctcgagtgccacctgacgtctaagaaaccattattatcatgacattaacctataaaaataggcgta
tcacgaggcagaatttcagataaaaaaaatcctttagctttcgctaaggatgatttctgaattcgcggcgcttcta
gagactagtggaagacatCGCTtgacagctagctcagtcctaggtactgtgctagcTACTttaaactccccgagca
atagtaatgcagaactcagcattgaaagcatggcttgatagctcctatttatcaggtgctaaccagagctggattga
acagctgtatgaagattttctgacagatccggattcagtggatgcgaattggcgcagcacttttcagcagttgcctg
gcaccggtgtaaaaccggatcagtttcattcccagacgcgggagtattttcgtcgtctggcgaaagatgcgagccgg
tattcaagtacaatttctgatccggatacgaatgtaaaacaggtgaaagtgcttcagttaattaatgcgtatcgctt
tagaggccatcagcatgcgaatctggatccgctgggcttatggcagcaggataaagtcgcggatctggatccaagtt
ttcacgatttaacggaagctgattttcaggaaacctttaacgtcggctcattcgcaagtgggaaagaaacaatgaaa
ctgggcgaacttcttgaggcgctgaaacagacttattgtggccctattggtgcggaatatatgcatattacctcaac
tgaagagaaacgttggattcagcagagaatcgagagtggccgcgcgacttttaactccgaagaaaaaaaagattcc
tgtcagaactgacagccgcggaaggcttagagcggtatttgggtgccaaattcccaggagcaaaacggttcagcctg
gagggcggtgatgcgctgatcccgatgctgaaagaaatgattcggcatgcgggaaatagcggaactcgggaagtggt
gttaggaatggcacaccgcggccgtttgaatgtactggttaacgtattaggaaaaaaacctcaggatttattgatg
agttcgcgggaaaacataaagaacatctgggcactggtgatgtcaaatatcacatgggcttctcaagtgattttcag
acggatggaggtctggttcacctggcactggcatttaatcctctctcatctggaaatcgtaagtccggtcgttattgg
ttccgtgcgcgctcgcttagatcggttagatgaacctagctcaaacaaagttttaccaatcacgatccatgggatg
cagctgttaccggacagggtgttgtgcaggagactttgaatatgtccaaagcgcgcgggtatgaggtgggtggtacg
gtgcgtattgttatcaataatcaggtgggttttacaaccagtaaccctctggatgctcgctctacgccgtattgcac
tgatattggtaaaatggtgcaggcaccaattttttcacgtcaatgccgatgatccggaagctgttgcctttgttacgc
gcctggctctggattttcgtaacacttttcaaacgtgatgtatttatcgatttagtatgctatcgtcgtcatggtcat
aatgaggctgatgaacctagcgctacccagccactgatgtatcagaaaattaaaaaacatcctaccccctcgtaaaat
ttatgcggataaactggagcaggaaaaagtggctactcttgaagatgctactgaaatggtcaatcttatcgggatg
cattggatgcgggtgattgcgtggtcgcggaatggcgcccgatgaatatgcattcatttacttggtcaccgtattta
aatcatgagtgggatgaggaatatccgaataaagtggagatgaaacgcctgcaggaattagcaaaacgtattagcac
agtacctgaagcggttgagatgcagtctagagttgccaaaatctatggagatcgccaggccatggcagcaggggaaa
aacttttgattgggggggagccgaaaacctggcatatgcgacgctggtagatgaggcattccggtgcgccttctct
ggtgaagattctgggcgcggtacttttttttcatcggcacgctgttattcataaccagtctaacggtagtacttatac
tccgctgcagcacatccacaatggtcagggtgcgttccgtgtatgggattccgtgctgagtgaagaagcggttcttg
cgtttgagtatgggtatgcaactgccgagccacgcacgctgacgatctgggaagcccagtttggcgattttgcaaat
ggtgcccaggtggtaatcgatcagtttattagctccggcgaacagaaatggggggcggatgtgtggtttagttatgtt
gttaccgcatggctatgaaggtcagggacctgagcacagctcagcgcgcctggaacgctatcttcagctgtgtgcgg
aacagaacatgcaggtatgcgttccttccacgccggctcaggtttatcatatgttaagacgtcaggccttgcgcggt
atgcggcgcccgttggtcgtgatgtccccgaaaagtttactgcgccatccgttagcagttagcagcctggaggaact
ggcaaacggtacgttcttgccagctatccggcgaaatcgatgaactggatcctcaaagggggtgaaacgcgttgttatgt
gttctgtaaagtgtattatgatctttttggaacagcgtcgcaaaaataatcagcacgatgtagctattgtgcggatc
gagcagctgtatccgttcccgcacaaagcaatgcaggaagtgctgcagcagttcgcacatgtcaaagatttttgtctg
gtgtcaggaggaaccgcttaatcagggggcctggtattgtagtcagcaccatttccgggaggtgatcccgtttgggg
cgtccttacggtatgctggtcgccctgcctccgcaagtccggccgtgggatatatgagcgttcaccagaaacagcag
caggatttggtgaatgatgctttgaatgtggaatgaatgtccatcctgatcgacaaaaacactaaagtaatttgtca
gggctttaccggttcccagggcacatttcactcagagcaggccatcgcttatgggaccaaaatggtgggtggtgtaa
cgcctggtaaaggaggca
```

SEQ ID NO: 5. Sequence of Plasmid pDVK-SucABCD, used for testing plasmid retention in nonselective media

```
ccggcgaaagagtctgctccggcagcggctgctccggcggcgcaaccggctctggctgcacgtagtgaaaaacgtgt
cccgatgactcgcctgcgtaagcgtgtggcagagcgtctgctggaagcgaaaaactccaccgccatgctgaccacgt
tcaacgaagtcaacatgaagccgattatggatctgcgtaagcagtacggtgaagcgtttgaaaaacgccacggcatc
cgtctgggctttatgtccttctacgtgaaagcggtggttgaagccctgaaacgttaccggaagtgaacgcttctat
cgacggcgatgacgtggtttaccacaactatttcgacgtcagcatggccggtttctacgccggcgggcctggtgacgc
cggttctgcgtgatgtcgatacccccggcatggcagacatcgagaagaaaatcaaagagctggcagtcaaaggccgt
gacggcaagctgaccgttgaagatctgaccggtggtaacttccaccatcaccaacggtggtgtgttcggttccctgat
gtctacgccgatcatcaacccgccgcagagcgcaattctgggtatgcacgctatcaaagatcgtccgatggcggtga
atggtcaggttgagatcctgccgatgatgtacctggcgctgtcctacgatcaccgtctgatcgatggtcgcgaatcc
gtgggcttcctggtaacgatcaaagagttgctggaagatccgacgcgtctgctgctggacgtgtagtagtttaagtt
```

Sequences of Interest:

```
tcacctgcactgtagaccggataaggcattatcgccttctccggcaattgaagcctgatgcgacgctgacgcgtctt
atcaggcctacgggaccaccaatgtaggtcggataaggcgcaagcgccgcatccgacaagcgatgcctgatgtgacg
tttaacgtgtcttatcaggcctacgggtgaccgacaatgcccggaagcgatacgaaatattcGGTCTACGGTTTAAA
AGATAACGATTACTGAAGGATGGACAGAACACatgaacttacatgaatatcaggcaaaacaactttttgcccgctat
ggcttaccagcaccggtgggttatgcctgtactactccgcgcgaagcagaagaagccgcttcaaaaatcggtgccgg
tccgtgggtagtgaaatgtcaggttcacgctggtggccgcggtaaagcgggcggtgtgaaagttgtaaacagcaaaG
AGgacatccgtgcttttgcagaaaactggctgggcaagcgtctggtaacgtatcaaacagatgccaatggccaaccg
gttaaccagattctggttgaagcagcgaccgatatcgctaaagagctgtatctcggtgccgttgttgaccgtagttc
ccgtcgtgtggtctttatggcctccaccgaaggcggcgtggaaatcgaaaaagtggcggaagaaactccgcacctga
tccataaagttgcgcttgatccgctgactgggcccgatgccgtatcagggacgcgagctggcgttcaaactgggtctg
gaaggtaaactggttcagcagttcaccaaaatcttcatgggcctggcgaccattttcctggagcgcgacctggcgtt
gatcgaaatcaacccgctggtcatcaccaaacagggcgatctgatttgcctcgacggcaaactgggcgctgacggca
acgcactgttccgccagcctgatctgcgcgaaatgcgtgaccagtcgcaggaagatccgcgtgaagcacaggctgca
cagtgggaactgaactacgttgcgctggacggtaacatcggttgtatggttaacggcgcaggtctggcgatgggtac
gatggacatcgttaaactgcacggcggcgaaccggctaacttccttgacgttggcggcggcgcaaccaaagaacgtg
taaccgaagcgttcaaaatcatcctctctgacgacaaagtgaaagccgttctggttaacatcttcggcggtatcgtt
cgttgcgacctgatcgctgacggtatcatcggcgcggtagcagaagtgggtgttaacgtaccggtcgtggtacgtct
ggaaggtaacaacgccgaactcggcgcgaagaaactggctgacagcggcctgaatattattgcagcaaaaggtctga
cggatgcagctcagcaggttgttgccgcagtggagggaaataatgtccatttttaatcgataaaaacaccaaggtta
tctgccagggctttaccggtagccaggggacttttccactcagaacaggccattgcataccggcactaaaatggttggc
ggcgtaaccccaggtaaaggcggcaccaccccacctcggcctgccggtgttcaacaccgtgcgtgaagccgttgctgc
cactggcgctaccgcttctgttatctacgtaccagcaccgttctgcaaagactccattctggaagccatcgacgcag
gcatcaaactgattatcaccatcactgaaggcatcccgacgctggatatgctgaccgtgaaagtgaagctggatgaa
gcaggcgttcgtatgatcggcccgaactgcccaggcgttatcactccgggtgaatgcaaaatcggtatccagcctgg
tcacattcacaaaccgggtaaagtgggtatcgtttcccgttccggtcacactgacctatgaagcggttaaacagacca
cggattacggtttcggtcagtcgacctgtgtcggtatcggcggtgacccgatcccgggctctaactttatcgacatt
ctcgaaatgttcgaaaaagatccgcagaccgaagcgatcgtgatgatcggtgagatcggcggtagcgctgaagaaga
agcagctgcgtacatcaaagagcacgttaccaagccagttgtgggttacatcgctggtgtgactgcgccgaaaggca
aacgtatgggccacgcgggtgccatcattgccgtgggaaaggggactgcggatgagaaattcgctgctctggaagcc
gcaggcgtgaaaaccgttcgcagcctggcggatatcggtgaagcactgaaaactgttctgaaataaaggtccaggca
tcaaataaaacgaaaggctcagtcgaaagactgggcctttcgttttatctgttgtttgtcggtgaacgctctctact
agagtcacactggctcaccttcgggtgggcctttctgcgtttatatgccatgtcttctactagtagcggccgctgca
gtccggcaaaaaagggcaaggtgtcaccacctgcccttttcttttaaaaccgaaaagattacttcgcgttatgcag
gcttcctcgctcactgactcgctgcgctcggtcgttcggctgcggcgagcggtatcagctcactcaaaggcggtaat
acggttatccacagaatcaggggataacgcaggaaagaacatgtgagcaaaaggccagcaaaaggccaggaaccgta
aaaaggccgcgttgctggcgtttttccacaggctccgcccccctgacgagcatcacaaaaatcgacgctcaagtcag
aggtggcgaaacccgacaggactataaagataccaggcgtttccccctggaagctccctcgtgcgctctcctgttcc
gaccctgccgcttaccggatacctgtccgcctttctcccttcgggaagcgtggcgctttctcatagctcacgctgta
ggtatctcagttcggtgtaggtcgttcgctccaagctgggctgtgtgcacgaaccccccgttcagcccgaccgctgc
gccttatccggtaactatcgtcttgagtccaacccggtaagacacgacttatcgccactggcagcagccactggtaa
caggattagcagagcgaggtatgtaggcggtgctacagagttcttgaagtggtggcctaactacggctacactagaa
gaacagtatttggtatctgcgctctgctgaagccagttaccttcggaaaaagagttggtagctcttgatccggcaaa
caaaccaccgctggtagcggtggtttttttgtttgcaagcagcagattacgcgcagaaaaaaaggatctcaagaaga
tcctttgatcttttctacggggtctgacgctcagtggaacgaaaactcacgttaagggattttggtcatgagattat
caaaaaggatcttcacctagatcctttttaaattaaaaatgaagttttaaatcaatctaaagtatatatgagtaaact
tggtctgacagctcgagtcccgtcaagtcagcgtaatgctctgccagtgttacaaccaattaaccaattctgattag
aaaaactcatcgagcatcaaatgaaactgcaatttattcatatcaggattatcaataccatattttgaaaaagccg
tttctgtaatgaaggagaaaactcaccgaggcagttccataggatggcaagatcctggtatcggtctgcgattccga
ctcgtccaacatcaatacaacctattaatttcccctcgtcaaaaataaggttatcaagtgagaaatcaccatgagtg
acgactgaatccgtgagaatggcaaaagcttatgcatttctttccagacttgttcaacaggccagccattacgctc
gtcatcaaaatcactcgcatcaaccaaaccgttattcattcgtgattgcgcctgagcgagacgaaatacgcgatcgc
tgttaaaggacaattacaaacaggaatcgaatgcaaccggcgcaggaacactgccagcgcatcaacaatatttcac
cctgaatcaggatattcttctaatacctggaatgctgtttttccccggggatcgcagtggtgagtaaccatgcatc
aggagtacggataaaatgcttgatggtcggaagaggcataaattccgtcagccagtttagtctgaccatctcatctg
taacatcattggcaacgctacctttgccatgtttcagaaacaactctggcgcatcgggcttcccatacaatcgatag
attgtcgcacctgattgcccgacattatcgcgagcccatttatacccatataaatcagcatccatgttgaatttaa
tcgcggcctggagcaagacgtttcccgttgaatatggctcataacaccccttgtattactgtttatgtaagcagaca
gttttattgttcatgatgatatatttttatcttgtgcaatgtaacatcagagattttgagacacaacgtggctttgt
tgaataaatcgaacttttgctgagttgaaggatcagctcgagtgccacctgacgtctaagaaaccattattatcatg
acattaacctataaaaataggcgtatcacgaggcagaatttcagataaaaaaatccttagctttcgctaaggatga
tttctggaattcgcggccgcttctagagactagtggaagacatcgctaccgtaggcctgataagacgcgcaagcgtc
gcatcaggcaaccagtgccggatgcggcgtgaacgccttatccggcctacaagtcattacccgtaggcctgataagc
gcagcgcatcaggcgtaacaaagaaatgcaggaaatctttaaaaactgcccctgacactaagacagttttttaaggt
tccttcgcgagccactacgtagacaagagctcgcaagtgaacccccggcacgcacatcactgtgcgtggtagtatcca
cggcgaagtaagcataaaaaagatgcttaagggatcacgAATGcagaacagcgctttgaaagcctggttggactctt
cttacctctctggcgcaaaccagagctggatagaacagctctatgaaGATttcttaaccgatcctgactcggttgac
gctaactggcgttcgacgttcgacgttaccggtacggagcgtcaactcaatcctcaaacgcgtga
atatttccgccgcctggcgaaagacgcttcacgttactccttcaacgatctccgaccctgacaccaatgtgaagcagg
ttaaagtcctgcagctcattaacgcataccgcttccgtggtcaccagcatgcgaatctcgatccgctgggactgtgg
cagcaagataaagtggccgatctggatccgtctttccacgatctgaccgaagcagacttccaggagACTttcaacgt
cggttcatttgccagcggcaaagaaaccatgaaactcggcgagctgctggaagccctcaagcaaacctactgcggcc
cgattggtgccgagtatatgcacattaccagcaccgaagaaaaacgctggatccaacagcgtatcgagtctggtcgc
gcgactttcaatagcgaagagaaaaaacgcttcttaagcgaactgaccgccgctgaaggtcttgaacgttacctcgg
cgcaaaattccctggcgcaaaacgcttctcgctggaaggcggtgacgcgttaatcccgatgcttaaagagatgatcc
gccacgctggcaacagcggcacccgcgaagtggttctcgggatggcgcaccgtggtcgtctgaacgtgctggtgaac
gtgctgggtaaaaaaccgcaagacttgttcgacgagttcgccggtaaacataaagaacacctcggcacgggtgacgt
gaaataccacatgggcttctcgtctgacttccagaccgatggcggcctggtgcacctggcgctggcgtttaacccgt
```

-continued

Sequences of Interest:

ctcaccttgagattgtaagcccggtagttatcggttctgttcgtgcccgtctggacagacttgatgagccgagcagc
aacaaagtgctgccaatcaccatccacggtgacgccgcagtgaccgggcagggcgtggttcaggaaaccctgaacat
gtcgaaagcgcgtggttatgaagttggcggtacggtacgtatcgttatcaacaaccaggttggtttcaccacctcta
atccgctggatgcccgttctacgccgtactgtactgatatcggtaagatggttcaggccccgattttccacgttaac
gcggacgatccggaagccgttgcctttgtgacccgtctggcgctcgatttccgtaacacctttaaacgtgatGTTtt
catcgacctggtgtgctaccgccgtcacggccacaacgaagccgacgagccgagcgcaacccagccgctgatgtatc
agaaaatcaaaaaacatccgacaccgcgcaaaatctacgctgacaagctggagcaggaaaaagtggcgacgctggaa
gatgccaccgagatggttaacctgtaccgcgatgcgctggatgctggcgattgcgtagtggcagagtggcgtccgat
gaacatgcactctttcacctggtcgccgtacctcaaccacgaatgggacgaagagtacccgaacaaagttgagatga
agcgcctgcaggagctggcgaaacgcatcagcacggtgccggaagcagttgaaatgcagtctcgcgttgccaagatt
tatggcgatcgccaggcgatggctgccggtgagaaactgttcgactggggcggtgcggaaaaacctcgcttacgccac
gctggttgatgaaggcattccggttcgcctgtcgggtGAGgactccggtccggtcgggtaccttcttccaccgccacgcgg
tgatccacaaccagtctaacggttccacttacacgccgctgcaacatatccataacgggcagggcgcgttccgtgtc
tgggactccgtactgtctgaagaagcagtgctggcgtttgaatatggttatgccaccgcagaaccacgcactctgac
catctgggaagcgcagttcggtgacttcgccaacggtgcgcaggtggttatcgaccagttcatctcctctggcgaac
agaaatggggccggatgtgtggtctggtgatgttgctgccgcacggttacgaagggcagggggccggagcactcctcc
gcgcgtctggaacgttatctgcaactttgtgctgagcaaaacatgcaggtttgcgtaccgtctaccccggcacaggt
ttaccacatgctgcgtcgtcaggcgctgcgcgggatgcgtcgtccgctggtcgtgatgtcgccgaaatccctgctgc
gtcatccgctggcggtttccagcctcgaagaactggcgaacggcaccttcctgccagccatcggtgaaatcgacgag
cttgatccgaagggcgtgaagcgctagtgatgtgttctggtaaggtttattacgacctgctggaacagcgtcgtaa
gaacaatcaacacgatgtcgccattgtgcgtatcgagcaactctacccgttcccgcataaagcgatgcaggaagtgt
tgcagcagtttgctcacgtcaaggattttgtctggtgccaggaagagccgctcaaccagggcgcatggtactgcagc
cagcatcatttccgtgaagtgattccgtttggggcttctctgcgttatgcaggccgcccggcctccgcctctccggc
ggtagggtatatgtccgttcaccagaaacagcaacaagatctggttaatgacgcgctgaacgtcgaataaataaagg
atacacaatgagtagcgtagatattctggtccctgacctgcctgaatcctgagccgatgccaccgtcgcaacctggc
ataaaaaacccggcgacgcagtcgtacgtgatgaagtgctggtagaaatcgaaactgacaaagtggtactggaagta
ccggcatcagcagacggcattctggatgcggttctggaagatgaaggtacaacggtaacgtctcgtcagatccttgg
tcgcctgcgtgaaggcaacagcgccggtaaagaaaccagcgccaaatctgaagaaagcgtccactccggcgcaac
gccagcaggcgtctctggaagagcaaaacaacgatgcgttaagcccggcgatccgtcgcctgctggctgaacacaat
ctcgacgccagcgccattaaaggcaccggtgtgggtggtcgtctgactcgtgaagatgtgaaaaacatctggcgaa
agcc SEQ ID NO: 6. Sequence of the pDvS vector, designed for facile cloning with a
modular cloning system. It contains the sucAD gene pair instead of an antibiotic
resistance marker.
cgcgttgctggcgttttccacaggctccgccccctgacgagcatcacaaaaatcgacgctcaagtcagaggtggc
gaaacccgacaggactataaagataccaggcgtttccccctggaagctccctcgtgcgctctcctgttccgaccctg
ccgcttaccggatacctgtccgcctttctcccttcgggaagcgtggcgctttctcatagctcacgctgtaggtatct
cagttcggtgtaggtcgttcgctccaagctgggctgtgtgcacgaaccccccgttcagcccgaccgctgcgccttat
ccggtaactatcgtcttgagtccaacccggtaagacacgacttatcgccactggcagcagccactggtaacaggatt
agcagagcgaggtatgtaggcggtgctacagagttcttgaagtggtggcctaactacggctacactagaagaacagt
atttggtatctgcgctctgctgaagccagttaccttcggaaaaagagttggtagctcttgatccggcaaacaaacca
ccgctggtagcggtggtttttttgtttgcaagcagcagattacgcgcagaaaaaaaggatctcaagaagatcctttg
atcttttctacggggtctgacgctcagtggaacgaaaactcacgttaagggattttggtcatgagattatcaaaaag
gatcttcacctagatccttttaaattaaaaatgaagttttaaatcaatctaaagtatatatgagtaaaacttggtctg
acagctcgagtttacggctagctcagtcctaggtatagtgctagcTACTtgttagaaaagagaagcacgtaatgcag
aactcagcattgaaagcatggcttgatagctcctatttatcaggtgctaaccagagctggattgaacagctgtatga
agatttctgacagatccggattcagtggatgcgaattggcgcagcacttttcagcagttgcctggcaccggtgtaa
aaccggatcagtttcattcccagacgcgggagtattttcgtcgtctggcgaaagatgcgagccggtattcaagtaca
atttctgatccggatacgaatgtaaaacaggtgaaagtgcttcagttaattaatgcgtatcgctttagaggccatca
gcatgcgaatctggatccgctgggcttatggcagcaggataaagtcgcggatctggatccaagttttcacgattta
cggaagctgattttcaggaaacctttaacgtcggctcattcgcaagtgggaaagaaacaatgaaactgggcgaactt
cttgaggcgctgaaacagacttattgtgcccattggtgcggaaatatgcatattacctcaactgaagagaaacg
ttggattcagcagagaatcgagagtggccgcgcgacttttaactccgaagaaaaaaaaagattcctgtcagaactga
cagccgcggaaggcttagagcggtatttgggtgccaaattcccaggagcaaaacggttcagcctggagggcggtgat
gcgctgatcccgatgctgaaagaaatgattcggcatgcgggaaatagcggaactcgggaagtggtgttaggaatggc
acaccgcggccgtttgaatgtactggttaacgtattaggaaaaaaacctcaggattttatttgatgagttcgcgggaa
aacataaagaacatctgggcactggtgatgtcaaatatcacatgggcttctcaagtgattttcagacggatggaggt
ctggttcacctggcactggcatttaatccttctcatctggaaatcgtaagtccggtcgttattggttccgtgcgcgc
tcgcttagatcggttagatgaacctagctcaaacaaagttttaccaatcacgatccatggggatgcagctgttaccg
gacagggtgttgtgcaggagactttgaatatgtccaaagcgcgcgggtatgaggtgggtggtacggtgcgtattgtt
atcaataatcaggtgggttttacaaccagtaaccctctggatgctcgctctacgccgtattgcactgatattggtaa
aatggtgcaggcaccaattttttcacgtcaatgccgatgatccggaagctgttgcctttgttacgcgcctggctctgg
attttcgtaacactttcaaacgtgatgtatttatcgatttagtatgctatcgtcgtcatggtcataatgaggctgat
gaacctagcgctacccagccactgatgtatcagaaaattaaaaaacatcctacccctcgtaaaatttatgcggataa
actggagcaggaaaaagtggctactcttgaagatgctactgaaatggtcaatctttatcgggatgcattggatgcgg
tgattgcgtggtcgcggaatggcgcccgatgaatatgcattcatttacttggtcaccgtatttaaatcatgagtgg
gatgaggaatatccgaataaagtggagatgaaacgcctgcaggaattagcaaaacgtattagcacagtacctgaagc
ggttgagatgcagtctagagttgccaaaatctatggagatcgccaggccatggcagcaggggaaaaacttttttgatt
gggggggagccgaaaacctggcatatgcgacgctggtagatgagggcattccggtgcgcctttctggtgaagattct
gggcgcggtactttttttcatcggcacgctgttattcataaccagtctaacggtagtacttatactccgctgcagca
catccacaatggtcagggtgcgttccgtgtatggattccgtgctggtgagaagcggttcttgcgtttgagtatg
ggtatgcaactgccgagccacgcacgctgacgatctgggacgccagtttggcgattttgcaaatggtgcccaggtg
gtaatcgatcagtttattagctccggcgaacagaaatgggggcggatgtgtggtttagttatgttgttaccgcatgg
ctatgaaggtcagggacctgagcacagctcagcgcgcctggaacgctatcttcagctgtgtgcggaacagaacatgc
aggtatgcgttccttccacgccggctcaggtttatcatatgttaagacgtcaggccttgcgcggtatgcggcgcccg
ttggtcgtgatgtccccgaaaagtttactgcgccatccgttagcagttagcagcctggaggaactggcaaacggtac

Sequences of Interest:

```
gttcttgccagctatcggcgaaatcgatgaactggatcctaaaggggtgaaacgcgttgttatgtgttctggtaaag
tgtattatgatcttttggaacagcgtcgcaaaaataatcagcacgatgtagctattgtgcggatcgagcagctgtat
ccgttcccgcacaaagcaatgcaggaagtgctgcagcagttcgacatgtcaaagatttttgtctggtgtcaggagga
accgcttaatcaggggggcctggtattgtagtcagcaccatttccgggaggtgatcccgtttggggcgtccttacggt
atgctggtcgccctgcctccgcaagtccggccgtgggatatatgagcgttcaccagaaacagcagcaggatttggtg
aatgatgctttgaatgtggaatgaatgtccatcctgatcgacaaaaacactaaagtaatttgtcagggctttaccgg
ttcccagggcacattttcactcagagcaggccatcgcttatgggaccaaaatggtgggtggtgtaacgcctggtaag
gaggcaccacccatctgggtttgccggtatttaataccgtgcgtgaggcggttgccgcaaccggtgccacggcttca
gttatctatgttcctgccccattttgtaaagattcaattctggaagctattgatgcgggcatcaaattgattattac
gattaccgaaggtatccctacgctggatatgttgacggttaaagtgaaacttgatgaagcggggtacgcatgattg
gtccgaattgtccgggcgttattactccaggtgagtgcaaaattggtattcagccgggtcatattcacaaacctggg
aaagtcggaattgtgtctcgttctggcactctgacgtatgaggcagttaaacagaccacagattatggctttgggca
gagtacctgtgtcggcatcggaggcgatcctattccggggagtaattttatcgatattctggaaatgtttgagaaag
atccgcagaccgaggcaatcgtcatgattggcgagattggcggttccgcggaagaagaagctgcagcctatatcaaa
gaacatgtcacaaaaccggtagtgggctatatcgcgggagtcacggcccaaaaggtaaacgtatgggccatgccgg
agcgatcatcgcgggcggcaaaggcactgcagatgaaaaatttgcagccccttgaggcgcctggcgtaaaaacggtcc
gttcccttgctgatattggtgaagcactgaaaaccgtgttgaaataaAGGTccaggcatcaaatAaaaacgaaaggct
cagtcgaaagactgggcctttcgttttatctgttgtttgtcggtgaacgctctctactagagtcacactggctcacc
ttcgggtgggcctttctgcgtttatactcgagtgccacctgacgtctaagaaaccattattatcatgacattaacct
ataaaaataggcgtatcacgaggcagaatttcagataaaaaaaatccttagctttcgctaaggatgatttctggaat
tcgcggccgcttctagagactagtggaagacatcgctagagacctgcaccatatgcggtgtgaaataccgcacagat
gcgtaaggagaaaataccgcatcaggcgccattcgccattcaggctgcgcaactgttgggaagggcgatcggtgcgg
gcctcttcgctattacgccagctggcgaaaggggggatgtgctgcaaggcgattaagttgggtaacgccagggttttc
ccagtcacgacgttgtaaaacgacggccagtgaattcgagctcggtacccggggatcctctagagtcgacctgcag
catgcaagcttggcgtaatcatggtcatagctgtttcctgtgtgaaattgttatccgctcacaattccacacaacat
acgagccggaagcataaagtgtaaagcctggggtgcctaatgagtgagctaactcacattaattgcgttgcgctcac
tgcccgctttccagtcgggaaacctgtcgtgccagctgcattaatgaatcggccaacgcgcggggagtttatAaaatc
ccgtcaagtcagcgtaatgctctgccagtgttacaaccaattaaccaattctgattagaaaaactcatcgagcatca
aatgaaactgcaatttattcatatcaggattatcaataccatattttgaaaaagccgtttctgtaatgaaggagaa
aactcaccgaggcagttccataggatggcaagatcctggtatcggtctgcgattccgactcgtccaacatcaataca
acctattaatttcccctcgtcaaaaataaggttatcaagtgagaaatcaccatgagtgacgactgaatccggtgaga
atggcaaaagcttatgcatttctttccagacttgttcaacaggccagccattacgctcgtcatcaaaatcactcgca
tcaaccaaaccgttattcattcgtgattgcgcctgagcgagacgaaatacgcgatcgctgttaaaaggacaattaca
aacaggaatcgaatgcaacggcgcaggaacactgccagcgcatcaacaatattttcacctgaatcaggatattctt
ctaatacctggaatgctgttttcccggggatcgcagtggtgagtaaccatgcatcatcaggagtacggataaaatgc
ttgatggtcggaagaggcataaattccgtcagccagtttagtctgaccatctcatctgtaacatcattggcaacgct
acctttgccatgtttcagaaacaactctggcgcatcgggcttcccatacaatcgatagattgtcgcacctgattgcc
cgacattatcgcgagcccatttatacccatataaatcagcatccatgttggaatttaatcgcggcctcggagcaagac
gtttcccgttgaatatggctcataacaccccttgtattactgtttatgtaagcagacagttttattgttcatgatga
tatatttttatcttgtgcaatgtaacatcagagattttgagacacaacgtggctttgttgaataaatcgaacttttg
ctgagttgaaggatcagggtcttcttgccatgtcttctactagtagcggccgctgcagtccggcaaaaagggcaagg
tgtcaccaccctgcccttttctcttaaaaccgaaaagattacttcgcgttatgcaggcttcctcgctcactgactcg
ctgcgctcggtcgttcggctgcggcgagcggtatcagctcactcaaaggcggtaatacggttatccacagaatcagg
ggataacgcaggaaagaacatgtgagcaaaaggccagcaaaaggccaggaaccgtaaaaaggc
```

SEQ ID NO: 7. Sequence of the pDvQ vector, designed for facile cloning with a modular cloning system. It contains the entire sucABCD operon including native 5' UTR instead of an antibiotic resistance marker.

```
cgcgttgctggcgtttttccacaggctccgcccccctgacgagcatcacaaaaatcgacgctcaagtcagaggtggc
gaaacccgacaggactataaagataccaggcgtttccccctggaagctccctcgtgcgctctcctgttccgaccctg
ccgcttaccggatacctgtccgcctttctcccttcgggaagcgtggcgctttctcatagctcacgctgtaggtatct
cagttcggtgtaggtcgttcgctccaagctgggctgtgtgcacgaaccccccgttcagcccgaccgctgcgccttat
ccggtaactatcgtcttgagtccaacccggtaagacacgacttatcgccactggcagcagccactggtaacaggatt
agcagagcgaggtatgtaggcggtgctacagagttcttgaagtggtggcctaactacggctacactagaagaacagt
atttggtatctgcgctctgctgaagccagttaccttcggaaaaagagttggtagctcttgatccggcaaacaaacca
ccgctggtagcggtggtttttttgtttgcaagcagcagattacgcgcagaaaaaaaggatctcaagaagatcctttg
atcttttctacggggtctgacgctcagtggaacgaaaactcacgttaagggattttggtcatgagattatcaaaaag
gatcttcacctagatccttttaaattaaaaatgaagttttaaatcaatctaaagtatatatgagtaaacttggtctg
acagctcgaggtaggcctgataagacgcgcaagcgtcgcatcaggcaaccagtgccggatgcggcgtgaacgcctta
tccggcctacaagtcattaccgtaggcctgataagcgcagcgcatcaggcgtaacaaagaaatgcaggaaatctttt
aaaaactgcccctgacactaagacagttttaaaggttccttcgcgagccactacgtagacaagagctcgcaagtga
accccggcacgcacatcactgtgcgtggtagtatccacggcgaagtaagcataaaaaagatgcttaaggagtcacgA
ATGcagaacagcgctttgaaagcctggttggactcttcttacctctctggcgcaaaccagagctggatagaacagct
ctatgaaGATtttcttaaccgatcctgactcggttgacgctaactggcgttcgacgttccagcagttacctggtacgg
gagtcaaaccggatcaattccactctcaaacgcgtgaatatttccgccgcctggcgaaagacgcttcacgttactct
tcaacgatctccgaccctgacaccaatgtgaagcaggttaaagtcctgcagtctcattaacgcatacccgcttccgtgg
tcaccagcatgcgaatctcgatccgctgggactgtggcagcaagataaagtggccgatctggatccgtctttccacg
atctgaccgaagcagacttccaggagACTttcaacgtcggttcatttgccagcggcaaagaaaccatgaaactcggc
gagctgctggaagccctcaagcaaacctactgcgggcccgattggtgccgagtatatgcacattaccagcaccgaaga
aaaacgctggatccaacagcgtatcgagtctggtcgcgcgactttcaatagcgaagagaaaaaacgcttcttaagcg
aactgaccgccgctgaaggtcttgaacgttacctcggcgcaaaattccctggcgcaaaacgcttctcgctggaaggc
ggtgacgcgttaatcccgatgcttaaagagatgatccgccacgctggcaacagcggcacccgcgaagtggttctcgg
gatgcgcaccgtggtcgtctgaacgtgctggtgaacgtgctgggtaaaaaaccgcaagacttgttcgacgagttcg
ccggtaaacataaagaacacctcggcacgggtgacgtgaaataccacatgggcttctcgtctgacttccagaccgat
ggcggcctggtgcacctggcgctggcgtttaaccgtctcaccttgagattgtaagcccggtagttatcggttctgt
tcgtgcccgtctggacagacttgatgagccgagcagcaacaaagtgctgccaatcaccatccacggtgacgccgcag
tgaccgggcagggcgtggttcaggaaaccctgaacatgtcgaaagcgcgtggttatgaagttggcggtacggtacgt
```

-continued

Sequences of Interest:

```
atcgttatcaacaaccaggttggtttcaccacctctaatccgctggatgccgttctacgccgtactgtactgatat
cggtaagatggttcaggccccgattttccacgttaacgcggacgatccggaagccgttgcctttgtgacccgtctgg
cgctcgatttccgtaacaccctttaaacgtgatGTTtttcatcgacctggtgtgctaccgccgtcacggccacaacgaa
gccgacgagccgagcgcaacccagccgctgatgtatcagaaaatcaaaaaacatccgacaccgcgcaaaatctacgc
tgacaagctggagcaggaaaaagtggcgacgctggaagatgccaccgagatggttaacctgtaccgcgatgcgctgg
atgctggcgattgcgtagtggcagagtggcgtccgatgaacatgcactctttcacctggtcgccgtacctcaaccac
gaatgggacgaagagtacccgaacaaagttgagatgaagcgcctgcaggagctggcgaaacgcatcagcacggtgcc
ggaagcagttgaaatgcagtctcgcgttgccaagatttatggcgatcgccaggcgatggctgccggtgagaactgt
tcgactggggcggtgcggaaaacctcgcttacgccacgctggttgatgaaggcattccggttcgcctgtcgggtGAG
gactccggtcgcggtaccttcttccaccgccacgcggtgatccacaaccagtctaacggttccacttacacgccgct
gcaacatatccataacgggcagggcgcgttccgtgtctggactccgtactgtctgaagaagcagtgctggcgtttg
aatatggttatgccaccgcagaaccacgcactctgaccatctgggaagcgcagttcggtgacttcgccaacggtgcg
caggtggttatcgaccagttcatctcctctggcgaacagaaatggggccggatgtgtggtctggtgatgttgctgcc
gcacggttacgaagggcagggccggagcactcctccgcgcgtctggaacgttatctgcaactttgtgctgagcaaa
acatgcaggtttgcgtaccgtctacccccggcacaggtttaccacatgctgcgtcgtcaggcgctgcgcgggatgcgt
cgtccgctggtcgtgatgtcgccgaaatccctgctgcgtcatccgctggcggtttccagcctcgaagaactggcgaa
cggcaccttcctgccagccatcggtgaaatcgacgagcttgatccgaaggcgtgaagcgcgtagtgatgtgttctg
gtaaggtttattacgacctgctggaacagcgtcgtaagaacaatcaacacgatgtcgccattgtgcgtatcgagcaa
ctctacccgttcccgcataaagcgatgcaggaagtgttgcagcagtttgctcacgtcaaggattttgtctggtgcca
ggaagagccgctcaaccagggcgcatggtactgcagccagcatcatttccgtgaagtgattccgtttgggcttctc
tgcgttatgcaggccgcccggcctccgcctctccggcggtagggtatatgtccgttcaccagaaacagcaacaagat
ctggttaatgacgcgctgaacgtcgaataaataaaggatacacaatgagtagcgtagatattctggtccctgacctg
cctgaatccgtagccgatgccaccgtcgcaacctggcataaaaaacccggcgacgcagtcgtacgtgatgaagtgct
ggtagaaatcgaaactgacaaagtggtactggaagtaccggcatcagcagacggcattctggatgcggttctggaag
atgaaggtacaacggtaacgtctcgtcagatccttggtcgcctgcgtgaaggcaacagcgccggtaaagaaaccagc
gccaaatctgaagagaaagcgtccactccggcgcaacgccagcaggcgtctctgaagagcaaaacaacgatgcgtt
aagcccggcgatccgtcgcctgctggctgaacacaatctcgacgccagcgccattaaaggcaccggtgtgggtggtc
gtctgactcgtgaagatgtggaaaaacatctggcgaaagccccggcgaaagagtctgctccggcagcggctgctccg
gcggcgcaaccggctctggctgcacgtagtgaaaaacgtgtcccgatgactcgcctgcgtaagcgtgtggcagagcg
tctgctggaagcgaaaaactccaccgccatgctgaccacgttcaacgaagtcaacatgaagccgattatggatctgc
gtaagcagtacggtgaagcgtttgaaaaacgccacgcatccgtctgggctttatgtccttctacgtgaagcggtg
gttgaagccctgaaacgttacccggaagtgaacgcttctatcgacggcgatgacgtggtttaccacaactatttcga
cgtcagcatggcggtttctacgccgcgcggcctggtgacgccggttctgcgtgatgtcgataccctcggcatggcag
acatcgagaagaaaatcaaagagctggcagtcaaaggccgtgacggcaagctgaccgttgaagatctgaccggtggt
aacttcaccatcaccaacggtggtgtgttcggttccctgatgtctacgccgatcatcaacccgccgcagagcgcaat
tctgggtatgcacgctatcaaagatcgtccgatggcggtgaatggtcaggttgagatcctgccgatgatgtacctgg
cgctgtcctacgatcaccgtctgatcggtcgcgaatccgtgggtcctggtaacgatcaaagagttgctggaa
gatccgacgcgtctgctgctggacgtgtagtagtttaagtttcacctgcactgtagaccggataaggcattatcgcc
ttctccggcaattgaagcctgatgcgacgctgacgcgtcttatcaggcctacgggaccaccaatgtaggtcggataa
ggcgcaagcgccgcatccgacaagcgatgcctgatgtgacgtttaacgtgtcttatcaggcctacgggtgaccgaca
atgcccggaagcgatacgaaatattcGGTCTACGGTTTAAAAGATAACGATTACTGAAGGATGGACAGAACACatga
acttacatgaatatcaggcaaaacaacttttttgcccgctatggcttaccagcaccggtgggttatgcctgtactact
ccgcgcgaagcagaagaagccgcttcaaaaatcggtgccggtccgtgggtagtgaaatgtcaggttcacgctggtgg
ccgcggtaaagcgggcggtgtgaaagttgtaaacagcaaaGAGgacatccgtgcttttgcagaaaactggctgggca
agcgtctggtaacgtatcaaacagatgccaatggccaaccggttaaccagattctggttgaagcagcgaccgatatc
gctaaagagctgtatctcggtgccgttgttgaccgtagttcccgtcgtgtggtctttatggcctccaccgaaggcgg
cgtggaaatcgaaaaagtggcggaagaaactccgcacctgatccataaagttgcgcttgatccgctgactggcccga
tgccgtatcagggacgcgagctggcgttcaaactgggtctggaaggtaaactggttcagcagttcaccaaaatcttc
atgggcctggcgaccattttcctggagcgcgacctggcgttgatcgaaatcaaccgctggtcatcaccaaacaggg
cgatctgatttgcctcgacggcaaactggggcgctgacggcaacgcactgttccgccagcctgatctgcgcgaaatgc
gtgaccagtcgcaggaagatccgcgtgaagcacaggctgcacagtgggaactgaactacgttgcgctggacggtaac
atcggttgtatggttaacggcgcaggtctggcgatgggtacgatggacatcgttaaactgcacggcggcgaaccggc
taacttccttgacgttggcggcggcgcaacccaaaaaacgtgtaaccgaagcgttcaaaatcatcctctctgacgaca
aagtgaaagccgttctggttaacatcttcggcggtatcgttcgttgcgacctgatcgctgacggtatcatcggcgcg
gtagcagaagtgggtgttaacgtaccggtcgtggtacgtctggaaggtaacaacgccgaactcggcgcgaagaaact
ggctgacagcggcctgaatattattgcagcaaaaggtctgacggatgcagctcagcaggttgttgccgcagtggagg
ggaaataatgtccattttaatcgataaaaaacaccaaggttatctgccagggcttaccggtagccagggggacttttcc
actcagaacaggccattgcatacggcactaaaatggttggcggcgtaaccccaggtaaaggcggcaccaccacctc
ggcctgccggtgttcaacaccgtcgctgaagccgttgctgccactggcgctaccgcttctgttatctacgtaccagc
accgttctgcaaagactccattctggaagccatcgacgcaggcatcaaactgattatcaccatcactgaaggcatcc
cgacgctggatatgctgaccgtgaaagtgaagctggatgaagcaggcgttcgtatgatcggcccgaactgcccaggc
gttatcacttccgggtgaatgcaaaatcggtatccagcctggtcacattcacaaaccggcaagtgggtatcgtttc
ccgttccggtacactgacctatgaagcggttaaacagaccacgattacggtttcggtcagtcgacctgtgtcggta
tcggcggtgacccgatcccgggctctaactttatcgacattctcgaaatgttcgaaaaagatccgcagaccgaagcg
atcgtgatgatcggtgagatcggcggtagcgctgaagaagaagcagctgcgtacatcaaagagcacgttaccaagcc
agttgtgggttacatcgctggtgtgactgcgccgaaaggcaaactatgggccacgcgggtgccatcattgccggtg
ggaaagggactgcggatgagaaattcgctgctctggaagccgcaggcgtgaaaaccgttcgcagcctggcggatatc
ggtgaagcactgaaaactgttctgaaataaaggtccaggcatcaaataaaacgaaaggctcagtcgaaagactgggc
ctttcgttttatctgttgtttgtcggtgaacgctctctactagagtcacactggctcaccttcgggtgggcctttct
gcgtttatactcgagtgccacctgacgtctaagaaaccattattatcatgacattaacctataaaaataggcgtatc
acgaggcagaatttcagataaaaaaaatccttagctttcgctaaggatgatttctggaattcgcggccgcttctaga
gactagtgaaagacatcgctagagacctgcaccatatgcggtgtgaaataccgcacagatgcgtaaggagaaaatac
cgcatcaggcgccattcgccattcaggctgcgcaactgttgggaagggcgatcggtgcgggcctcttcgctattacg
ccagctggcgaaagggggatgtgctgcaaggcgattaagttgggtaacgccagggttttcccagtcacgacgttgta
aaacgacggccagtgaattcgagctcggtacccggggatcctctagagtcgacctgcaggcatgcaagcttggcgta
atcatggtcatagctgtttcctgtgtgaaattgttatccgctcacaattccacacaacatacgagccggaagcataa
agtgtaaagcctggggtgcctaatgagtgagctaactcacattaattgcgttgcgctcactgcccgctttccagtcg
```

Sequences of Interest:

```
ggaaacctgtcgtgccagctgcattaatgaatcggccaacgcgcggggtttataaaatcccgtcaagtcagcgtaa
tgctctgccagtgttacaaccaattaaccaattctgattagaaaaactcatcgagcatcaaatgaaactgcaattta
ttcatatcaggattatcaataccatattttgaaaaagccgtttctgtaatgaaggagaaactcaccgaggcagtt
ccataggatggcaagatcctggtatcggtctgcgattccgactcgtccaacatcaatacaacctattaatttcccct
cgtcaaaaataaggttatcaagtgagaaatcaccatgagtgacgactgaatccggtgagaatggcaaaagcttatgc
atttctttccagacttgttcaacaggccagccattacgctcgtcatcaaaatcactcgcatcaaccaaaccgttatt
cattcgtgattgcgcctgagcgagacgaaatacgcgatcgctgttaaaaggacaattacaaacaggaatcgaatgca
accggcgcaggaacactgccagcgcatcaacaatattttcacctgaatcaggatattcttctaatacctggaatgct
gttttcccggggatcgcagtggtgagtaaccatgcatcatcaggagtacggataaaatgcttgatggtcggaagagg
cataaattccgtcagccagtttagtctgaccatctcatctgtaacatcattggcaacgctacctttgccatgtttca
gaaacaactctggcgcatcgggcttcccatacaatcgatagattgtcgcacctgattgcccgacattatcgcgagcc
catttataccatataaatcagcatccatgttggaatttaatcgcggcctggagcaagacgtttcccgttgaatatg
gctcataacacccccttgtattactgtttatgtaagcagacagttttattgttcatgatgatatattttatcttgtg
caatgtaacatcagagattttgagacacaacgtggctttgttgaataaatcgaacttttgctgagttgaaggatcag
ggtctcttgccatgtcttctactagtagcggccgctgcagtccggcaaaaagggcaaggtgtcaccaccctgccct
ttttctttaaaaccgaaaagattacttcgcgttatgcaggcttcctcgctcactgactcgctgcgctcggtcgttcg
gctgcggcgagcggtatcagctcactcaaaggcggtaatacggttatccacagaatcaggggataacgcaggaaaga
acatgtgagcaaaaggccagcaaaaggccaggaaccgtaaaaaggc
```

SEQ ID NO: 8. Sequence of Plasmid pDvS-GFP containing a sequence encoding the
green fluorescent protein cloned into the pDvS vector
```
tactgcgccatccgttagcagttagcagcctggaggaactggcaaacggtacgttcttgccagctatcggcgaaatc
gatgaactggatcctaaaggggtgaaacgcgttgttatgtgttctgtaaagtgtattatgatcttttggaacagcg
tcgcaaaaataatcagcacgatgtagctattgtgcggatcgagcagctgtatccgttcccgcacaaagcaatgcagg
aagtgctgcagcagttcgcacatgtcaaagattttgtctggtgtcaggaggaaccgcttaatcagggggcctggtat
tgtagtcagcaccatttccgggaggtgatcccgtttgggcgtccttacggtatgctggtcgccctgcctccgcaag
tccggccgtgggatatatgagcgttcaccagaaacagcagcaggatttggtgaatgatgctttgaatgtggaatgaa
tgtccatcctgatcgacaaaaacactaaagtaatttgtcagggctttaccggttcccagggcacatttcactcagag
caggccatcgcttatgggaccaaaatggtgggtggtgtaacgcctggtaaaggaggcaccacccatctgggtttgcc
ggtatttaataccgtgcgtgaggcggttgccgcaaccggtgccacggcttcagttatctatgttcctgccccatttt
gtaaagattcaattctggaagctattgatgcgggcatcaaattgattattacgattaccgaaggtatccctacgctg
gatatgttgacggttaaagtgaaacttgatgaagcgggggtacgcatgattggtccgaattgtccgggcgttattac
tccaggtgagtgcaaaattggtattcagccgggtcatattcacaaacctgggaaagtcggaattgtgtctcgttctg
gcactctgacgtatgaggcagttaaacagaccacagattatggctttgggcagagtacctgtgtcggcatcggagcc
gatcctattccggggagtaattttatcgatattctggaaatgtttgagaaagatccgcagaccgaggcaatcgtcat
gattggcgagattggcggttccgcggaagaagaagctgcagcctatatcaaagaacatgtcacaaaaccggtagtgg
gctatatcgcgggagtcacggcccaaaaggtaaacgtatgggccatcatcgcgggcggcaaaggc
actgcagatgaaaaatttgcagcccttgaggccgctggcgtaaaaacggtccgttccttgctgatattggtgaagc
actgaaaaccgtgttgaaataaAGGTccaggcatcaaataaaacgaaaggctcagtcgaaagactgggcctttcgtt
ttatctgttgtttgtcggtgaacgctctctactagagtcacactggctcaccttcgggtgggcctttctgcgtttat
atcccgtcaagtcagcgtaatgctctgccagtgttacaaccaattctgattagaaaaactcatcgagcaga
tcaaatgaaactgcaatttattcatatcaggattatcaataccatattttgaaaaagccgtttctgtaatgaagga
gaaaactcaccgaggcagttccataggatggcaagatcctggtatcggtctgcgattccgactcgtccaacatcaat
acaacctattaatttcccctcgtcaaaaataaggttatcaagtgagaaatcaccatgagtgacgactgaatccggtg
agaatggcaaaagcttatgcatttctttccagacttgttcaacaggccagccattacgctcgtcatcaaaatcactc
gcatcaaccaaaccgttattcattcgtgattgcgcctgagcgagacgaaatacgcgatcgctgttaaaaggacaatt
acaaacaggaatcgaatgcaaccggcgcaggaacactgccagcgcatcaacaatattttcacctgaatcaggatatt
cttctaatacctggaatgctgttttcccggggatcgcagtggtgagtaaccatgcatcatcaggagtacggataaaa
tgcttgatggtcggaagaggcataaattccgtcagccagtttagtctgaccatctcatctgtaacatcattggcaac
gctacctttgccatgtttcagaaacaactctggcgcatcgggcttcccatacaatcgatagattgtcgcacctgatt
gcccgacattatcgcgagcccatttataccatataaatcagcatccatgttggaatttaatcgcggcctggagcaa
gacgtttcccgttgaatatggctcataacacccctttgtattactgtttatgtaagcagacagttttattgttcatga
tgatatattttatcttgtgcaatgtaacatcagagattttgagacacaacgtggctttgttgaataaatcgaactt
ttgctgagttgaaggatcagctcgagtgccacctgacgtctaagaaaccattattatcatgacattaacctataaaa
ataggcgtatcacgaggcagaatttcagataaaaaaaatcctagctttcgctaaggatgatttctggaattcgcgg
ccgcttctagagactagtgaagacatcgctggaaagtgaaacgtgatttcatgcgtcatttgaacattttgtaaa
tcttatttaataatgtgtgcggcaattcacatttaatttatgaatgttttcttaacatcgcggcaactcaagaaacg
gcaggttcggatcttagctactagagaaagaggagaaatactagatgcgtaaaggcgaagagctgttcactggtgtc
gtccctattctggtggaactggatggtgatgtcaacggtcataagttttccgtgcgtggcgagggtgaaggtgacgc
aactaatggtaaactgacgctgaagttcatctgtactactggtaaactgccggttccttggccgactctggtaacga
cgctgacttatggtgttcagtgctttgctcgttatccggaccatatgaagcagcatgacttcttcaagtccgccatg
ccggaaggctatgtgcaggaacgcacgattcctttaaggatgacggcacgtacaaaacgcgtgcggaagtgaaatt
tgaaggcgataccctggtaaaccgcattgagctgaaaggcattgactttaaagaggacggcaatatcctgggccata
gctggaatacaattttaacagccacaatgtttacatcaccgccgataaacaaaaaaatggcattaaagcgaatttt
aaaattcgccacaacgtggaggatggcagcgtgcagctggctgatcactaccagcaaaacactccaatcggtgatgg
tcctgttctgctgccagacaatcactatctgagcacgcaaagcgttctgtctaaagatccgaacgagaaacgcgatc
atatggttctgctggagttcgtaaccgcagcgcatcacgcatgctgtaagatcgtacaaatgaccaggcatc
aaatacaaacgaaaggctcagtcgaaagactgggcctttcgttttatctgttgtttgtcggtgaacgctctctactag
agtcacactggctcaccttcgggtgggcctttctgcgtttatacgtgccatgtcttctactagtagcggccgctgca
gtccggcaaaaagggcaaggtgtcaccaccctgcccttttttcttaaaaccgaaaagattacttcgcgttatgcag
gcttcctcgctcactgactcgctgcgctcggtcgttcggctgcggcgagcggtatcagctcactcaaaggcggtaat
acggttatccacagaatcaggggataacgcaggaaagaacatgtgagcaaaaggccagcaaaaggccaggaaccgta
aaaaggccgcgttgctggcgtttttccacaggctccgccccctgacgagcatcacaaaaatcgacgctcaagtcag
aggtggcgaaacccgacaggactataaagataccaggcgtttccccctggaagctccctcgtgcgctctcctgttcc
gaccctgccgcttaccggatacctgtccgcctttctcccttcgggaagcgtggcgctttctcatagctcacgctgta
ggtatctcagttcggtgtaggtcgttcgctccaagctgggctgtgtgcacgaaccccccgttcagcccgaccgctgc
gccttatccggtaactatcgtcttgagtccaacccggtaagacacgacttatcgccactggcagcagccactggtaa
```

Sequences of Interest:

caggattagcagagcgaggtatgtaggcggtgctacagagttcttgaagtggtggcctaactacggctacactagaa
gaacagtatttggtatctgcgctctgctgaagccagttaccttcggaaaaagagttggtagctcttgatccggcaaa
caaaccaccgctggtagcggtggtttttttgtttgcaagcagcagattacgcgcagaaaaaaaggatctcaagaaga
tcctttgatcttttctacggggtctgacgctcagtggaacgaaaactcacgttaagggattttggtcatgagattat
caaaaaggatcttcacctagatccttttaaattaaaaatgaagttttaaatcaatctaaagtatatatgagtaaact
tggtctgacagctcgagtttacggctagctcagtcctaggtatagtgctagcTACTtgttagaaaagagaagcacgt
aatgcagaactcagcattgaaagcatggcttgatagctcctatttatcaggtgctaaccagagctggattgaacagc
tgtatgaagattttctgacagatccggattcagtggatgcgaattggcgcagcacttttcagcagttgcctggcacc
ggtgtaaaaccggatcagtttcattcccagacgcgggagtattttcgtcgtctggcgaaagatgcgagccggtattc
aagtacaatttctgatccggatacgaatgtaaaacaggtgaaagtgcttcagttaattaatgcgtatcgctttagag
gccatcagcatgcgaatctggatccgctgggcttatggcagcaggataaagtcgcggatctggatccaagttttcac
gatttaacggaagctgattttcaggaaaccttttaacgtcggctcattcgcaagtgggaaagaaacaatgaaactggg
cgaacttcttgaggcgctgaaacagacttattgtggccctattggtgcggaatatatgcatattacctcaactgaag
agaaacgttggattcagcagagaatcgagagtggccgcgcgacttttaactccgaagaaaaaaaaagattcctgtca
gaactgacagccgcggaaggcttagagcggtatttgggtgccaaattcccaggagcaaaacggttcagcctggaggg
cggtgatgcgctgatcccgatgctgaaagaaatgattcggcatgcgggaaatagcggaactcgggaagtggtgttag
gaatggcacaccgcggccgtttgaatgtactggttaacgtattaggaaaaaaacctcaggatttatttgatgagttc
gcgggaaaacataaagaacatctgggcactggtgatgtcaaatatcacatgggcttctcaagtgattttcagacgga
tggaggtctggttcacctggcactggcatttaatccttctcatctggaaatcgtaagtccggtcgttattggttccg
tgcgcgctcgcttagatcggttagatgaacctagctcaaacaaagtttaccaatcacgatccatggggatgcagct
gttaccggacagggtgttgtgcaggagactttgaatatgtccaaagcgcgcgggtatgaggtgggtggtacggtgcg
tattgttatcaataatcaggtgggttttacaaccagtaaccctctggatgctcgctctacgccgtattgcactgata
ttggtaaaatggtgcaggcaccaattttttcacgtcaatgccgatgatccggaagctgttgcctttgttacgcgcctg
gctctggattttcgtaacacttttcaaacgtgatgtatttttcgatttagtatgctatcgtcgtcatggtcataatga
ggctgatgaacctagcgctacccagccactgatgtatcagaaaattaaaaaaacatcctacccctcgtaaaatttatg
cggataaactggagcaggaaaaagtggctactcttgaagatgctactgaaatggtcaatctttatcgggatgcattg
gatgcgggtgattgcgtggtcgcggaatggcgcccgatgaatatgcattcatttacttggtcaccgtatttaaatca
tgagtgggatgaggaatatccgaataaagtggagatgaaacgcctgcaggaattagcaaaacgtattagcacagtac
ctgaagcggttgagatgcagtctagagttgccaaaatctatggagatcgccaggccatggcagcaggggaaaaactt
tttgattgggggggagccgaaaacctggcatatgcgacgctggtagatgagggcattccggtgcgccttctggtga
agattctgggcgcggtacttttttttcatcggcacgctgttattcataaccagtctaacggtagtacttatactccgc
tgcagcacatccacaatggtcagggtgcgttccgtgtatgggattccgtgctgagtgaagaagcggttcttgcgttt
gagtatggtatgcaactgccgagccacgcacgctgacgatctgggaagcccagtttggcgattttgcaaatggtga
ccaggtggtaatcgatcagtttattagctccggcgaacagaaatggggggcggatgtgtggtttagttatgttgttac
cgcatggctatgaaggtcagggacctgagcacagctcagcgcgcctggaacgctatcttcagctgtgtgcggaacag
aacatgcaggtatgcgttccttccacgccggctcaggtttatcatatgttaagacgtcaggccttgcgcggtatgcg
gcgcccgttggtcgtgatgtccccgaaaagtt SEQ ID NO: 9. Sequence of Plasmid pDvQ-GFP containing a sequence encoding the
green fluorescent protein cloned into the pDvQ vector
cgcgttgctggcgtttttccacaggctccgcccccctgacgagcatcacaaaaatcgacgctcaagtcagaggtggc
gaaacccgacaggactataaagataccaggcgtttccccctggaagctccctcgtgcgctctcctgttccgaccctg
ccgcttaccggatacctgtccgcctttctcccttcgggaagcgtggcgctttctcatagctcacgctgtaggtatct
cagttcggtgtaggtcgttcgctccaagctgggctgtgtgcacgaaccccccgttcagcccgaccgctgcgccttat
ccggtaactatcgtcttgagtccaacccggtaagacacgacttatcgccactggcagcagccactggtaacaggatt
agcagagcgaggtatgtaggcggtgctacagagttcttgaagtggtggcctaactacggctacactagaagaacagt
atttggtatctgcgctctgctgaagccagttaccttcggaaaaagagttggtagctcttgatccggcaaacaaacca
ccgctggtagcggtggtttttttgtttgcaagcagcagattacgcgcagaaaaaaaggatctcaagaagatcctttg
atctttctacggggtctgacgctcagtggaacgaaaactcacgttaagggattttggtcatgagattatcaaaaag
gatcttcacctagatccttttaaattaaaaatgaagttttaaatcaatctaaagtatatatgagtaaacttggtctg
acagctcgaggtaggcctgataagacgcgcaagcgtcgcatcaggcaaccagtgccggatgcggcgtgaacgcctta
tccggcctacaagtcattacccgtaggcctgataagcgcagcgcatcaggcgtaacaaagaaatgcaggaaatcttt
aaaaactgcccctgacactaagacagttttaaaggttccttcgcgagcgcactacgtagacaagagctcgcaagtga
accccggcacgcacatcactgtgcgtggtagtatccacggcgaagtaagcataaaaaagatgcttaagggatcacgA
ATGcagaacagcgctttgaaagcctggttggactcttcttacctctctggcgcaaaccagagctggatagaacagct
ctatgaaGATtcttaaccgatcctgactcggttgacgctaactggcgttcgacgttccagcagttacctggtacgg
gagtcaaaccggatcaattccactctcaaacgcgtgaatatttccgccgcctggcgaaagacgcttcacgttactct
tcaacgatctccgaccctgacaccaatgtgaagcaggttaaagtcctgcagtcattaacgcataccgcttccgtgg
tcaccagcatgcgaatctcgatccgctgggactgtggcagcaagataaagtggccgatctggatccgtctttccacg
atctgaccgaagcagacttccaggagACTttcaacgtcggttcatttgccagcggcaaagaaaccatgaaactcggc
gagctgctggaagccctcaagcaaacctactgcgggcccgattggtgccgagtatatgcacattaccagcaccgaaga
aaaacgctggatccaacagcgtatcgagtctggtcgcgcggactttcaatagcgagagaaaaaacgcttcttaagcg
aactgaccgccgctgaaggtcttgaacgttacctcggcgcaaaattccctggcgcaaaacgcttctcgctggaaggc
ggtgacgcgttaatcccgatgcttaaagagatgatccgccacgctggcaacagcggcaccccgcgaagtggttctcgg
gatggcgcaccgtggtcgtctgaacgtgctggtgaacgtgctgggtaaaaaaccgcaagacttgttcgacgagttcg
ccggtaaacataaagaacaccctcggcacgggtgacgtgaaataccacatgggcttctcgtctgacttccagaccgat
ggcggcctggtgcacctggcgctggcgtttaaccgtctccaccttgagattgtaagccgggtagttatcggttctgt
tcgtgcccgtctggacagacttgatgagccgagcagcaacaaagtgctgccaatcaccatccacggtgacgccgcag
tgaccgggcagggcgtggttcaggaaaccctgaacatgtcgaaagcgcgtggttatgaagttggcggtacggtacgt
atcgttatcaacaaccaggttggtttcaccacctctaatccgctggatgccgttctacgccgtactgtactgatat
cggtaagatggttcaggccccgattttccacgttaacgcggacgatccggaagccgttgcctttgtgaccgtctgg
cgctcgattttccgtaacacctttaaacgtgatGTTttcatcgacctggtgtgctaccgccgtcacggccaacgaa
gccgacgagccgagcgcaaccagccgctgatgtatcagaaaatcaaaaaacatccgacaccgcgcaaaatctacgc
tgacaagctggagcaggaaaaagtggcgacgtgaagatgccaccgagtggttaacctgtaccgcgatgcgctgg
atgctggcgattgcgtagtggcagagtggcgtccgatgaacatgcactctttcacctggtcgccgtacctcaaccac
gaatgggacgaagagtacccgaacaaagttgagatgaagcgcctgcaggagctggcgaaacgcatcagcacggtgcc
ggaagcagttgaaatgcagtctcgcgttgccaagatttatggcgatcgccaggcgatggctgccggtgagaaactgt

Sequences of Interest:

```
tcgactggggcggtgcggaaaacctcgcttacgccacgctggttgatgaaggcattccggttcgcctgtcgggtGAG
gactccggtcgcggtaccttcttccaccgccacgcggtgatccacaaccagtctaacggttccacttacacgccgct
gcaacatatccataacgggcagggcgcgttccgtgtctggagactccgtactgtctgaagaagcagtgctggcgttg
aatatggttatgccaccgcagaaccacgcactctgaccatctgggaagcgcagttcggtgacttcgccaacggtgcg
caggtggttatcgaccagttcatctcctctggcgaacagaaatggggccggatgtgtggtctggtgatgttgctgcc
gcacggttacgaagggcaggggccggagcactcctccgcgcgtctggaacgttatctgcaactttgtgctgagcaaa
acatgcaggtttgcgtaccgtctaccccggcacaggtttaccacatgctgcgtcgtcaggcgctgcgcgggatgcgt
cgtccgctggtcgtgatgtcgccgaaatccctgctgcgtcatccgctggcggtttccagcctcgaagaactggcgaa
cggcaccttcctgccagccatcggtgaaatcgacgagcttgatccgaagggcgtgaagcgcgtagtgatgtgttctg
gtaaggtttattacgacctgctggaacagcgtcgtaagaacaatcaacacgatgtcgccattgtgcgtatcgagcaa
ctctacccgttcccgcataaagcgatgcaggaagtgttgcagcagtttgctcacgtcaaggattttgtctggtgcca
ggaagagccgctcaaccagggcgcatggtactgcagccagcatcatttccgtgaagtgattccgtttggggcttctc
tgcgttatgcaggccgccggcctccgcctctccggcggtagggtatatgtccgttcaccagaaacagcaacaagat
ctggttaatgacgcgctgaacgtcgaataaataaaggatacacaatgagtagcgtagatattctggtccctgacctg
cctgaatccgtagccgatgccaccgtcgcaacctggcataaaaaaccggcgacgcagtcgtacgtgatgaagtgct
ggtagaaatcgaaactgacaaagtggtactggaagtaccggcatcagcagacggcattctggatgcggttctggaag
atgaaggtacaacggtaacgtctcgtcagatccttggtcgcctgcgtgaaggcaacagcgccggtaaagaaaccagc
gccaaatctgaagagaaagcgtccactccggcgcaacgccagcaggcgtctctggaagagcaaaacaacgatgcgtt
aagcccggcgatccgtcgcctgctggctgaacacaatctcgacgccagcgccattaaaggcaccggtgtgggtggtc
gtctgactcgtgaagatgtggaaaaacatctggcgaaagccccggcgaaagagtctgctccggcagcggctgctccg
gcggcgcaaccggctctggctgcacgtagtgaaaaacgtgtcccgatgactcgcctgcgtaagcgtgtggcagagcg
tctgctggaagcgaaaaactccaccgccatgctgaccacgttcaacgaagtcaacatgaagccgattatggatctgc
gtaagcagtacggtgaagcgtttgaaaaacgccacgcatccgtctgggctttatgtccttctacgtgaaagcggtg
gttgaagccctgaaacgttacccggaagtgaacgcttctatcgacggcgatgacgtggttttaccacaactattcga
cgtcagcatggcggtttctacgccgcgcggcctggtgacgccggttctgcgtgatgtcgatacctcggcatggcag
acatcgagaagaaatcaaagagctggcagtcaaaggccgtgacggcaagctgaccgttgaagatctgaccggtggt
aacttcaccatcaccaacggtggtgtgttcggttccctgatgtctacgccgatcatcaacccgccgcagagcgcaat
tctgggtatgcacgctatcaaagatcgtccgatggcggtgaatggtcaggttgagatcctgccgatgatgtacctgg
cgctgtcctacgatcaccgtctgatcgatggtcgcgaatccgtgggcttcctggtaacgatcaaagagttgctggaa
gatccgacgcgtctgctgctggacgtgtagtagtttaagtttcacctgcactgtagaccggataaggcattatcgcc
ttctccggcaattgaagcctgatgcgacgctgacgcgtcttatcaggcctacgggaccaccaatgtaggtcggataa
ggcgcaagcgccgcatccgacaagcgatgcctgatgtgacgtttaacgtgtcttatcaggcctacgggtgaccgaca
atgcccggaagcgatacgaaatattcGGTCTACGGTTTAAAAGATAACGATTACTGAAGGATGGACAGAACACatga
acttacatgaatatcaggcaaaacaactttttgcccgctatggcttaccagcaccggtgggttatgcctgtactact
ccgcgcgaagcagaagaagccgcttcaaaaatcggtgccggtccgtgggtagtgaaatgtcaggttcacgctggtgg
ccgcggtaaagcgggcggtgtgaaagttgtaaacagcaaaGAGgacatccgtgcttttgcagaaaactggctgggca
agcgtctggtaacgtatcaaacagatgccaatggccaaccggttaaccagattctggttgaagcagcgaccgatatc
gctaaagagctgtatctcggtgccgttgttgaccgtagttccgtcgtgtggtctttatggcctccaccgaaggcgg
cgtggaaatcgaaaagtggcggaagaaactccgcacctgatccataaagttgcgcttgatccgctgactggcccga
tgccgtatcagggacgcgagctggcgttcaaactgggtctggaaggtaaactggttcagcagttcaccaaaatcttc
atgggcctggcgaccattttcctggagccgctggcgttgatcgaaatcaaccgctgcgatcatcaccaaacaggg
cgatctgatttgcctcgacggcaaactgggcgctgacggcaacgcactgttccgccagcctgatctgcgcgaaatgc
gtgaccagtcgcaggaagatccgcgtgaagcacaggctgcacagtgggaactgaactacgttgcgctggacggtaac
atcggttgtatggttaacggcgcaggtctggcgatgggtacgatggacatcgttaaactgcacggcggcgaaccggc
taacttccttgacgttggcggcggcgcaaccaaagaacgtgtaaccgaagcgttcaaaatcatcctctctgacgaca
aagtgaaagccgttctggttaacatcttcggcggtatcgttcgttgcgacctgatcgctgacggtatcatcggcgcg
gtagcagaagtgggtgttaacgtaccggtcgtggtacgtctggaaggtaacaacgccgaactcggcgcgaagaaact
ggctgacagcggcctgaatattattgcagcaaaaggtctgacggatgcagctcagcaggttgttgccgcagtggagg
ggaaataatgtccattttaatcgataaaaaccaccaaggttatctgccagggcttttaccggtagccaggggacttttcc
actcagaacaggccattgcatacggcactaaaatggttggcggcgtaaccccaggtaaaggcggcaccacccacctc
ggcctgccggtgttcaacaccgtgcgtgaagccgttgctgccactggcgctaccgcttctgttatctacgtaccagc
accgttctgcaaagactccattctggaagccatcgacgcaggcatcaaactgattatcaccatcactgaaggcatcc
cgacgctggatatgctgaccgtgaaagtgaagctggatgaagcaggcgttcgtatgatcggcccgaactgcccaggc
gttatcactccgggtgaatgcaaaatcggtatccagcctggtcacattcacaaaccgggtaaagtgggtatcgtttc
ccgttccggtacactgacctatgaagcggttaaacagaccacggattacggtttcggtcagtcgacctgtgtcggta
tcggcggtgacccgatcccgggctctaactttatcgacattctcgaaatgttcgaaaaagatccgcagaccgaagcg
atcgtgatgatcggtgagatcggcggtagcgctgaagaagaagcagctgcgtacatcaaagagcacgttaccaagcc
agttgtgggttacatcgctggtgtgactgcgccgaaaggcaaacgtatgggccacgcgggtgccatcattgccggtg
ggaaagggactgcggatgagaaattcgctgctctggaagccgcaggcgtgaaaaccgttcgcagcctggcggatatc
ggtgaagcactgaaaactgttctgaaataaaggtccaggcatcaaataaaacgaaaggctcagtcgaaagactgggc
ctttcgttttatctgttgtttgtcggtgaacgctctctactagagtcacactggctcaccttcgggtgggcctttct
gcgtttatatcccgtcaagtcagcgtaatgctctgccagtgttacaaccaattaaccaattctgattagaaaaactc
atcgagcatcaaatgaaactgcaatttattcatatcaggattatcaataccatattttgaaaaagccgtttctgta
atgaaggagaaaactcaccgaggcagttccataggatggcaagatcctggtatcggtctgcgattccgactcgtcca
acatcaatacaacctattaatttccctcgtcaaaaataaggttatcaagtgagaaatcaccatgagtgacgactga
atccggtgagaatggcaaaagcttatgcatttctttccagacttgttcaacaggccagccattacgctcgtcatcaa
aatcactcgcatcaaccaaaccgttattcattcgtgattgcgcctgagcgagacgaaatacgcgatcgctgttaaaa
ggacaattacaaacaggaatcgaatgcaaccggcgcaggaacactgccagcgcatcaacaatattttcacctgaatc
aggatattcttctaatacctcggaatgctgttttcccggggatcgcagtggtgagtaaccatgcatcatcaggagtac
ggataaaatgcttgatggtcggaagaggcataaattccgtcagccagtttagtctgaccatctcatctgtaacatca
ttggcaacgctacctttgccatgtttcagaaacaactctggcgcatcgggcttcccatacaatcgatagattgtcgc
acctgattgcccgacattatcgcgagcccatttatacccatataaatcagcatccatgttggaatttaatcgcggcc
tggagcaagacgtttcccgttgaatatggctcataacaccccttgtattactgtttatgtaagcagacagttttatt
gttcatgatgatatatttttatcttgtgcaatgtaacatcagagattttgagacacaacgtggctttgttgaataaa
tcgaactttgctgagttgaaggatcagctcgagtgccacctgacgtctaagaaaccattattatcatgacattaac
ctataaaaataggcgtatcacgaggcagaatttcagataaaaaaaatccttagctttcgctaaggatgatttctgga
attcgcggccgcttctagagactagtggaagacatcgctggaaagtgaaacgtgatttcatgcgtcattttgaacat
```

-continued

Sequences of Interest:

tttgtaaatcttatttaataatgtgtgcggcaattcacatttaatttatgaatgttttcttaacatcgcggcaactc
aagaaacggcaggttcggatcttagctactagagaaagaggagaaatactagatgcgtaaaggcgaagagctgttca
ctggtgtcgtccctattctggtggaactggatggtgatgtcaacggtcataagttttccgtgcgtggcgagggtgaa
ggtgacgcaactaatggtaaactgacgctgaagttcatctgtactactggtaaactgccggttccttggccgactct
ggtaacgacgctgacttatggtgttcagtgctttgctcgttatccggaccatatgaagcagcatgacttcttcaagt
ccgccatgccggaaggctatgtgcaggaacgcacgatttcctttaaggatgacggcacgtacaaaacgcgtgcggaa
gtgaaatttgaaggcgatacccttggtaaaccgcattgagctgaaaggcattgactttaaagaggacggcaatatcct
gggccataagctggaatacaattttaacagccacaatgttttacatcaccgccgataaacaaaaaaatggcattaaag
cgaattttaaaattcgccacaacgtggaggatggcagcgtgcagctggctgatcactaccagcaaaacactccaatc
ggtgatggtcctgttctgctgccagacaatcactatctgagcacgcaaagcgttctgtctaaagatccgaacgagaa
acgcgatcatatggttctgctggagttcgtaaccgcagcgggcatcacgcatggtatggatgaactgtacaaatgac
caggcatcaaataaaacgaaaggctcagtcgaaagactgggcctttcgttttatctgttgtttgtcggtgaacgctc
tctactagagtcacactggctccacttcgggtgggcctttctgcgtttatacgtgccatgtcttctactagtagcgg
ccgctgcagtccggcaaaaaagggcaaggtgtcaccaccctgcccttttttctttaaaaccgaaaagattacttcgcg
ttatgcaggcttcctcgctcactgactcgctgcgctcggtcgttcggctgcggcgagcggtatcagctcactcaaag
gcggtaatacggttatccacagaatcagggggataacgcaggaaagaacatgtgagcaaaaggccagcaaaaggccag
gaaccgtaaaaaggc SEQ ID NO: 10. Sequence of Plasmid pDvK-SucBC, used for testing plasmid retention
in nonselective media
GGATGGACAGAACACATGAACTTACATGAATATCAGGCAAAACAACTTTTTGCCCGCTATGGCTTACCAGCACCGGT
GGGTTATGCCTGTACTACTCCGCGCGAAGCAGAAGAAGCCGCTTCAAAAATCGGTGCCGGTCCGTGGGTAGTGAAAT
GTCAGGTTCACGCTGGTGGCCGCGGTAAAGCGGGCGGTGTGAAAGTTGTAAACAGCAAAGAGGACATCCGTGCTTTT
GCAGAAAACTGGCTGGGCAAGCGTCTGGTAACGTATCAAACAGATGCCAATGGCCAACCGGTTAACCAGATTCTGGT
TGAAGCAGCGACCGATATCGCTAAAGAGCTGTATCTCGGTGCCGTTGTTGACCGTAGTTCCCGTCGTGTGGTCTTTA
TGGCCTCCACCGAAGGCGGCGTGGAAATCGAAAAGTGGCGGAAGAAACTCCGCACCTGATCCATAAAGTTGCGCTT
GATCCGCTGACTGGCCCGATGCCGTATCAGGGACGCGAGCTGGCGTTCAAACTGGGTCTGGAAGGTAAACTGGTTCA
GCAGTTCACCAAAATCTTCATGGGCCTGGCGACCATTTTCCTGGAGCGCGACCTGGCGTTGATCGAAATCAACCCGC
TGGTCATCACCAAACAGGGCGATCTGATTTGCCTCGACGGCAAACTGGGCGCTGACGGCAACGCACTGTTCCGCCAG
CCTGATCTGCGCGAAATGCGTGACCAGTCGCAGGAAGATCCGCGTGAAGCACAGGCTGCACAGTGGGAACTGAACTA
CGTTGCGCTGGACGGTAACATCGGTTGTATGGTTAACGGCGCAGGTCTGGCGATGGGTACGATGGACATCGTTAAAC
TGCACGGCGGCGAACCGGCTAACTTCCTTGACGTTGGCGGCGGCAACCAAAGAACGTGTAACCGAAGCGTTCAAA
ATCATCCTCTCTGACGACAAAGTGAAAGCCGTTCTGGTTAACATCTTCGGCGGTATCGTTCGTTGCGACCTGATCGC
TGACGGTATCATCGGCGCGGTAGCAGAAGTGGGTGTTAACGTACCGGTCGTGGTACGTCTGGAAGGTAACAACGCCG
AACTCGGCGCGAAGAAACTGGCTGACAGCGGCCTGAATATTATTGCAGCAAAAGGTCTGACGGATGCAGCTCAGCAG
GTTGTTGCCGCAGTGGAGGGGAAATAAAGGTCCAGGCATCAAATAAAACGAAAGGCTCAGTCGAAAGACTGGGCCTT
TCGTTTTATCTGTTGTTTGTCGGTGAACGCTCTCTACTAGAGTCACACTGGCTCACCTTCGGGTGGGCCTTTCTGCG
TTTATAGCTTATGTCTTCTACTAGTAGCGGCCGCTGCAGTCCGGCAAAAAAGGGCAAGGTGTCACCACCCTGCCCTT
TTTCTTTAAAACCGAAAAGATTACTTCGCGTTATGCAGGCTTCCTCGCTCACTGACTCGCTGCGCTCGGTCGTTCGG
CTGCGGCGAGCGGTATCAGCTCACTCAAAGGCGGTAATACGGTTATCCACAGAATCAGGGGATAACGCAGGAAAGAA
CATGTGAGCAAAAGGCCAGCAAAAGGCCAGGAACCGTAAAAAGGCCGCGTTGCTGGCGTTTTTCCACAGGCTCCGCC
CCCCTGACGAGCATCACAAAAATCGACGCTCAAGTCAGAGGTGGCGAAACCCGACAGGACTATAAAGATACCAGGCG
TTTCCCCCTGGAAGCTCCCTCGTGCGCTCTCCTGTTCCGACCCTGCCGCTTACCGGATACCTGTCCGCCTTTCTCCC
TTCGGGAAGCGTGGCGCTTTCTCATAGCTCACGCTGTAGGTATCTCAGTTCGGTGTAGGTCGTTCGCTCCAAGCTGG
GCTGTGTGCACGAACCCCCCGTTCAGCCCGACCGCTGCGCCTTATCCGGTAACTATCGTCTTGAGTCCAACCCGGTA
AGACACGACTTATCGCCACTGGCAGCAGCCACTGGTAACAGGATTAGCAGAGCGAGGTATGTAGGCGGTGCTACAGA
GTTCTTGAAGTGGTGGCCTAACTACGGCTACACTAGAAGAACAGTATTTGGTATCTGCGCTCTGCTGAAGCCAGTTA
CCTTCGGAAAAAGAGTTGGTAGCTCTTGATCCGGCAAACAAACCACCGCTGGTAGCGGTGGTTTTTTTGTTTGCAAG
CAGCAGATTACGCGCAGAAAAAAAGGATCTCAAGAAGATCCTTTGATCTTTTCTACGGGGTCTGACGCTCAGTGGAA
CGAAAACTCACGTTAAGGGATTTTGGTCATGAGATTATCAAAAAGGATCTTCACCTAGATCCTTTTAAATTAAAAT
GAAGTTTTAAATCAATCTAAAGTATATATGAGTAAACTTGGTCTGACAGCTCGAGTCCCGTCAAGTCAGCGTAATGC
TCTGCCAGTGTTACAACCAATTAACCAATTCTGATTAGAAAAACTCATCGAGCATCAAATGAAACTGCAATTTATTC
ATATCAGGATTATCAATACCATATTTTTGAAAAAGCCGTTTCTGTAATGAAGGAGAAAACTCACCGAGGCAGTTCCA
TAGGATGGCAAGATCCTGGTATCGGTCTGCGATTCCGACTCGTCCAACATCAATACAACCTATTAATTTCCCCTCGT
CAAAAATAAGGTTATCAAGTGAGAAATCACCATGAGTGACGACTGAATCCGGTGAGAATGGCAAAAGCTTATGCATT
TCTTTCCAGACTTGTTCAACAGGCCAGCCATTACGCTCGTCATCAAAATCACTCGCATCAACCAAACCGTTATTCAT
TCGTGATTGCGCCTGAGCGAGACGAAATACGCGATCGCTGTTAAAAGGACAATTACAAACAGGAATCGAATGCAACC
GGCGCAGGAACACTGCCAGCGCATCAACAATATTTTCACCTGAATCAGGATATTCTTCTAATACCTGGAATGCTGTT
TTCCCGGGGATCGCAGTGGTGAGTAACCATGCATCATCAGGAGTACGGATAAAATGCTTGATGGTCGGAAGAGGCAT
AAATTCCGTCAGCCAGTTTAGTCTGACCATCTCATCTGTAACATCATTGGCAACGCTACCTTTGCCATGTTTCAGAA
ACAACTCTGGCGCATCGGGCTTCCCATACAATCGATAGATTGTCGCACCTGATTGCCCGACATTATCGCGAGCCCAT
TTATACCCATATAAATCAGCATCCATGTTGGAATTTAATCGCGGCCTCGAGCAAGACGTTTCCCGTTGAATATGGCT
CATAACACCCCTTGTATTACTGTTTATGTAAGCAGACAGTTTTATTGTTCATGATGATATATTTTTATCTTGTGCAA
TGTAACATCAGAGATTTTGAGACACAACGTGGCTTTGTTGAATAAATCGAACTTTTGCTGAGTTGAAGGATCAGCTC
GAGTGCCACCTGACGTCTAAGAAACCATTATTATCATGACATTAACCTATAAAAATAGGCGTATCACGAGGCAGAAT
TTCAGATAAAAAAAATCCTTAGCTTTCGCTAAGGATGATTTCTGGAATTCGCGGCCGCTTCTAGAGACTAGTGGGAAG
ACATGGAGTTTACGGCTAGCTCAGTCCTAGGTATAGTGCTAGCTACTTGTTAGAAAAGAGAAGCACGTAATGAGTAG
CGTAGATATTCTGGTCCCTGACCTGCCTGAATCCGTAGCCGATGCCACCGTCGCAACCTGGCATAAAAAACCCGGCG
ACGCAGTCGTACGTGATGAAGTGCTGGTAGAAATCGAAACTGACAAAGTGGTACTGGAAGTACCGGCATCAGCAGAC
GGCATTCGGATGCGGTTCTGGAAGATGAAGGTACAACGGTAACGTCTCGTCAGATCCTTGGTCGCCTGCGTGAAGG
CAACAGCGCCGGTAAAGAAACCAGCGCCAAATCTGAAGAGAAAACTGCCACTCCGGCGCAACGCCAGCAGGCGTCTC
TGGAAGAGCAAAACAACGATGCGTTAAGCCCGGCGATCCGTCGCCTGCTGGCTGAACACAATCTCGACGCCAGCGCC
ATTAAAGGCACCGGTGTGGGTGGTCGTCTGACTCGTGAAGATGTGGAAAAACATCTGGCGAAAGCCCCGGCGAAAGA
GTCTGCTCCGGCAGCGGCTGCTCCGGCGGCGCAACCGGCTCTGGCTGCACGTAGTGAAAAACGTGTCCCGATGACTC
GCCTGCGTAAGCGTGTGGCAGAGCGTCTGCTGGAAGCGAAAAACTCCACCGCCATGCTGACCACGTTCAACGAAGTC
AACATGAAGCCGATTATGGATCTGCGTAAGCAGTACGGTGAAGCGTTTGAAAAACGCCACGGCATCCGTCTGGGCTT
TATGTCCTTCTACGTGAAAGCGGTGGTTGAAGCCCTGAAACGTTACCCGGAAGTGAACGCTTCTATCGACGGCGATG

Sequences of Interest:

```
ACGTGGTTTACCACAACTATTTCGACGTCAGCATGGCGGTTTCTACGCCGCGCGGCCTGGTGACGCCGGTTCTGCGT
GATGTCGATACCCTCGGCATGGCAGACATCGAGAAGAAAATCAAAGAGCTGGCAGTCAAAGGCCGTGACGGCAAGCT
GACCGTTGAAGATCTGACCGGTGGTAACTTCACCATCACCAACGGTGGTGTGTTCGGTTCCCTGATGTCTACGCCGA
TCATCAACCCGCCGCAGAGCGCAATTCTGGGTATGCACGCTATCAAAGATCGTCCGATGGCGGTGAATGGTCAGGTT
GAGATCCTGCCGATGATGTACCTGGCGCTGTCCTACGATCACCGTCTGATCGATGGTCGCGAATCCGTGGGCTTCCT
GGTAACGATCAAAGAGTTGCTGGAAGATCCGACGCGTCTGCTGCTGGACGTGTAGTAGTTTAAGTTTCACCTGCACT
GTAGACCGGATAAGGCATTATCGCCTTCTCCGGCAATTGAAGCCTGATGCGACGCTGACGCGTCTTATCAGGCCTAC
GGGACCACCAATGTAGGTCGGATAAGGCGCAAGCGCCGCATCCGACAAGCGATGCCTGATGTGACGTTTAACGTGTC
TTATCAGGCCTACGGGTGACCGACAATGCCCGGAAGCGATACGAAATATTCGGTCTACGGTTTAAAAGATAACGATT
ACTGAA
```

---

What is claimed is:

1. A transformed bacterial cell adapted to maintain one or more extrachromosomal elements in its daughter cells, comprising:
   (a) a first deletion, disruption, or mutation that reduces or eliminates the activity of a first chromosomal gene responsible for expressing a first essential enzyme in the succinate pathway, and a second deletion, disruption, or mutation that reduces or eliminates the activity of a second chromosomal gene responsible for expressing a second essential enzyme in the succinate pathway;
   (b) one or more extrachromosomal elements, wherein each of the one or more extrachromosomal elements comprises a DNA sequence that is capable of expressing a recombinant protein of interest and lacks an antibiotic resistance gene; and
   (c) the one or more extrachromosomal elements of (b) further comprise complementing genes that collectively replace the respective functions of the first and second chromosomal genes in their expression of the first and second essential enzymes whereby desired cellular maintenance of the one or more chromosomal elements is achieved;
   wherein the first essential enzyme is a 2-oxoglutarate dehydrogenase and the first chromosomal gene is either sucA or sucB; and
   wherein the second essential enzyme is a succinyl-CoA synthetase and the second chromosomal gene is either sucC or sucD.

2. The transformed bacterial cell of claim 1, wherein each of the one or more extrachromosomal elements is a plasmid.

3. The transformed bacterial cell of claim 1, wherein the transformed bacterial cell comprises deletions of the first chromosomal gene and the second chromosomal gene.

4. The transformed bacterial cell of claim 1, wherein the transformed bacterial cell comprises a chromosomal deletion of: sucAD, sucAC, sucBC, or sucBD.

5. The transformed bacterial cell of claim 4, wherein the transformed bacterial cell comprises a quadruple sucABCD deletion.

6. The transformed bacterial cell of claim 5, comprising a first plasmid comprising the complementing genes sucAD, and a second plasmid comprising the complementing genes sucBC.

7. The transformed bacterial cell of claim 5, comprising a first plasmid comprising the complementing genes sucAC, and a second plasmid comprising the complementing genes sucBD.

8. The transformed bacterial cell of claim 6, wherein the first plasmid comprises a DNA sequence that encodes a first recombinant protein of interest, and the second plasmid comprises a DNA sequence that encodes a second recombinant protein of interest that is different from the first protein of interest.

9. The transformed bacterial cell of claim 5, comprising four plasmids each comprising a DNA sequence that encodes a different recombinant protein of interest and each comprising a different complementing gene for the quadruple sucABCD deletion.

10. The transformed bacterial cell of claim 1, wherein the transformed bacterial cell is a bacterium that has a peptidoglycan cell wall.

11. The transformed bacterial cell of claim 1, wherein the transformed bacterial cells is selected from a group consisting of: a *Escherichia coli* cell; *Corynebacterium* spp., *Vibrio* spp.; *Escherichia* spp.; *Enterobacter* spp.; *Citrobacter* spp.; *Erwinia* spp.; *Bacillus* spp.; *Pseudomonas* spp.; Cyanobacteria spp.; *Salmonella* spp. and *Klebsiella* spp.

* * * * *

SEQUENCE LISTING

<160> NUMBER OF SEQ ID NOS: 10

<210> SEQ ID NO 1
<211> LENGTH: 9001
<212> TYPE: DNA
<213> ORGANISM: Escherichia coli

<400> SEQUENCE: 1

| | | | | | |
|---|---|---|---|---|---|
| ccggtcaggc | actgactgtg | aatgagaaag | gcgaagatgt | ggttgttccg | ggactgtttg | 60 |
| ccgttggtga | aatcgcttgt | gtatcggtac | acggcgctaa | ccgtctgggc | ggcaactcgc | 120 |
| tgctggacct | ggtggtcttt | ggtcgcgcgg | caggtctgca | tctgcaagag | tctatcgccg | 180 |
| agcagggcgc | actgcgcgat | gccagcgagt | ctgatgttga | agcgtctctg | gatcgcctga | 240 |
| accgctggaa | caataatcgt | aacggtgaag | atccggtggc | gatccgtaaa | gcgctgcaag | 300 |
| aatgtatgca | gcataacttc | tcggtcttcc | gtgaaggtga | tgcgatggcg | aaagggcttg | 360 |
| agcagttgaa | agtgatccgc | gagcgtctga | aaaatgcccg | tctggatgac | acttccagcg | 420 |
| agttcaacac | ccagcgcgtt | gagtgcctgg | aactggataa | cctgatggaa | acggcgtatg | 480 |
| caacggctgt | ttctgccaac | ttccgtaccg | aaagccgtgg | cgcgcatagc | cgcttcgact | 540 |
| tcccggatcg | tgatgatgaa | aactggctgt | gccactccct | gtatctgcca | gagtcggaat | 600 |
| ccatgacgcg | ccgaagcgtc | aacatggaac | cgaaactgcg | cccggcattc | ccgccgaaga | 660 |
| ttcgtactta | ctaatgcgga | gacaggaaaa | tgagactcga | gttttcaatt | tatcgctata | 720 |
| acccggatgt | tgatgatgct | ccgcgtatgc | aggattacac | cctggaagcg | gatgaaggtc | 780 |
| gcgacatgat | gctgctggat | gcgcttatcc | agctaaaaga | gaaagatccc | agcctgtcgt | 840 |
| tccgccgctc | ctgccgtgaa | ggtgtgtgcg | gttccgacgg | tctgaacatg | aacggcaaga | 900 |
| atggtctggc | ctgtattacc | ccgatttcgg | cactcaacca | gccgggcaag | aagattgtga | 960 |
| ttcgcccgct | gccaggttta | ccggtgatcc | gcgatttggt | ggtagacatg | ggacaattct | 1020 |
| atgcgcaata | tgagaaaatt | aagccttacc | tgttgaataa | tggacaaaat | ccgccagctc | 1080 |
| gcgagcattt | acagatgcca | gagcagcgcg | aaaaactcga | cgggctgtat | gaatgtattc | 1140 |
| tctgcgcatg | ttgttcaacc | tcttgtccgt | ctttctggtg | gaatcccgat | aagtttatcg | 1200 |
| gcccggcagg | cttgttagcg | gcatatcgtt | tcctgattga | tagccgtgat | accgagactg | 1260 |
| acagccgcct | cgacggtttg | agtgatgcat | tcagcgtatt | ccgctgtcac | agcatcatga | 1320 |
| actgcgtcag | tgtatgtccg | aaggggctga | acccgacgcg | cgccatcggc | catatcaagt | 1380 |
| cgatgttgtt | gcaacgtaat | gcgtaaaccg | taggcctgat | aagacgcgca | agcgtcgcat | 1440 |
| caggcaacca | gtgccggatg | cggcgtgaac | gccttatccg | gcctacaagt | cattacccgt | 1500 |
| aggcctgata | agcgcagcgc | atcaggcgta | acaaagaaat | gcaggaaatc | tttaaaaact | 1560 |

```
gcccctgaca ctaagacagt ttttaaaggt tccttcgcga gccactacgt agacaagagc   1620
tcgcaagtga accccggcac gcacatcact gtgcgtggta gtatccacgg cgaagtaagc   1680
ataaaaaaga tgcttaaggg atcacgatgc agaacagcgc tttgaaagcc tggttggact   1740
cttcttacct ctctggcgca aaccagagct ggatagaaca gctctatgaa gacttcttaa   1800
ccgatcctga ctcggttgac gctaactggc gttcgacgtt ccagcagtta cctggtacgg   1860
gagtcaaacc ggatcaattc cactctcaaa cgcgtgaata tttccgccgc ctggcgaaag   1920
acgcttcacg ttactcttca acgatctccg accctgacac caatgtgaag caggttaaag   1980
tcctgcagct cattaacgca taccgcttcc gtggtcacca gcatgcgaat ctcgatccgc   2040
tgggactgtg gcagcaagat aaagtggccg atctggatcc gtctttccac gatctgaccg   2100
aagcagactt ccaggagacc ttcaacgtcg gttcatttgc cagcggcaaa gaaaccatga   2160
aactcggcga gctgctggaa gccctcaagc aaacctactg cggcccgatt ggtgccgagt   2220
atatgcacat taccagcacc gaagaaaaac gctggatcca acagcgtatc gagtctggtc   2280
gcgcgacttt caatagcgaa gagaaaaaac gcttcttaag cgaactgacc gccgctgaag   2340
gtcttgaacg ttacctcggc gcaaaattcc ctggcgcaaa acgcttctcg ctggaaggcg   2400
gtgacgcgtt aatcccgatg cttaaagaga tgatccgcca cgctggcaac agcggcaccc   2460
gcgaagtggt tctcgggatg cgcaccgtg tcgtctgaa cgtgctggtg aacgtgctgg   2520
gtaaaaaacc gcaagacttg ttcgacgagt tcgccggtaa acataaagaa cacctcggca   2580
cgggtgacgt gaaataccac atgggcttct cgtctgactt ccagaccgat ggcggcctgg   2640
tgcacctggc gctggcgttt aacccgtctc accttgagat tgtaagcccg gtagttatcg   2700
gttctgttcg tgcccgtctg gacagacttg atgagccgag cagcaacaaa gtgctgccaa   2760
tcaccatcca cggtgacgcc gcagtgaccg ggcagggcgt ggttcaggaa accctgaaca   2820
tgtcgaaagc gcgtggttat gaagttggcg gtacggtacg tatcgttatc aacaaccagg   2880
ttggtttcac cacctctaat ccgctggatg cccgttctac gccgtactgt actgatatcg   2940
gtaagatggt tcaggccccg attttccacg ttaacgcgga cgatccggaa gccgttgcct   3000
ttgtgacccg tctggcgctc gatttccgta acacctttaa acgtgatgtc ttcatcgacc   3060
tggtgtgcta ccgccgtcac ggccacaacg aagccgacga gccgagcgca acccagccgc   3120
tgatgtatca gaaaatcaaa aaacatccga caccgcgcaa aatctacgct gacaagctgg   3180
agcaggaaaa agtggcgacg ctggaagatg ccaccgagat ggttaacctg taccgcgatg   3240
cgctggatgc tggcgattgc gtagtggcag agtggcgtcc gatgaacatg cactcttttca   3300 cctggtcgcc gtacctcaac cacgaatggg acgaagagta cccgaacaaa gttgagatga   3360
agcgcctgca ggagctggcg aaacgcatca gcacggtgcc ggaagcagtt gaaatgcagt   3420
ctcgcgttgc caagatttat ggcgatcgcc aggcgatggc tgccggtgag aaactgttcg   3480
actggggcgg tgcggaaaac ctcgcttacg ccacgctggt tgatgaaggc attccggttc   3540
gcctgtcggg tgaagactcc ggtcgcgta ccttcttcca ccgccacgcg gtgatccaca   3600
accagtctaa cggttccact tacacgccgc tgcaacatat ccataacggg cagggcgcgt   3660
tccgtgtctg ggactccgta ctgtctgaag aagcagtgct ggcgtttgaa tatggttatg   3720
ccaccgcaga accacgcact ctgaccatct gggaagcgca gttcggtgac ttcgccaacg   3780
gtgcgcaggt ggttatcgac cagttcatct cctctggcga acagaaatgg ggccggatgt   3840
gtggtctggt gatgttgctg ccgcacggtt acgaagggcg ggggccggag cactcctccg   3900
cgcgtctgga acgttatctg caactttgtg ctgagcaaaa catgcaggtt tgcgtaccgt   3960
```

```
ctaccccggc acaggtttac cacatgctgc gtcgtcaggc gctgcgcggg atgcgtcgtc      4020
cgctggtcgt gatgtcgccg aaatccctgc tgcgtcatcc gctggcggtt ccagcctcg       4080
aagaactggc gaacggcacc ttcctgccag ccatcggtga aatcgacgag cttgatccga      4140
agggcgtgaa gcgcgtagtg atgtgttctg gtaaggttta ttacgacctg ctggaacagc      4200
gtcgtaagaa caatcaacac gatgtcgcca ttgtgcgtat cgagcaactc tacccgttcc      4260
cgcataaagc gatgcaggaa gtgttgcagc agtttgctca cgtcaaggat tttgtctggt      4320
gccaggaaga gccgctcaac cagggcgcat ggtactgcag ccagcatcat ttccgtgaag      4380
tgattccgtt tggggcttct ctgcgttatg caggccgccc ggcctccgcc tctccggcgg      4440
tagggtatat gtccgttcac cagaaacagc aacaagatct ggttaatgac gcgctgaacg      4500
tcgaataaat aaaggataca caatgagtag cgtagatatt ctggtccctg acctgcctga      4560
atccgtagcc gatgccaccg tcgcaacctg gcataaaaaa cccggcgacg cagtcgtacg      4620
tgatgaagtg ctggtagaaa tcgaaactga caaagtggta ctggaagtac cggcatcagc      4680
agacggcatt ctggatgcgg ttctggaaga tgaaggtaca acggtaacgt ctcgtcagat      4740
ccttggtcgc ctgcgtgaag gcaacagcgc cggtaaagaa accagcgcca atctgaaga       4800
gaaagcgtcc actccggcgc aacgccagca ggcgtctctg gaagagcaaa caacgatgc       4860
gttaagcccg gcgatccgtc gcctgctggc tgaacacaat ctcgacgcca gcgccattaa      4920
aggcaccggt gtgggtggtc gtctgactcg tgaagatgtg gaaaaacatc tggcgaaagc      4980
cccggcgaaa gagtctgctc cggcagcggc tgctccggcg gcgcaaccgg ctctggctgc      5040
acgtagtgaa aaacgtgtcc cgatgactcg cctgcgtaag cgtgtggcag agcgtctgct      5100
ggaagcgaaa aactccaccg ccatgctgac cacgttcaac gaagtcaaca tgaagccgat      5160
tatggatctg cgtaagcagt acggtgaagc gtttgaaaaa cgccacggca tccgtctggg      5220
ctttatgtcc ttctacgtga aagcggtggt tgaagccctg aaacgttacc cggaagtgaa      5280
cgcttctatc gacggcgatg acgtggttta ccacaactat ttcgacgtca gcatggcggt      5340
ttctacgccg cgcggcctgg tgacgccggt tctgcgtgat gtcgataccc tcggcatggc      5400
agacatcgag aagaaaatca aagagctggc agtcaaaggc cgtgacggca agctgaccgt      5460
tgaagatctg accggtggta acttcaccat caccaacggt ggtgtgttcg gttccctgat      5520
gtctacgccg atcatcaacc cgccgcagag cgcaattctg ggtatgcacg ctatcaaaga      5580
tcgtccgatg gcggtgaatg gtcaggttga gatcctgccg atgatgtacc tggcgctgtc      5640
ctacgatcac cgtctgatcg atggtcgcga atccgtgggc ttcctggtaa cgatcaaaga      5700
gttgctggaa gatccgacgc gtctgctgct ggacgtgtag tagtttaagt ttcacctgca      5760
ctgtagaccg gataaggcat tatcgccttc tccggcaatt gaagcctgat gcgacgctga      5820
cgcgtcttat caggcctacg ggaccaccaa tgtaggtcgg ataaggcgca agcgccgcat      5880
ccgacaagcg atgcctgatg tgacgtttaa cgtgtcttat caggcctacg ggtgaccgac      5940
aatgcccgga agcgatacga aatattcggt ctacggttta aaagataacg attactgaag      6000
gatggacaga acacatgaac ttacatgaat atcaggcaaa acaactttt gcccgctatg       6060
gcttaccagc accggtgggt tatgcctgta ctactccgcg cgaagcagaa gaagccgctt      6120
caaaaatcgg tgccggtccg tgggtagtga aatgtcaggt tcacgctggt ggccgcggta      6180
aagcgggcgg tgtgaaagtt gtaaacagca agaagacat ccgtgctttt gcagaaaact       6240
ggctgggcaa gcgtctggta acgtatcaaa cagatgccaa tggccaaccg gttaaccaga      6300
ttctggttga agcagcgacc gatatcgcta aagagctgta tctcggtgcc gttgttgacc      6360
```

```
gtagttcccg tcgtgtggtc tttatggcct ccaccgaagg cggcgtggaa atcgaaaaag    6420
tggcggaaga aactccgcac ctgatccata aagttgcgct tgatccgctg actggcccga    6480
tgccgtatca gggacgcgag ctggcgttca aactgggtct ggaaggtaaa ctggttcagc    6540
agttcaccaa aatcttcatg ggcctggcga ccatttttcct ggagcgcgac ctggcgttga    6600
tcgaaatcaa cccgctggtc atcaccaaac agggcgatct gatttgcctc gacggcaaac    6660
tgggcgctga cggcaacgca ctgttccgcc agcctgatct cgcgaaatg cgtgaccagt    6720
cgcaggaaga tccgcgtgaa gcacaggctg cacagtggga actgaactac gttgcgctgg    6780
acggtaacat cggttgtatg gttaacggcg caggtctggc gatgggtacg atggacatcg    6840
ttaaactgca cggcggcgaa ccggctaact tccttgacgt tggcggcggc gcaaccaaag    6900
aacgtgtaac cgaagcgttc aaaatcatcc tctctgacga caaagtgaaa gccgttctgg    6960
ttaacatctt cggcggtatc gttcgttgcg acctgatcgc tgacggtatc atcggcgcgg    7020
tagcagaagt gggtgttaac gtaccggtcg tggtacgtct ggaaggtaac aacgccgaac    7080
tcggcgcgaa gaaactggct gacagcgcc tgaatattat tgcagcaaaa ggtctgacgg    7140
atgcagctca gcaggttgtt gccgcagtgg aggggaaata atgtccatt taatcgataa    7200
aaacaccaag gttatctgcc agggctttac cggtagccag gggacttcc actcagaaca    7260
ggccattgca tacggcacta aaatggttgg cggcgtaacc ccaggtaaag gcggcaccac    7320
ccacctcggc ctgccggtgt caacaccgt gcgtgaagcc gttgctgcca ctggcgctac    7380
cgcttctgtt atctacgtac cagcaccgtt ctgcaaagac tccattctgg aagccatcga    7440
cgcaggcatc aaactgatta tcaccatcac tgaaggcatc ccgacgctgg atatgctgac    7500
cgtgaaagtg aagctggatg aagcaggcgt tcgtatgatc ggcccgaact gcccaggcgt    7560
tatcactccg ggtgaatgca aaatcggtat ccagcctggt cacattcaca accgggtaa    7620
agtgggtatc gtttcccgtt ccggtacact gacctatgaa gcggttaaac agaccacgga    7680
ttacggtttc ggtcagtcga cctgtgtcgg tatcggcggt gacccgatcc cgggctctaa    7740
ctttatcgac attctcgaaa tgttcgaaaa agatccgcag accgaagcga tcgtgatgat    7800
cggtgagatc ggcggtagcg ctgaagaaga agcagctgcg tacatcaaag agcacgttac    7860
caagccagtt gtgggttaca tcgctggtgt gactgcgccg aaaggcaaac gtatgggcca    7920
cgcgggtgcc atcattgccg gtgggaaagg gactgcggat gagaaattcg ctgctctgga    7980
agccgcaggc gtgaaaaccg ttcgcagcct ggcggatatc ggtgaagcac tgaaaactgt    8040
tctgaaataa atatctgtaa taagaaatag ccctcgccgc ttccctctac aggaatggcg    8100
aagggctgtc ggtttcgaca tggttggcca tcgtatgatg gcctttttg tgcttatcgc    8160
gatgattttc gctgcgctat cagggtaaat ttatagtcat cggtattaaa agcgttgcgg    8220
ctatattcaa acacccgacc atcaactaaa tatccacgcg atacttttc aagaatcggc    8280
tttgtctggc tgatattaag cagacggctc atctcttcgg ttggcatcag aggaatgatt    8340
tcctgttcgc tacgatcgat aaccatttc ttcacttctt cgataaagtg atatttcgaa    8400
ttttccatga cctgccaggt gagatccggg aacaacgcaa gcggcatcca ggtttcttcc    8460
agcgccattg gcttttgctt gcgatagcgc acgcgcttca catgccacac acgatcctgc    8520
gggtgatttt gtagctgttg ctgaagaaaa tcgtcagccg gaatcacttc gaatatcaga    8580
acttcactgt gtgtatcgac gtgacggtcc gacagttttt catcaaaact ggttaactga    8640
aaaatatcgt aattgacccg ctcttctttg acgtaagtcc cgctgccctg aatgctttcg    8700
aggatctgct gctcgactag ctggcgcaaa gcctgacgca ccgtaacccg gctgacgcca    8760
```

```
aactctgtttt gtagcgctga ttcagtgggt aacgcatcgc caggtttaag ctcgccacgc    8820
gcaatttgtt cacgaatgcg atcggcaatc tgccggtata agggcttgtg tcccattttt    8880
agtatctcat taatacgaat ttaaccatta tgcccgataa attcatcctg taaataatac    8940
aaatacaata caaataattt caatcaagtg aaattgatca cataatggta ttgttttatc    9000
g                                                                    9001
```

<210> SEQ ID NO 2
<211> LENGTH: 6753
<212> TYPE: DNA
<213> ORGANISM: Escherichia coli

<400> SEQUENCE: 2

```
ccggtcaggc actgactgtg aatgagaaag gcgaagatgt ggttgttccg ggactgtttg      60
ccgttggtga atcgcttgt gtatcggtac acggcgctaa ccgtctgggc ggcaactcgc     120
tgctggacct ggtggtcttt ggtcgcgcgg caggtctgca tctgcaagag tctatcgccg     180
agcagggcgc actgcgcgat gccagcgagt ctgatgttga agcgtctctg gatcgcctga     240
accgctggaa caataatcgt aacggtgaag atccggtggc gatccgtaaa gcgctgcaag     300
aatgtatgca gcataacttc tcggtcttcc gtgaaggtga tgcgatggcg aaagggcttg     360
agcagttgaa agtgatccgc gagcgtctga aaaatgcccg tctggatgac acttccagcg     420
agttcaacac ccagcgcgtt gagtgcctgg aactggataa cctgatggaa acggcgtatg     480
caacggctgt ttctgccaac ttccgtaccg aaagccgtgg cgcgcatagc cgcttcgact     540
tcccggatcg tgatgatgaa actggctgt gccactccct gtatctgcca gagtcggaat     600
ccatgacgcg ccgaagcgtc aacatggaac cgaaactgcg cccggcattc ccgccgaaga     660
ttcgtactta ctaatgcgga gacaggaaaa tgagactcga gttttcaatt tatcgctata     720
acccggatgt tgatgatgct ccgcgtatgc aggattacac cctggaagcg atgaaggtc     780 gcgacatgat gctgctggat gcgcttatcc agctaaaaga gaaagatccc agcctgtcgt     840
tccgccgctc ctgccgtgaa ggtgtgtgcg gttccgacgg tctgaacatg aacggcaaga     900
atggtctggc ctgtattacc ccgatttcgg cactcaacca gccgggcaag aagattgtga     960
ttcgcccgct gccaggttta ccggtgatcc gcgatttggt ggtagacatg ggacaattct    1020
atgcgcaata tgagaaaatt aagccttacc tgttgaataa tggacaaaat ccgccagctc    1080
gcgagcattt acagatgcca gagcagcgcg aaaaactcga cgggctgtat gaatgtattc    1140
tctgcgcatg ttgttcaacc tcttgtccgt ctttctggtg aatcccgat aagtttatcg    1200 gcccggcagg cttgttagcg gcatatcgtt tcctgattga tagccgtgat accgagactg    1260
acagccgcct cgacggtttg agtgatgcat tcagcgtatt ccgctgtcac agcatcatga    1320
actgcgtcag tgtatgtccg aagggctga acccgacgcg cgccatcggc catatcaagt    1380
cgatgttgtt gcaacgtaat gcgtaaaccg taggcctgat aagacgcgca agcgtcgcat    1440
caggcaacca gtgccggatg cggcgtgaac gccttatccg gcctacaagt cattacccgt    1500
aggcctgata agcgcagcgc atcaggcgta acaagaaat gcaggaaatc tttaaaaact    1560 gccctgaca ctaagacagt ttttaaaggt tccttcgcga gccactacgt agacaagagc    1620
tcgcaagtga accccggcac gcacatcact gtgcgtggta gtatccacgg cgaagtaagc    1680
ataaaaaaga tgcttaaggg atcacgagtg taggctggag ctgcttcgaa gttcctatac    1740
tttctagaga ataggaactt cggaatagga acttcaagat ccccttatta gaagaactcg    1800
tcaagaaggc gatagaaggc gatgcgctgc gaatcgggag cggcgatacc gtaaagcacg    1860
```

-continued

```
aggaagcggt cagcccattc gccgccaagc tcttcagcaa tatcacgggt agccaacgct   1920
atgtcctgat agcggtccgc cacacccagc cggccacagt cgatgaatcc agaaaagcgg   1980
ccatttccca ccatgatatt cggcaagcag gcatcgccat gggtcacgac gagatcctcg   2040
ccgtcgggca tgcgcgcctt gagcctggcg aacagttcgg ctggcgcgag cccctgatgc   2100
tcttcgtcca gatcatcctg atcgacaaga ccggcttcca tccgagtacg tgctcgctcg   2160
atgcgatgtt tcgcttggtg gtcgaatggg caggtagccg gatcaagcgt atgcagccgc   2220
cgcattgcat cagccatgat ggatactttc tcggcaggag caaggtgaga tgacaggaga   2280
tcctgccccg gcacttcgcc caatagcagc cagtcccttc ccgcttcagt gacaacgtcg   2340
agcacagctg cgcaaggaac gcccgtcgtg gccagccacg atagccgcgc tgcctcgtcc   2400
tgcagttcat tcagggcacc ggacaggtcg gtcttgacaa aaagaaccgg gcgcccctgc   2460
gctgacagcc ggaacacggc ggcatcagag cagccgattg tctgttgtgc ccagtcatag   2520
ccgaatagcc tctccaccca gcggccgga gaacctgcgt gcaatccatc ttgttcaatc    2580
atgcgaaacg atcctcatcc tgtctcttga tcagatcttg atccctgcg ccatcagatc    2640
cttggcggca agaaagccat ccagtttact ttgcagggct tcccaacctt accagagggc   2700
gccccagctg gcaattccgg ttcgcttgct gtccataaaa ccgccagtc tagctatcgc    2760
catgtaagcc cactgcaagc tacctgcttt ctctttgcgc ttgcgttttc ccttgtccag   2820
atagcccagt agctgacatt catccggggt cagcaccgtt tctgcggact ggctttctac   2880
gtgttccgct tcctttagca gcccttgcgc cctgagtgct tgcggcagcg tgagcttcaa   2940
aagcgctctg aagttcctat actttctaga gaataggaac ttcgaactgc aggtcgacgg   3000
atccccggaa ttaattctca tgtttgacag aaaggataca caatgagtag cgtagatatt   3060
ctggtccctg acctgcctga atccgtagcc gatgccaccg tcgcaacctg gcataaaaaa   3120
cccggcgacg cagtcgtacg tgatgaagtg ctggtagaaa tcgaaactga caaagtggta   3180
ctggaagtac cggcatcagc agacggcatt ctggatgcgg ttctggaaga tgaaggtaca   3240
acggtaacgt ctcgtcagat ccttggtcgc ctgcgtgaag gcaacagcgc cggtaaagaa   3300
accagcgcca aatctgaaga gaaagcgtcc actccggcgc aacgccagca ggcgtctctg   3360
gaagagcaaa acaacgatgc gttaagcccg gcgatccgtc gcctgctggc tgaacacaat   3420
ctcgacgcca gcgccattaa aggcaccggt gtgggtggtc gtctgactcg tgaagatgtg   3480
gaaaaacatc tggcgaaagc cccggcgaaa gagtctgctc cggcagcggc tgctccggcg   3540
gcgcaaccgg ctctggctgc acgtagtgaa aaacgtgtcc cgatgactcg cctgcgtaag   3600
cgtgtggcag agcgtctgct ggaagcgaaa aactccaccg ccatgctgac cacgttcaac   3660
gaagtcaaca tgaagccgat tatggatctg cgtaagcagt acggtgaagc gtttgaaaaa   3720
cgccacggca tccgtctggg ctttatgtcc ttctacgtga agcggtggt tgaagccctg   3780
aaacgttacc cggaagtgaa cgcttctatc gacggcgatg acgtggttta ccacaactat   3840
ttcgacgtca gcatggcggt ttctacgccg cgcggcctgg tgacgccggt tctgcgtgat   3900
gtcgatacc tcggcatggc agacatcgag aagaaaatca agagctggca gtcaaaggc    3960
cgtgacggca agctgaccgt tgaagatctg accggtggta acttcaccat caccaacggt   4020
ggtgtgttcg gttccctgat gtctacgccg atcatcaacc cgccgcagag cgcaattctg   4080
ggtatgcacg ctatcaaaga tcgtccgatg gcggtgaatg gtcaggttga gatcctgccg   4140
atgatgtacc tggcgctgtc ctacgatcac cgtctgatcg atggtcgcga atccgtgggc   4200
ttcctggtaa cgatcaaaga gttgctggaa gatccgacgc gtctgctgct ggacgtgtag   4260
```

```
tagtttaagt ttcacctgca ctgtagaccg gataaggcat tatcgccttc tccggcaatt    4320
gaagcctgat gcgacgctga cgcgtcttat caggcctacg ggaccaccaa tgtaggtcgg    4380
ataaggcgca gcgccgcat ccgacaagcg atgcctgatg tgacgtttaa cgtgtcttat    4440
caggcctacg ggtgaccgac aatgcccgga agcgatacga aatattcggt ctacggttta    4500
aaagataacg attactgaag gatggacaga acacatgaac ttacatgaat atcaggcaaa    4560
acaactttt gcccgctatg gcttaccagc accgtgggt tatgcctgta ctactccgcg     4620
cgaagcagaa gaagccgctt caaaaatcgg tgccggtccg tgggtagtga aatgtcaggt    4680
tcacgctggt ggccgcggta aagcgggcgg tgtgaaagtt gtaaacagca aagaagacat    4740
ccgtgctttt gcagaaaact ggctgggcaa gcgtctggta acgtatcaaa cagatgccaa    4800
tggccaaccg gttaaccaga ttctggttga agcagcgacc gatatcgcta aagagctgta    4860
tctcggtgcc gttgttgacc gtagttcccg tcgtgtggtc tttatggcct ccaccgaagg    4920
cggcgtggaa atcgaaaaag tggcggaaga aactccgcac ctgatccata agttgcgct    4980
tgatccgctg actgggccga tgccgtatca gggacgcgag ctggcgttca aactgggtct    5040
ggaaggtaaa ctggttcagc agttcaccaa aatcttcatg ggcctggcga ccatttttcct   5100
ggagcgcgac ctggcgttga tcgaaatcaa cccgctggtc atcaccaaac agggcgatct    5160
gatttgcctc gacggcaaac tgggcgctga cggcaacgca ctgttccgcc agcctgatct    5220
gcgcgaaatg cgtgaccagt cgcaggaaga tccgcgtgaa gcacaggctg cacagtggga    5280
actgaactac gttgcgctgg acggtaacat cggttgtatg gttaacggcg caggtctggc    5340
gatgggtacg atggacatcg ttaaactgca cggcggcgaa ccggctaact tccttgacgt    5400
tggcggcggc gcaaccaaag aacgtgtaac cgaagcgttc aaaatcatcc tctctgacga    5460
caaagtgaaa gccgttctgg ttaacatctt cggcggtatc gttcgttgcg acctgatcgc    5520
tgacggtatc atcggcgcgg tagcagaagt gggtgttaac gtaccggtcg tggtacgtct    5580
ggaaggtaac aacgccgaac tcggcgcgaa gaaactggct gacagcggcc tgaatattat    5640
tgcagcaaaa ggtctgacgg atgcagctca gcaggttgtt gccgcagtgg agggaaata    5700
atgattccgg ggatccgtcg acctgcagtt cgaagttcct atctagaaag tataggaact    5760
tcgaagcagc tccagcctac actgaaaact gttctgaaat aaatatctgt aataagaaat    5820
agccctcgcc gcttccctct acaggaatgg cgaagggctg tcggtttcga catggttggc    5880
catcgtatga tggccttttt tgtgcttatc gcgatgattt tcgctgcgct atcagggtaa    5940
atttatagtc atcggtatta aaagcgttgc ggctatattc aaacacccga ccatcaacta    6000
aatatccacg cgatactttt tcaagaatcg gctttgtctg gctgatatta agcagacggc    6060
tcatctcttc ggttggcatc agaggaatga tttcctgttc gctacgatcg ataaccattt    6120
tcttcacttc ttcgataaag tgatatttcg aattttccat gacctgccag gtgagatccg    6180
ggaacaacgc aagcggcatc caggtttctt ccagcgccat tggcttttgc ttgcgatagc    6240
gcacgcgctt cacatgccac acacgatcct gcggggtgat ttgtagctgt tgctgaagaa    6300
aatcgtcagc cggaatcact tcgaatatca gaacttcact gtgtgtatcg acgtgacggt    6360
ccgacagttt ttcatcaaaa ctggttaact gaaaaatatc gtaattgacc cgctcttctt    6420
tgacgtaagt cccgctgccc tgaatgcttt cgaggatctg ctgctcgact agctggcgca    6480
aagcctgacg caccgtaacc cggctgacgc caaactctgt ttgtagcgct gattcagtgg    6540
gtaacgcatc gccaggttta agctcgccac gcgcaatttg ttcacgaatg cgatcggcaa    6600
tctgccggta aagggcttg tgtcccattt ttagtatctc attaatacga atttaaccat    6660
```

```
tatgcccgat aaattcatcc tgtaaataat acaaatacaa tacaaataat ttcaatcaag    6720
tgaaattgat cacataatgg tattgtttta tcg                                 6753

<210> SEQ ID NO 3
<211> LENGTH: 2742
<212> TYPE: DNA
<213> ORGANISM: Escherichia coli

<400> SEQUENCE: 3
ccggtcaggc actgactgtg aatgagaaag gcgaagatgt ggttgttccg ggactgtttg      60
ccgttggtga atcgcttgt gtatcggtac acggcgctaa ccgtctgggc ggcaactcgc     120
tgctggacct ggtggtcttt ggtcgcgcgg caggtctgca tctgcaagag tctatcgccg     180
agcagggcgc actgcgcgat gccagcgagt ctgatgttga agcgtctctg gatcgcctga     240
accgctggaa caataatcgt aacggtgaag atccggtggc gatccgtaaa gcgctgcaag     300
aatgtatgca gcataacttc tcggtcttcc gtgaaggtga tgcgatggcg aaagggcttg     360
agcagttgaa agtgatccgc gagcgtctga aaaatgcccg tctggatgac acttccagcg     420
agttcaacac ccagcgcgtt gagtgcctgg aactggataa cctgatggaa acggcgtatg     480
caacggctgt ttctgccaac ttccgtaccg aaagccgtgg cgcgcatagc cgcttcgact     540
tcccggatcg tgatgatgaa aactggctgt gccactccct gtatctgcca gagtcggaat     600
ccatgacgcg ccgaagcgtc aacatggaac cgaaactgcg cccggcattc ccgccgaaga     660
ttcgtactta ctaatgcgga gacaggaaaa tgagactcga gttttcaatt tatcgctata     720
acccggatgt tgatgatgct ccgcgtatgc aggattacac cctggaagcg gatgaaggtc     780
gcgacatgat gctgctggat gcgcttatcc agctaaaaga gaaagatccc agcctgtcgt     840
tccgccgctc ctgccgtgaa ggtgtgtgcg gttccgacgg tctgaacatg aacggcaaga     900
atggtctggc ctgtattacc ccgatttcgg cactcaacca gccgggcaag aagattgtga     960
ttcgcccgct gccaggttta ccggtgatcc gcgatttggt ggtagacatg ggacaattct    1020
atgcgcaata tgagaaaatt aagccttacc tgttgaataa tggacaaaat ccgccagctc    1080
gcgagcattt acagatgcca gagcagcgcg aaaaactcga cgggctgtat gaatgtattc    1140
tctgcgcatg ttgttcaacc tcttgtccgt cttttctggt gaatcccgat aagtttatcg    1200
gcccggcagg cttgttagcg gcatatcgtt cctgattga tagccgtgat accgagactg    1260
acagccgcct cgacggtttg agtgatgcat tcagcgtatt ccgctgtcac agcatcatga    1320
actgcgtcag tgtatgtccg aaggggctga acccgacgcg cgccatcggc catatcaagt    1380
cgatgttgtt gcaacgtaat gcgtaaaccg taggcctgat aagacgcgca agcgtcgcat    1440
caggcaacca gtgccggatg cggcgtgaac gccttatccg gcctacaagt cattacccgt    1500
aggcctgata agcgcagcgc atcaggcgta acaaagaaat gcaggaaatc tttaaaaact    1560 gccctgaca ctaagacagt ttttaaaggt tccttcgcga gccactacgt agacaagagc    1620
tcgcaagtga accccggcac gcacatcact gtgcgtggta gtatccacgg cgaagtaagc    1680 ataaaaaga tgattccggg gatccgtcga cctgcagttc gaagttccta tctagaaagt    1740
ataggaactt cgaagcagct ccagcctaca ctgaaaactg ttctgaaata aatatctgta    1800
ataagaaata gccctcgccg cttccctcta caggaatggc gaagggctgt cggtttcgac    1860
atggttggcc atcgtatgat ggcctttttt gtgcttatcg cgatgatttt cgctgcgcta    1920
tcagggtaaa tttatagtca tcggtattaa aagcgttgcg gctatattca aacacccgac    1980
catcaactaa atatccacgc gatacttttt caagaatcgg cttttgtctgg ctgatattaa    2040
```

```
gcagacggct catctcttcg gttggcatca gaggaatgat ttcctgttcg ctacgatcga   2100
taaccatttt cttcacttct tcgataaagt gatatttcga attttccatg acctgccagg   2160
tgagatccgg gaacaacgca agcggcatcc aggtttcttc cagcgccatt ggcttttgct   2220
tgcgatagcg cacgcgcttc acatgccaca cacgatcctg cggggtgatt tgtagctgtt   2280
gctgaagaaa atcgtcagcc ggaatcactt cgaatatcag aacttcactg tgtgtatcga   2340
cgtgacggtc cgacagtttt tcatcaaaac tggttaactg aaaaatatcg taattgaccc   2400
gctcttcttt gacgtaagtc ccgctgccct gaatgctttc gaggatctgc tgctcgacta   2460
gctggcgcaa agcctgacgc accgtaaccc ggctgacgcc aaactctgtt tgtagcgctg   2520
attcagtggg taacgcatcg ccaggtttaa gctcgccacg cgcaatttgt tcacgaatgc   2580
gatcggcaat ctgccggtat aagggcttgt gtcccatttt tagtatctca ttaatacgaa   2640
tttaaccatt atgcccgata aattcatcct gtaaataata caaatacaat acaaataatt   2700
tcaatcaagt gaaattgatc acataatggt attgttttat cg                      2742

<210> SEQ ID NO 4
<211> LENGTH: 6101
<212> TYPE: DNA
<213> ORGANISM: Escherichia coli

<400> SEQUENCE: 4
ccacccatct gggtttgccg gtatttaata ccgtgcgtga ggcggttgcc gcaaccggtg     60
ccacggcttc agttatctat gttcctgccc cattttgtaa agattcaatt ctggaagcta    120
ttgatgcggg catcaaattg attattacga ttaccgaagg tatccctacg ctggatatgt    180
tgacggttaa agtgaaactt gatgaagcgg gggtacgcat gattggtccg aattgtccgg    240
gcgttattac tccaggtgag tgcaaaattg gtattcagcc gggtcatatt cacaaacctg    300
ggaaagtcgg aattgtgtct cgttctggca ctctgacgta tgaggcagtt aaacagacca    360
cagattatgc ctttgggcag agtacctgtg tcggcatcgg aggcgatcct attccgggga    420
gtaattttat cgatattctg gaaatgtttg agaaagatcc gcagaccgag gcaatcgtca    480
tgattggcga gattggcggt tccgcggaag aagaagctgc agcctatatc aaagaacatg    540
tcacaaaacc ggtagtgggc tatatcgcgg gagtcacggc cccaaaaggt aaacgtatgg    600
gccatgccgg agcgatcatc gcgggcggca aggcactgc agatgaaaaa tttgcagccc     660
ttgaggccgc tggcgtaaaa acggtccgtt cccttgctga tattggtgaa gcactgaaaa    720
ccgtgttgaa ataaaggtcc aggcatcaaa taaaacgaaa ggctcagtcg aaagactggg    780
cctttcgttt tatctgttgt ttgtcggtga acgctctcta ctagagtcac actggctcac    840
cttcgggtgg gcctttctgc gtttatatgc catgtcttct actagtagcg gccgctgcag    900
tccggcaaaa aagggcaagg tgtcaccacc ctgcccttt tctttaaaac cgaaaagatt     960
acttcgcgtt atgcaggctt cctcgctcac tgactcgctg cgctcggtcg ttcggctgcg   1020
gcgagcggta tcagctcact caaaggcggt aatacggtta tccacagaat cagggggataa   1080 cgcaggaaag aacatgtgag caaaaggcca gcaaaggcca ggaaccgta aaaggccgc     1140 gttgctggcg ttttccaca ggctccgccc cctgacgag catcacaaaa atcgacgctc      1200
aagtcagagg tggcgaaacc cgacaggact ataaagatac caggcgtttc ccctggaag    1260 ctccctcgtg cgctctcctg ttccgaccct gccgcttacc ggataccgt ccgcctttct    1320 cccttcggga agcgtggcgc tttctcatag ctcacgctgt aggtatctca gttcggtgta   1380
ggtcgttcgc tccaagctgg gctgtgtgca cgaaccccc gttcagcccg accgctgcgc    1440
```

```
cttatccggt aactatcgtc ttgagtccaa cccggtaaga cacgacttat cgccactggc   1500
agcagccact ggtaacagga ttagcagagc gaggtatgta ggcggtgcta cagagttctt   1560
gaagtggtgg cctaactacg gctacactag aagaacagta tttggtatct gcgctctgct   1620
gaagccagtt accttcggaa aaagagttgg tagctcttga tccggcaaac aaaccaccgc   1680
tggtagcggt ggtttttttg tttgcaagca gcagattacg cgcagaaaaa aaggatctca   1740
agaagatcct ttgatctttt ctacggggtc tgacgctcag tggaacgaaa actcacgtta   1800
agggattttg gtcatgagat tatcaaaaag gatcttcacc tagatccttt taaattaaaa   1860
atgaagtttt aaatcaatct aaagtatata tgagtaaact tggtctgaca gctcgagtcc   1920
cgtcaagtca gcgtaatgct ctgccagtgt tacaaccaat taaccaattc tgattagaaa   1980
aactcatcga gcatcaaatg aaactgcaat ttattcatat caggattatc aataccatat   2040
ttttgaaaaa gccgtttctg taatgaagga gaaaactcac cgaggcagtt ccataggatg   2100
gcaagatcct ggtatcggtc tgcgattccg actcgtccaa catcaataca acctattaat   2160
ttcccctcgt caaaaataag gttatcaagt gagaaatcac catgagtgac gactgaatcc   2220
ggtgagaatg gcaaaagctt atgcatttct ttccagactt gttcaacagg ccagccatta   2280
cgctcgtcat caaaatcact cgcatcaacc aaaccgttat tcattcgtga ttgcgcctga   2340
gcgagacgaa atacgcgatc gctgttaaaa ggacaattac aaacaggaat cgaatgcaac   2400
cggcgcagga acactgccag cgcatcaaca atattttcac ctgaatcagg atattcttct   2460
aatacctgga atgctgtttt cccggggatc gcagtggtga gtaaccatgc atcatcagga   2520
gtacggataa aatgcttgat ggtcggaaga ggcataaatt ccgtcagcca gtttagtctg   2580
accatctcat ctgtaacatc attggcaacg ctacctttgc catgtttcag aaacaactct   2640
ggcgcatcgg gcttcccata caatcgatag attgtcgcac ctgattgccc gacattatcg   2700
cgagcccatt tatacccata taaatcagca tccatgttgg aatttaatcg cggcctggag   2760
caagacgttt cccgttgaat atggctcata acacccttg tattactgtt tatgtaagca   2820
gacagtttta ttgttcatga tgatatattt ttatcttgtg caatgtaaca tcagagattt   2880
tgagacacaa cgtggctttg ttgaataaat cgaacttttg ctgagttgaa ggatcagctc   2940
gagtgccacc tgacgtctaa gaaaccatta ttatcatgac attaacctat aaaaataggc   3000
gtatcacgag gcagaatttc agataaaaaa aatccttagc tttcgctaag gatgatttct   3060
ggaattcgcg gccgcttcta gagactagtg gaagacatcg ctttgacagc tagctcagtc   3120
ctaggtactg tgctagctac tttaaactcc ccgagcaata gtaatgcaga actcagcatt   3180
gaaagcatgg cttgatagct cctatttatc aggtgctaac cagagctgga ttgaacagct   3240
gtatgaagat tttctgacag atccggattc agtggatgcg aattggcgca gcactttca   3300 gcagttgcct ggcaccggtg taaaaccgga tcagtttcat tcccagacgc gggagtattt   3360
tcgtcgtctg gcgaaagatg cgagccggta ttcaagtaca atttctgatc cggatacgaa   3420
tgtaaaacag gtgaaagtgc ttcagttaat taatgcgtat cgctttagag gccatcagca   3480
tgcgaatctg gatccgctgg gcttatggca gcaggataaa gtcgcggatc tggatccaag   3540
ttttcacgat ttaacggaag ctgatttca ggaaaccttt aacgtcggct cattcgcaag   3600
tgggaaagaa acaatgaaac tgggcgaact tcttgaggcg ctgaaacaga cttattgtgg   3660
ccctattggt gcggaatata tgcatattac ctcaactgaa gagaaacgtt ggattcagca   3720
gagaatcgag agtggccgcg cgacttttaa ctccgaagaa aaaaaagat tcctgtcaga   3780 actgacagcc gcggaaggct tagagcggta tttgggtgcc aaattcccag agcaaaacg   3840
```

```
gttcagcctg gagggcggtg atgcgctgat cccgatgctg aaagaaatga ttcggcatgc    3900
gggaaatagc ggaactcggg aagtggtgtt aggaatggca caccgcggcc gtttgaatgt    3960
actggttaac gtattaggaa aaaaacctca ggatttattt gatgagttcg cgggaaaaca    4020
taaagaacat ctgggcactg gtgatgtcaa atatcacatg ggcttctcaa gtgattttca    4080
gacggatgga ggtctggttc acctggcact ggcatttaat ccttctcatc tggaaatcgt    4140
aagtccggtc gttattggtt ccgtgcgcgc tcgcttagat cggttagatg aacctagctc    4200
aaacaaagtt ttaccaatca cgatccatgg ggatgcagct gttaccggac agggtgttgt    4260
gcaggagact ttgaatatgt ccaaagcgcg cgggtatgag gtgggtggta cggtgcgtat    4320
tgttatcaat aatcaggtgg gttttacaac cagtaaccct ctggatgctc gctctacgcc    4380
gtattgcact gatattggta aaatggtgca ggcaccaatt tttcacgtca atgccgatga    4440
tccggaagct gttgcctttg ttacgcgcct ggctctggat tttcgtaaca ctttcaaacg    4500
tgatgtattt atcgatttag tatgctatcg tcgtcatggt cataatgagg ctgatgaacc    4560
tagcgctacc cagccactga tgtatcagaa aattaaaaaa catcctaccc ctcgtaaaat    4620
ttatgcggat aaactggagc aggaaaaagt ggctactctt gaagatgcta ctgaaatggt    4680
caatctttat cgggatgcat tggatgcggg tgattgcgtg gtcgcggaat ggcgcccgat    4740
gaatatgcat tcatttactt ggtcaccgta tttaaatcat gagtgggatg aggaatatcc    4800
gaataaagtg gagatgaaac gcctgcagga attagcaaaa cgtattagca cagtacctga    4860
agcggttgag atgcagtcta gagttgccaa aatctatgga gatcgccagg ccatggcagc    4920
aggggaaaaa ctttttgatt gggggggagc cgaaaacctg gcatatgcga cgctggtaga    4980
tgagggcatt ccggtgcgcc tttctggtga agattctggg cgcggtactt ttttttcatcg    5040 gcacgctgtt attcataacc agtctaacgg tagtacttat actccgctgc agcacatcca    5100
caatggtcag ggtgcgttcc gtgtatggga ttccgtgctg agtgaagaag cggttcttgc    5160
gtttgagtat gggtatgcaa ctgccgagcc acgcacgctg acgatctggg aagcccagtt    5220
tggcgatttt gcaaatggtg cccaggtggt aatcgatcag tttattagct ccggcgaaca    5280
gaaatggggg cggatgtgtg gtttagttat gttgttaccg catggctatg aaggtcaggg    5340
acctgagcac agctcagcgc gcctggaacg ctatcttcag ctgtgtgcgg aacagaacat    5400
gcaggtatgc gttccttcca cgccggctca ggtttatcat atgttaagac gtcaggcctt    5460
gcgcggtatg cggcgcccgt tggtcgtgat gtccccgaaa agtttactgc gccatccgtt    5520
agcagttagc agcctggagg aactggcaaa cggtacgttc ttgccagcta tcggcgaaat    5580
cgatgaactg gatcctaaag gggtgaaacg cgttgttatg tgttctggta aagtgtatta    5640
tgatcttttg gaacagcgtc gcaaaaataa tcagcacgat gtagctattg tgcggatcga    5700
gcagctgtat ccgttcccgc acaaagcaat gcaggaagtg ctgcagcagt cgcacatgt    5760 caaagatttt gtctggtgtc aggaggaacc gcttaatcag ggggcctggt attgtagtca    5820
gcaccatttc cggaggtga tcccgtttgg ggcgtcctta cggtatgctg gtcgccctgc    5880
ctccgcaagt ccggccgtgg gatatatgag cgttcaccag aaacagcagc aggatttggt    5940
gaatgatgct ttgaatgtgg aatgaatgtc catcctgatc gacaaaaaca ctaaagtaat    6000
ttgtcagggc tttaccggtt cccagggcac atttcactca gagcaggcca tcgcttatgg    6060
gaccaaaatg gtgggtggtg taacgcctgg taaaggaggc a                       6101
```

```
<210> SEQ ID NO 5
<211> LENGTH: 9013
<212> TYPE: DNA
<213> ORGANISM: Escherichia coli

<400> SEQUENCE: 5
```

| | | | | | |
|---|---|---|---|---|---|
| ccggcgaaag | agtctgctcc | ggcagcggct | gctccggcgg | cgcaaccggc | tctggctgca | 60 |
| cgtagtgaaa | aacgtgtccc | gatgactcgc | ctgcgtaagc | gtgtggcaga | gcgtctgctg | 120 |
| gaagcgaaaa | actccaccgc | catgctgacc | acgttcaacg | aagtcaacat | gaagccgatt | 180 |
| atggatctgc | gtaagcagta | cggtgaagcg | tttgaaaaac | gccacggcat | ccgtctgggc | 240 |
| tttatgtcct | tctacgtgaa | agcggtggtt | gaagccctga | acgttaccc | ggaagtgaac | 300 |
| gcttctatcg | acggcgatga | cgtggtttac | cacaactatt | tcgacgtcag | catggcggtt | 360 |
| tctacgccgc | gcggcctggt | gacgccggtt | ctgcgtgatg | tcgatacccct | cggcatggca | 420 |
| gacatcgaga | agaaaatcaa | agagctggca | gtcaaaggcc | gtgacggcaa | gctgaccgtt | 480 |
| gaagatctga | ccggtggtaa | cttcaccatc | accaacggtg | gtgtgttcgg | ttccctgatg | 540 |
| tctacgccga | tcatcaaccc | gccgcagagc | gcaattctgg | gtatgcacgc | tatcaaagat | 600 |
| cgtccgatgg | cggtgaatgg | tcaggttgag | atcctgccga | tgatgtacct | ggcgctgtcc | 660 |
| tacgatcacc | gtctgatcga | tggtcgcgaa | tccgtgggct | tcctggtaac | gatcaaagag | 720 |
| ttgctggaag | atccgacgcg | tctgctgctg | gacgtagt | agtttaagtt | tcacctgcac | 780 |
| tgtagaccgg | ataaggcatt | atcgccttct | ccggcaattg | aagcctgatg | cgacgctgac | 840 |
| gcgtcttatc | aggcctacgg | gaccaccaat | gtaggtcgga | taaggcgcaa | gcgccgcatc | 900 |
| cgacaagcga | tgcctgatgt | gacgtttaac | gtgtcttatc | aggcctacgg | gtgaccgaca | 960 |
| atgcccggaa | gcgatacgaa | atattcggtc | tacggtttaa | aagataacga | ttactgaagg | 1020 |
| atggacagaa | cacatgaact | tacatgaata | tcaggcaaaa | caacttttg | cccgctatgg | 1080 |
| cttaccagca | ccgtgggtt | atgcctgtac | tactccgcgc | gaagcagaag | aagccgcttc | 1140 |
| aaaaatcggt | gccggtccgt | gggtagtgaa | atgtcaggtt | cacgctggtg | gccgcggtaa | 1200 |
| agcgggcggt | gtgaaagttg | taaacagcaa | agaggacatc | cgtgcttttg | cagaaaactg | 1260 |
| gctgggcaag | cgtctggtaa | cgtatcaaac | agatgccaat | ggccaaccgg | ttaaccagat | 1320 |
| tctggttgaa | gcagcgaccg | atatcgctaa | agagctgtat | ctcggtgccg | ttgttgaccg | 1380 |
| tagttcccgt | cgtgtggtct | ttatggcctc | caccgaaggc | ggcgtggaaa | tcgaaaaagt | 1440 |
| ggcggaagaa | actccgcacc | tgatccataa | agttgcgctt | gatccgctga | ctggcccgat | 1500 |
| gccgtatcag | ggacgcgagc | tggcgttcaa | actgggtctg | gaaggtaaac | tggttcagca | 1560 |
| gttcaccaaa | atcttcatgg | gcctggcgac | cattttcctg | gagcgcgacc | tggcgttgat | 1620 |
| cgaaatcaac | ccgctggtca | tcaccaaaca | gggcgatctg | atttgcctcg | acggcaaact | 1680 |
| gggcgctgac | ggcaacgcac | tgttccgcca | gcctgatctg | cgcgaaatgc | gtgaccagtc | 1740 |
| gcaggaagat | ccgcgtgaag | cacaggctgc | acagtgggaa | ctgaactacg | ttgcgctgga | 1800 |
| cggtaacatc | ggttgtatgg | ttaacggcgc | aggtctggcg | atgggtacga | tggacatcgt | 1860 |
| taaactgcac | ggcggcgaac | cggctaactt | ccttgacgtt | ggcggcggcg | caaccaaaga | 1920 |
| acgtgtaacc | gaagcgttca | aaatcatcct | ctctgacgac | aaagtgaaag | ccgttctggt | 1980 |
| taacatcttc | ggcggtatcg | ttcgttgcga | cctgatcgct | gacggtatca | tcggcgcggt | 2040 |
| agcagaagtg | ggtgttaacg | taccggtcgt | ggtacgtctg | gaaggtaaca | acgccgaact | 2100 |
| cggcgcgaag | aaactggctg | acagcggcct | gaatattatt | gcagcaaaag | gtctgacgga | 2160 |

```
tgcagctcag caggttgttg ccgcagtgga ggggaaataa tgtccatttt aatcgataaa    2220
aacaccaagg ttatctgcca gggctttacc ggtagccagg ggactttcca ctcagaacag    2280
gccattgcat acggcactaa aatggttggc ggcgtaaccc caggtaaagg cggcaccacc    2340
cacctcggcc tgccggtgtt caacaccgtg cgtgaagccg ttgctgccac tggcgctacc    2400
gcttctgtta tctacgtacc agcaccgttc tgcaaagact ccattctgga agccatcgac    2460
gcaggcatca aactgattat caccatcact gaaggcatcc cgacgctgga tatgctgacc    2520
gtgaaagtga agctggatga agcaggcgtt cgtatgatcg cccgaactg cccaggcgtt     2580 atcactccgg gtgaatgcaa aatcggtatc cagcctggtc acattcacaa accgggtaaa    2640
gtgggtatcg tttcccgttc cggtacactg acctatgaag cggttaaaca gaccacggat    2700
tacggtttcg tcagtcgac ctgtgtcggt atcggcggtg acccgatccc gggctctaac     2760
tttatcgaca ttctcgaaat gttcgaaaaa gatccgcaga ccgaagcgat cgtgatgatc    2820
ggtgagatcg gcggtagcgc tgaagaagaa gcagctgcgt acatcaaaga gcacgttacc    2880
aagccagttg tgggttacat cgctggtgtg actgcgccga aaggcaaacg tatgggccac    2940
gcgggtgcca tcattgccgg tgggaaaggg actgcggatg agaaattcgc tgctctggaa    3000
gccgcaggcg tgaaaaccgt tcgcagcctg cggatatcg gtgaagcact gaaaactgtt     3060
ctgaaataaa ggtccaggca tcaaataaaa cgaaaggctc agtcgaaaga ctgggccttt    3120
cgttttatct gttgtttgtc ggtgaacgct ctctactaga gtcacactgg ctcaccttcg    3180
ggtgggcctt tctgcgttta tatgccatgt cttctactag tagcggccgc tgcagtccgg    3240
caaaaaaggg caaggtgtca ccaccctgcc ctttttcttt aaaaccgaaa agattacttc    3300
gcgttatgca ggcttcctcg ctcactgact cgctgcgctc ggtcgttcgg ctgcggcgag    3360
cggtatcagc tcactcaaag gcggtaatac ggttatccac agaatcaggg gataacgcag    3420
gaaagaacat gtgagcaaaa ggccagcaaa aggccaggaa ccgtaaaaag gccgcgttgc    3480
tggcgttttt ccacaggctc cgcccccctg acgagcatca aaaaatcga cgctcaagtc     3540 agaggtggcg aaacccgaca ggactataaa gataccaggc gtttccccct ggaagctccc    3600
tcgtgcgctc tcctgttccg accctgccgc ttaccggata cctgtccgcc tttctccctt    3660
cgggaagcgt ggcgctttct catagctcac gctgtaggta tctcagttcg gtgtaggtcg    3720
ttcgctccaa gctgggctgt gtgcacgaac cccccgttca gcccgaccgc tgcgccttat    3780
ccggtaacta tcgtcttgag tccaacccgg taagacacga cttatcgcca ctggcagcag    3840
ccactggtaa caggattagc agagcgaggt atgtaggcgg tgctacagag ttcttgaagt    3900
ggtggcctaa ctacggctac actagaagaa cagtatttgg tatctgcgct ctgctgaagc    3960
cagttacctt cggaaaaaga gttggtagct cttgatccgg caaacaaacc accgctggta    4020
gcggtggttt ttttgtttgc aagcagcaga ttacgcgcag aaaaaaagga tctcaagaag    4080
atcctttgat cttttctacg gggtctgacg ctcagtggaa cgaaaactca cgttaaggga    4140
ttttggtcat gagattatca aaaaggatct tcacctagat ccttttaaat taaaaatgaa    4200
gttttaaatc aatctaaagt atatatgagt aaacttggtc tgacagctcg agtcccgtca    4260
agtcagcgta atgctctgcc agtgttacaa ccaattaacc aattctgatt agaaaaactc    4320
atcgagcatc aaatgaaact gcaatttatt catatcagga ttatcaatac catatttttg    4380
aaaaagccgt ttctgtaatg aaggagaaaa ctcaccgagg cagttccata ggatggcaag    4440
atcctggtat cggtctgcga ttccgactcg tccaacatca atacaaccta ttaatttccc    4500
ctcgtcaaaa ataaggttat caagtgagaa atcaccatga gtgacgactg aatccggtga    4560
```

```
gaatggcaaa agcttatgca tttctttcca gacttgttca acaggccagc cattacgctc    4620
gtcatcaaaa tcactcgcat caaccaaacc gttattcatt cgtgattgcg cctgagcgag    4680
acgaaatacg cgatcgctgt taaaaggaca attacaaaca ggaatcgaat gcaaccggcg    4740
caggaacact gccagcgcat caacaatatt ttcacctgaa tcaggatatt cttctaatac    4800
ctggaatgct gttttccgg  ggatcgcagt ggtgagtaac catgcatcat caggagtacg    4860
gataaaatgc ttgatggtcg gaagaggcat aaattccgtc agccagttta gtctgaccat    4920
ctcatctgta acatcattgg caacgctacc tttgccatgt ttcagaaaca actctggcgc    4980
atcgggcttc ccatacaatc gatagattgt cgcacctgat tgcccgacat tatcgcgagc    5040
ccatttatac ccatataaat cagcatccat gttggaattt aatcgcggcc tggagcaaga    5100
cgtttcccgt tgaatatggc tcataacacc ccttgtatta ctgtttatgt aagcagacag    5160
ttttattgtt catgatgata tatttttatc ttgtgcaatg taacatcaga gattttgaga    5220
cacaacgtgg ctttgttgaa taaatcgaac ttttgctgag ttgaaggatc agctcgagtg    5280
ccacctgacg tctaagaaac cattattatc atgcattaa  cctataaaaa taggcgtatc    5340
acgaggcaga atttcagata aaaaaaatcc ttagctttcg ctaaggatga tttctggaat    5400
tcgcggccgc ttctagagac tagtggaaga catcgctacc gtaggcctga taagacgcgc    5460
aagcgtcgca tcaggcaacc agtgccggat gcggcgtgaa cgccttatcc ggcctacaag    5520
tcattacccg taggcctgat aagcgcagcg catcaggcgt aacaagaaa  tgcaggaaat    5580
ctttaaaaac tgcccctgac actaagacag ttttaaagg  ttccttcgcg agccactacg    5640
tagacaagag ctcgcaagtg aacccccggca cgcacatcac tgtgcgtggt agtatccacg    5700
gcgaagtaag cataaaaag  atgcttaagg gatcacgaat gcagaacagc gctttgaaag    5760
cctggttgga ctcttcttac ctctctggcg caaaccagag ctggatagaa cagctctatg    5820
aagatttctt aaccgatcct gactcggttg acgctaactg gcgttcgacg ttccagcagt    5880
tacctggtac gggagtcaaa ccggatcaat tccactctca aacgcgtgaa tatttccgcc    5940
gcctggcgaa agacgcttca cgttactctt caacgatctc cgaccctgac accaatgtga    6000
agcaggttaa agtcctgcag ctcattaacg cataccgctt ccgtggtcac cagcatgcga    6060
atctcgatcc gctgggactg tggcagcaag ataaagtggc cgatctggat ccgtctttcc    6120
acgatctgac cgaagcagac ttccaggaga cttttcaacgt cggttcattt gccagcggca    6180
aagaaaccat gaaactcggc gagctgctgg aagccctcaa gcaaacctac tgcggcccga    6240
ttggtgccga gtatatgcac attaccagca ccgaagaaaa acgctggatc caacagcgta    6300
tcgagtctgg tcgcgcgact ttcaatagcg aagagaaaaa acgcttctta agcgaactga    6360
ccgccgctga aggtcttgaa cgttacctcg gcgcaaaatt ccctggcgca aaacgcttct    6420
cgctggaagg cggtgacgcg ttaatcccga tgcttaagag atgatccgc  cacgctggca    6480
acagcggcac ccgcgaagtg gttctcggga tggcgcaccg tggtcgtctg aacgtgctgg    6540
tgaacgtgct gggtaaaaaa ccgcaagact tgttcgacga gttcgccggt aaacataaag    6600
aacacctcgg cacgggtgac gtgaaatacc acatgggctt ctcgtctgac ttccagaccg    6660
atggcggcct ggtgcacctg gcgctggcgt ttaacccgtc tcaccttgag attgtaagcc    6720
cggtagttat cggttctgtt cgtgcccgtc tggacagact tgatgagccg agcagcaaca    6780
aagtgctgcc aatcaccatc cacggtgacg ccgcagtgac cggcagggc  gtggttcagg    6840
aaaccctgaa catgtcgaaa gcgcgtggtt atgaagttgg cggtacggta cgtatcgtta    6900
tcaacaacca ggttggtttc accacctcta atccgctgga tgcccgttct acgccgtact    6960
```

```
gtactgatat cggtaagatg gttcaggccc cgattttcca cgttaacgcg gacgatccgg    7020
aagccgttgc ctttgtgacc cgtctggcgc tcgatttccg taacacccttt aaacgtgatg   7080 ttttcatcga cctggtgtgc taccgccgtc acggccacaa cgaagccgac gagccgagcg    7140
caacccagcc gctgatgtat cagaaaatca aaaacatcc gacaccgcgc aaaatctacg     7200
ctgacaagct ggagcaggaa aaagtggcga cgctggaaga tgccaccgag atggttaacc    7260
tgtaccgcga tgcgctggat gctggcgatt gcgtagtggc agagtggcgt ccgatgaaca    7320
tgcactcttt cacctggtcg ccgtacctca accacgaatg ggacgaagag taccccgaaca   7380 aagttgagat gaagcgcctg caggagctgg cgaaacgcat cagcacggtg ccggaagcag    7440
ttgaaatgca gtctcgcgtt gccaagattt atggcgatcg ccaggcgatg gctgccggtg    7500
agaaactgtt cgactggggc ggtgcggaaa acctcgctta cgccacgctg gttgatgaag    7560
gcattccggt tcgcctgtcg ggtgaggact ccggtcgcgg taccttcttc caccgccacg    7620
cggtgatcca caaccagtct aacggttcca cttacacgcc gctgcaacat atccataacg    7680
ggcagggcgc gttccgtgtc tgggactccg tactgtctga agaagcagtg ctggcgtttg    7740
aatatggtta tgccaccgca gaaccacgca ctctgaccat ctgggaagcg cagttcggtg    7800
acttcgccaa cggtgcgcag gtggttatcg accagttcat ctcctctggc gaacagaaat    7860
ggggccggat gtgtggtctg gtgatgttgc tgccgcacgg ttacgaaggg caggggccgg    7920
agcactcctc cgcgcgtctg gaacgttatc tgcaactttg tgctgagcaa acatgcagg    7980 tttgcgtacc gtctaccccg gcacaggttt accacatgct gcgtcgtcag gcgctgcgcg    8040
ggatgcgtcg tccgctggtc gtgatgtcgc cgaaatccct gctgcgtcat ccgctggcgg    8100
tttccagcct cgaagaactg gcgaacggca ccttcctgcc agccatcggt gaaatcgacg    8160
agcttgatcc gaagggcgtg aagcgcgtag tgatgtgttc tggtaaggtt tattacgacc    8220
tgctggaaca gcgtcgtaag aacaatcaac acgatgtcgc cattgtgcgt atcgagcaac    8280
tctacccgtt cccgcataaa gcgatgcagg aagtgttgca gcagtttgct cacgtcaagg    8340 atttttgtctg gtgccaggaa gagccgctca accagggcgc atggtactgc agccagcatc    8400
atttccgtga agtgattccg tttggggctt ctctgcgtta tgcaggccgc ccggcctccg    8460
cctctccggc ggtagggtat atgtccgttc accagaaaca gcaacaagat ctggttaatg    8520
acgcgctgaa cgtcgaataa ataaaggata cacaatgagt agcgtagata ttctggtccc    8580
tgacctgcct gaatccgtag ccgatgccac cgtcgcaacc tggcataaaa aacccggcga    8640
cgcagtcgta cgtgatgaag tgctggtaga aatcgaaact gacaaagtgg tactggaagt    8700
accggcatca gcagacggca ttctggatgc ggttctggaa gatgaaggta caacggtaac    8760
gtctcgtcag atccttggtc gcctgcgtga aggcaacagc gccggtaaag aaaccagcgc    8820
caaatctgaa gagaaagcgt ccactccggc gcaacgccag caggcgtctc tggaagagca    8880
aaacaacgat gcgttaagcc cggcgatccg tcgcctgctg gctgaacaca atctcgacgc    8940
cagcgccatt aaaggcaccg gtgtgggtgg tcgtctgact cgtgaagatg tggaaaaaca    9000
tctggcgaaa gcc                                                       9013
```

<210> SEQ ID NO 6
<211> LENGTH: 6608
<212> TYPE: DNA
<213> ORGANISM: Escherichia coli

<400> SEQUENCE: 6

```
cgcgttgctg gcgttttcc acaggctccg ccccctgac gagcatcaca aaaatcgacg        60
ctcaagtcag aggtggcgaa acccgacagg actataaaga taccaggcgt ttcccctgg      120
aagctccctc gtgcgctctc ctgttccgac cctgccgctt accggatacc tgtccgcctt    180
tctcccttcg ggaagcgtgg cgctttctca tagctcacgc tgtaggtatc tcagttcggt    240
gtaggtcgtt cgctccaagc tgggctgtgt gcacgaaccc cccgttcagc ccgaccgctg    300
cgccttatcc ggtaactatc gtcttgagtc caacccggta agacacgact tatcgccact    360
ggcagcagcc actggtaaca ggattagcag agcgaggtat gtaggcggtg ctacagagtt    420
cttgaagtgg tggcctaact acggctacac tagaagaaca gtatttggta tctgcgctct    480
gctgaagcca gttaccttcg gaaaaagagt tggtagctct tgatccggca aacaaaccac    540
cgctggtagc ggtggttttt tgtttgcaa gcagcagatt acgcgcagaa aaaaggatc     600
tcaagaagat cctttgatct tttctacggg gtctgacgct cagtggaacg aaaactcacg    660
ttaagggatt ttggtcatga gattatcaaa aaggatcttc acctagatcc ttttaaatta    720
aaaatgaagt tttaaatcaa tctaaagtat atatgagtaa acttggtctg acagctcgag    780
tttacggcta gctcagtcct aggtatagtg ctagctactt gttagaaaag agaagcacgt    840
aatgcagaac tcagcattga aagcatggct tgatagctcc tatttatcag gtgctaacca    900
gagctgatt gaacagctgt atgaagattt tctgacagat ccggattcag tggatgcgaa     960
ttggcgcagc acttttcagc agttgcctgg caccggtgta aaaccggatc agtttcattc   1020
ccagacgcgg gagtattttc gtcgtctggc gaaagatgcg agccggtatt caagtacaat   1080
ttctgatccg gatacgaatg taaaacaggt gaaagtgctt cagttaatta atgcgtatcg   1140
ctttagaggc catcagcatg cgaatctgga tccgctgggc ttatggcagc aggataaagt   1200
cgcggatctg gatccaagtt ttcacgattt aacggaagct gattttcagg aaaccttta    1260
cgtcggctca ttcgcaagtg ggaaagaaac aatgaaactg gcgaacttc ttgaggcgct    1320
gaaacagact tattgtggcc ctattggtgc ggaatatatg catattacct caactgaaga   1380
gaaacgttgg attcagcaga gaatcgagag tggccgcgcg acttttaact ccgaagaaaa   1440
aaaaagattc ctgtcagaac tgacagccgc ggaaggctta gagcggtatt tgggtgccaa   1500
attcccagga gcaaaacggt tcagcctgga gggcggtgat gcgctgatcc cgatgctgaa   1560
agaaatgatt cggcatgcgg gaaatagcgg aactcgggaa gtggtgttag aatggcaca    1620
ccgcggccgt ttgaatgtac tggttaacgt attaggaaaa aaacctcagg atttatttga   1680
tgagttcgcg ggaaaacata agaacatct gggcactggt gatgtcaaat atcacatggg    1740
cttctcaagt gattttcaga cggatggagg tctggttcac ctggcactgg catttaatcc   1800
ttctcatctg gaaatcgtaa gtccggtcgt tattggttcc gtgcgcgctc gcttagatcg   1860
gttagatgaa cctagctcaa acaaagtttt accaatcacg atccatgggg atgcagctgt   1920
taccggacag ggtgttgtgc aggagacttt gaatatgtcc aaagcgcgcg ggtatgaggt   1980
gggtggtacg gtgcgtattg ttatcaataa tcaggtgggt tttacaacca gtaaccctct   2040
ggatgctcgc tctacgccgt attgcactga tattggtaaa atggtgcagg caccaatttt   2100
tcacgtcaat gccgatgatc cggaagctgt tgcctttgtt acgcgcctgg ctctggattt   2160
tcgtaacact ttcaaacgtg atgtatttat cgatttagta tgctatcgtc gtcatggtca   2220
taatgaggct gatgaaccta gcgctaccca gccactgatg tatcagaaaa ttaaaaaaca   2280
tcctaccccct cgtaaaattt atgcggataa actggagcag gaaaaagtgg ctactcttga   2340
```

```
agatgctact gaaatggtca atctttatcg ggatgcattg gatgcgggtg attgcgtggt    2400
cgcggaatgg cgcccgatga atatgcattc atttacttgg tcaccgtatt taaatcatga    2460
gtgggatgag gaatatccga ataaagtgga gatgaaacgc ctgcaggaat tagcaaaacg    2520
tattagcaca gtacctgaag cggttgagat gcagtctaga gttgccaaaa tctatggaga    2580
tcgccaggcc atggcagcag gggaaaaact ttttgattgg gggggagccg aaaacctggc    2640
atatgcgacg ctggtagatg agggcattcc ggtgcgcctt tctggtgaag attctgggcg    2700
cggtactttt tttcatcggc acgctgttat tcataaccag tctaacggta gtacttatac    2760
tccgctgcag cacatccaca atggtcaggg tgcgttccgt gtatgggatt ccgtgctgag    2820
tgaagaagcg gttcttgcgt ttgagtatgg gtatgcaact gccgagccac gcacgctgac    2880
gatctgggaa gcccagtttg gcgattttgc aaatggtgcc caggtggtaa tcgatcagtt    2940
tattagctcc ggcgaacaga atgggggcg atgtgtggt ttagttatgt tgttaccgca    3000
tggctatgaa ggtcagggac ctgagcacag ctcagcgcgc ctggaacgct atcttcagct    3060
gtgtgcggaa cagaacatgc aggtatgcgt tccttccacg ccggctcagg tttatcatat    3120
gttaagacgt caggccttgc gggtatgcg gcgcccgttg gtcgtgatgt ccccgaaaag    3180
tttactgcgc catccgttag cagttagcag cctggaggaa ctggcaaacg gtacgttctt    3240
gccagctatc ggcgaaatcg atgaactgga tcctaaaggg gtgaaacgcg ttgttatgtg    3300
ttctggtaaa gtgtattatg atcttttgga acagcgtcgc aaaaataatc agcacgatgt    3360
agctattgtg cggatcgagc agctgtatcc gttcccgcac aaagcaatgc aggaagtgct    3420
gcagcagttc gcacatgtca aagattttgt ctggtgtcag gaggaaccgc ttaatcaggg    3480
ggcctggtat tgtagtcagc accatttccg ggaggtgatc ccgtttgggg cgtccttacg    3540
gtatgctggt cgccctgcct ccgcaagtcc ggccgtggga tatatgagcg ttcaccagaa    3600
acagcagcag gatttggtga atgatgcttt gaatgtggaa tgaatgtcca tcctgatcga    3660
caaaaacact aaagtaattt gtcagggctt taccggttcc cagggcacat ttcactcaga    3720
gcaggccatc gcttatggga ccaaaatggt gggtggtgta acgcctggta aaggaggcac    3780
cacccatctg ggtttgccgg tatttaatac cgtgcgtgag gcggttgccg caaccggtgc    3840
cacggcttca gttatctatg ttcctgcccc attttgtaaa gattcaattc tggaagctat    3900
tgatgcgggc atcaaattga ttattacgat taccgaaggt atccctacgc tggatatgtt    3960
gacggttaaa gtgaaacttg atgaagcggg ggtacgcatg attggtccga attgtccggg    4020
cgttattact ccaggtgagt gcaaaattgg tattcagccg ggtcatattc acaaacctgg    4080
gaaagtcgga attgtgtctc gttctggcac tctgacgtat gaggcagtta acagaccac    4140
agattatggc tttgggcaga gtacctgtgt cggcatcgga ggcgatccta ttccggggag    4200
taatttttatc gatattctgg aaatgtttga gaaagatccg cagaccgagg caatcgtcat    4260
gattggcgag attggcggtt ccgcggaaga agaagctgca gcctatatca agaacatgt    4320
cacaaaaccg gtagtgggct atatcgcggg agtcacggcc ccaaaaggta acgtatggg    4380
ccatgccgga gcgatcatcg cgggcggcaa aggcactgca gatgaaaaat ttgcagccct    4440
tgaggccgct ggcgtaaaaa cggtccgttc ccttgctgat attggtgaag cactgaaaac    4500
cgtgttgaaa taaaggtcca ggcatcaaat aaaacgaaag gctcagtcga agactgggc    4560
ctttcgtttt atctgttgtt tgtcggtgaa cgctctctac tagagtcaca ctggctcacc    4620
ttcgggtggg cctttctgcg tttatactcg agtgccacct gacgtctaag aaaccattat    4680
tatcatgaca ttaacctata aaaataggcg tatcacgagg cagaatttca gataaaaaaa    4740
```

```
atccttagct ttcgctaagg atgatttctg gaattcgcgg ccgcttctag agactagtgg      4800
aagacatcgc tagagacctg caccatatgc ggtgtgaaat accgcacaga tgcgtaagga      4860
gaaaataccg catcaggcgc cattcgccat tcaggctgcg caactgttgg aagggcgat       4920
cggtgcgggc ctcttcgcta ttacgccagc tggcgaaagg gggatgtgct gcaaggcgat      4980
taagttgggt aacgccaggg ttttcccagt cacgacgttg taaaacgacg ccagtgaat       5040
tcgagctcgg tacccgggga tcctctagag tcgacctgca ggcatgcaag cttggcgtaa      5100
tcatggtcat agctgtttcc tgtgtgaaat tgttatccgc tcacaattcc acacaacata     5160
cgagccggaa gcataaagtg taaagcctgg ggtgcctaat gagtgagcta actcacatta     5220
attgcgttgc gctcactgcc cgctttccag tcgggaaacc tgtcgtgcca gctgcattaa     5280
tgaatcggcc aacgcgcggg ggtttataaa atcccgtcaa gtcagcgtaa tgctctgcca     5340
gtgttacaac caattaacca attctgatta gaaaaactca tcgagcatca aatgaaactg     5400
caatttattc atatcaggat tatcaatacc atattttga aaaagccgtt tctgtaatga     5460
aggagaaaac tcaccgaggc agttccatag gatggcaaga tcctggtatc ggtctgcgat     5520
tccgactcgt ccaacatcaa tacaacctat taatttcccc tcgtcaaaaa taaggttatc     5580
aagtgagaaa tcaccatgag tgacgactga atccggtgag aatggcaaaa gcttatgcat     5640
ttctttccag acttgttcaa caggccagcc attacgctcg tcatcaaaat cactcgcatc     5700
aaccaaaccg ttattcattc gtgattgcgc ctgagcgaga cgaaatacgc gatcgctgtt     5760
aaaaggacaa ttacaaacag gaatcgaatg caaccggcgc aggaacactg ccagcgcatc     5820
aacaatattt tcacctgaat caggatattc ttctaatacc tggaatgctg ttttcccggg     5880
gatcgcagtg gtgagtaacc atgcatcatc aggagtacgg ataaaatgct tgatggtcgg     5940
aagaggcata aattccgtca gccagtttag tctgaccatc tcatctgtaa catcattggc     6000
aacgctacct ttgccatgtt tcagaaacaa ctctggcgca tcgggcttcc catacaatcg     6060
atagattgtc gcacctgatt gcccgacatt atcgcgagcc catttatacc catataaatc     6120
agcatccatg ttggaattta atcgcggcct ggagcaagac gtttcccgtt gaatatggct     6180
cataacaccc cttgtattac tgtttatgta agcagacagt tttattgttc atgatgatat     6240
atttttatct tgtgcaatgt aacatcagag attttgagac acaacgtggc tttgttgaat     6300
aaatcgaact tttgctgagt tgaaggatca gggtctcttg ccatgtcttc tactagtagc     6360
ggccgctgca gtccggcaaa aaagggcaag gtgtcaccac cctgcccttt ttctttaaaa     6420
ccgaaaagat tacttcgcgt tatgcaggct tcctcgctca ctgactcgct gcgctcggtc     6480
gttcggctgc ggcgagcggt atcagctcac tcaaaggcgg taatacggtt atccacagaa     6540
tcaggggata acgcaggaaa gaacatgtga gcaaaaggcc agcaaaaggc caggaaccgt     6600
aaaaaggc                                                              6608
```

<210> SEQ ID NO 7
<211> LENGTH: 9517
<212> TYPE: DNA
<213> ORGANISM: Escherichia coli

<400> SEQUENCE: 7

```
cgcgttgctg gcgttttttcc acaggctccg ccccctgac gagcatcaca aaaatcgacg       60
ctcaagtcag aggtggcgaa acccgacagg actataaaga taccaggcgt ttccccctgg      120
aagctccctc gtgcgctctc ctgttccgac cctgccgctt accggatacc tgtccgcctt      180
tctcccttcg ggaagcgtgg cgctttctca tagctcacgc tgtaggtatc tcagttcggt      240
```

```
gtaggtcgtt cgctccaagc tgggctgtgt gcacgaaccc cccgttcagc ccgaccgctg    300
cgccttatcc ggtaactatc gtcttgagtc caacccggta agacacgact tatcgccact    360
ggcagcagcc actggtaaca ggattagcag agcgaggtat gtaggcggtg ctacagagtt    420
cttgaagtgg tggcctaact acggctacac tagaagaaca gtatttggta tctgcgctct    480
gctgaagcca gttaccttcg gaaaaagagt tggtagctct tgatccggca aacaaaccac    540
cgctggtagc ggtggttttt ttgtttgcaa gcagcagatt acgcgcagaa aaaaaggatc    600
tcaagaagat cctttgatct tttctacggg gtctgacgct cagtggaacg aaaactcacg    660
ttaagggatt ttggtcatga gattatcaaa aaggatcttc acctagatcc ttttaaatta    720
aaaatgaagt tttaaatcaa tctaaagtat atatgagtaa acttggtctg acagctcgag    780
gtaggcctga taagacgcgc aagcgtcgca tcaggcaacc agtgccggat gcggcgtgaa    840
cgccttatcc ggcctacaag tcattacccg taggcctgat aagcgcagcg catcaggcgt    900
aacaagaaaa tgcaggaaat ctttaaaaac tgccccctgac actaagacag tttttaaagg    960
ttccttcgcg agccactacg tagacaagag ctcgcaagtg aaccccggca cgcacatcac   1020
tgtgcgtggt agtatccacg gcgaagtaag cataaaaaag atgcttaagg gatcacgaat   1080
gcagaacagc gctttgaaag cctggttgga ctcttcttac ctctctggcg caaaccagag   1140
ctggatagaa cagctctatg aagatttctt aaccgatcct gactcggttg acgctaactg   1200
gcgttcgacg ttccagcagt tacctggtac gggagtcaaa ccggatcaat tccactctca   1260
aacgcgtgaa tatttccgcc gctggcgaa agacgcttca cgttactctt caacgatctc   1320
cgaccctgac accaatgtga agcaggttaa agtcctgcag ctcattaacg cataccgctt   1380
ccgtggtcac cagcatgcga atctcgatcc gctgggactg tggcagcaag ataaagtggc   1440
cgatctggat ccgtctttcc acgatctgac cgaagcagac ttccaggaga ctttcaacgt   1500
cggttcattt gccagcggca agaaaccat gaaactcggc gagctgctgg aagccctcaa   1560
gcaaacctac tgcggcccga ttggtgccga gtatatgcac attaccagca ccgaagaaaa   1620
acgctggatc caacagcgta tcgagtctgg tcgcgcgact ttcaatagcg aagagaaaaa   1680
acgcttctta agcgaactga ccgccgctga aggtcttgaa cgttacctcg cgcaaaaatt   1740
ccctggcgca aaacgcttct cgctggaagg cggtgacgcg ttaatcccga tgcttaaaga   1800
gatgatccgc cacgctggca acagcggcac ccgcgaagtg gttctcggga tggcgcaccg   1860
tggtcgtctg aacgtgctgg tgaacgtgct gggtaaaaaa ccgcaagact tgttcgacga   1920
gttcgccgga aaacataaag aacacctcgg cacgggtgac gtgaaatacc acatgggctt   1980
ctcgtctgac ttccagaccg atggcggcct ggtgcacctg gcgctggcgt taacccgtc    2040 tcaccttgag attgtaagcc cggtagttat cggttctgtt cgtgcccgtc tggacagact   2100
tgatgagccg agcagcaaca aagtgctgcc aatcaccatc cacggtgacg ccgcagtgac   2160
cgggcagggc gtggttcagg aaaccctgaa catgtcgaaa gcgcgtggtt atgaagttgg   2220
cggtacggta cgtatcgtta tcaacaacca ggttggtttc accacctcta atccgctgga   2280
tgcccgttct acgccgtact gtactgatat cggtaagatg gttcaggccc cgattttcca   2340
cgttaacgcg gacgatccgg aagccgttgc ctttgtgacc cgtctggcgc tcgatttccg   2400
taacaccttt aaacgtgatg ttttcatcga cctggtgtgc taccgccgtc acggccacaa   2460
cgaagccgac gagccgagcg caacccagcc gctgatgtat cagaaaatca aaaacatcc    2520 gacaccgcgc aaaatctacg ctgacaagct ggagcaggaa aaagtggcga cgctggaaga   2580
tgccaccgag atggttaacc tgtaccgcga tgcgctggat gctggcgatt gcgtagtggc   2640
```

```
agagtggcgt ccgatgaaca tgcactcttt cacctggtcg ccgtacctca accacgaatg   2700
ggacgaagag tacccgaaca aagttgagat gaagcgcctg caggagctgg cgaaacgcat   2760
cagcacggtg ccggaagcag ttgaaatgca gtctcgcgtt gccaagattt atggcgatcg   2820
ccaggcgatg gctgccggtg agaaactgtt cgactgggcg gtgcggaaa acctcgctta   2880 cgccacgctg gttgatgaag gcattccggt tcgcctgtcg ggtgaggact ccggtcgcgg   2940
taccttcttc caccgccacg cggtgatcca caaccagtct aacggttcca cttacacgcc   3000
gctgcaacat atccataacg ggcagggcgc gttccgtgtc tgggactccg tactgtctga   3060
agaagcagtg ctggcgtttg aatatggtta tgccaccgca gaaccacgca ctctgaccat   3120
ctgggaagcg cagttcggtg acttcgccaa cggtgcgcag gtggttatcg accagttcat   3180
ctcctctggc gaacagaaat ggggccggat gtgtggtctg gtgatgttgc tgccgcacgg   3240
ttacgaaggg caggggccgg agcactcctc cgcgcgtctg aacgttatc tgcaactttg   3300 tgctgagcaa acatgcagg tttgcgtacc gtctaccccg gcacaggttt accacatgct   3360
gcgtcgtcag gcgctgcgcg ggatgcgtcg tccgctggtc gtgatgtcgc cgaaatccct   3420
gctgcgtcat ccgctggcgg tttccagcct cgaagaactg gcgaacggca ccttcctgcc   3480
agccatcggt gaaatcgacg agcttgatcc gaagggcgtg aagcgcgtag tgatgtgttc   3540
tggtaaggtt tattacgacc tgctggaaca gcgtcgtaag aacaatcaac acgatgtcgc   3600
cattgtgcgt atcgagcaac tctaccgtt cccgcataaa gcgatgcagg aagtgttgca   3660
gcagtttgct cacgtcaagg attttgtctg gtgccaggaa gagccgctca accagggcgc   3720
atggtactgc agccagcatc atttccgtga agtgattccg tttggggctt ctctgcgtta   3780
tgcaggccgc ccggcctccg cctctccggc ggtagggtat atgtccgttc accagaaaca   3840
gcaacaagat ctggttaatg acgcgctgaa cgtcgaataa ataaaggata cacaatgagt   3900
agcgtagata ttctggtccc tgacctgcct gaatccgtag ccgatgccac cgtcgcaacc   3960
tggcataaaa aacccggcga cgcagtcgta cgtgatgaag tgctggtaga aatcgaaact   4020
gacaaagtgg tactggaagt accggcatca gcagacggca ttctggatgc ggttctggaa   4080
gatgaaggta caacggtaac gtctcgtcag atccttggtc gcctgcgtga aggcaacagc   4140
gccggtaaag aaaccagcgc caaatctgaa gagaaagcgt ccactccggc gcaacgccag   4200
caggcgtctc tggaagagca aaacaacgat gcgttaagcc cggcgatccg tcgcctgctg   4260
gctgaacaca atctcgacgc cagcgccatt aaaggcaccg gtgtgggtgg tcgtctgact   4320
cgtgaagatg tggaaaaaca tctggcgaaa gccccggcga aagagtctgc tccggcagcg   4380
gctgctccgg cggcgcaacc ggctctggct gcacgtagtg aaaaacgtgt cccgatgact   4440
cgcctgcgta gcgtgtggc agagcgtctg ctggaagcga aaactccac cgccatgctg   4500 accacgttca acgaagtcaa catgaagccg attatggatc tgcgtaagca gtacggtgaa   4560
gcgtttgaaa acgccacgg catccgtctg ggctttatgt ccttctacgt gaaagcggtg   4620
gttgaagccc tgaaacgtta cccggaagtg aacgcttcta tcgacggcga tgacgtggtt   4680
taccacaact atttcgacgt cagcatggcg gtttctacgc cgcgcggcct ggtgacgccg   4740
gttctgcgtg atgtcgatac cctcggcatg cagacatcg agaagaaaat caaagagctg   4800
gcagtcaaag gccgtgacgg caagctgacc gttgaagatc tgaccggtgg taacttcacc   4860
atcaccaacg gtggtgtgtt cggttccctg atgtctacgc cgatcatcaa cccgccgcag   4920
agcgcaattc tgggtatgca cgctatcaaa gatcgtccga tggcggtgaa tggtcaggtt   4980
gagatcctgc cgatgatgta cctggcgctg tcctacgatc accgtctgat cgatggtcgc   5040
```

```
gaatccgtgg gcttcctggt aacgatcaaa gagttgctgg aagatccgac gcgtctgctg    5100
ctggacgtgt agtagtttaa gtttcacctg cactgtagac cggataaggc attatcgcct    5160
tctccggcaa ttgaagcctg atgcgacgct gacgcgtctt atcaggccta cgggaccacc    5220
aatgtaggtc ggataaggcg caagcgccgc atccgacaag cgatgcctga tgtgacgttt    5280
aacgtgtctt atcaggccta cgggtgaccg acaatgcccg aagcgatac gaaatattcg     5340 gtctacggtt aaaagataa cgattactga aggatggaca aacacatga acttacatga      5400 atatcaggca aaacaacttt tgcccgcta tggcttacca gcaccggtgg gttatgcctg     5460
tactactccg cgcgaagcag aagaagccgc ttcaaaaatc ggtgccggtc cgtgggtagt    5520
gaaatgtcag gttcacgctg gtggccgcgg taaagcgggc ggtgtgaaag ttgtaaacag    5580
caaagaggac atccgtgctt ttgcagaaaa ctggctgggc aagcgtctgg taacgtatca    5640
aacagatgcc aatggccaac cggttaacca gattctggtt gaagcagcga ccgatatcgc    5700
taaagagctg tatctcggtg ccgttgttga ccgtagttcc cgtcgtgtgg tctttatggc    5760
ctccaccgaa ggcggcgtgg aaatcgaaaa agtggcggaa gaaactccgc acctgatcca    5820
taaagttgcg cttgatccgc tgactggccc gatgccgtat cagggacgcg agctggcgtt    5880
caaactgggt ctggaaggta aactggttca gcagttcacc aaaatcttca tgggcctggc    5940
gaccattttc ctggagcgcg acctggcgtt gatcgaaatc aacccgctgg tcatcaccaa    6000
acagggcgat ctgatttgcc tcgacggcaa actgggcgct gacggcaacg cactgttccg    6060
ccagcctgat ctgcgcgaaa tgcgtgacca gtcgcaggaa gatccgcgtg aagcacaggc    6120
tgcacagtgg gaactgaact acgttgcgct ggacggtaac atcggttgta tggttaacgg    6180
cgcaggtctg gcgatgggta cgatggacat cgttaaactg cacggcggcg aaccggctaa    6240
cttccttgac gttggcggcg cgcaaccaa agaacgtgta accgaagcgt tcaaaatcat     6300
cctctctgac gacaaagtga agccgttctc ggttaacatc ttcggcggta tcgttcgttg    6360
cgacctgatc gctgacggta tcatcggcgc ggtagcagaa gtgggtgtta acgtaccggt    6420
cgtggtacgt ctggaaggta acaacgccga actcggcgcg aagaaactgg ctgacagcgg    6480
cctgaatatt attgcagcaa aaggtctgac ggatgcagct cagcaggttg ttgccgcagt    6540 ggagggaaa taatgtccat tttaatcgat aaaaacacca aggttatctg ccagggcttt     6600
accggtagcc aggggacttt ccactcagaa caggccattg catacggcac taaaatggtt    6660
ggcggcgtaa ccccaggtaa aggcggcacc acccacctcg gcctgccggt gttcaacacc    6720
gtgcgtgaag ccgttgctgc cactggcgct accgcttctg ttatctacgt accagcaccg    6780
ttctgcaaag actccattct ggaagccatc gacgcaggca tcaaactgat tatcaccatc    6840
actgaaggca tcccgacgct ggatatgctg accgtgaaag tgaagctgga tgaagcaggc    6900
gttcgtatga tcggcccgaa ctgcccaggc gttatcactc cgggtgaatg caaaatcggt    6960
atccagcctg gtcacattca caaaccgggt aaagtgggta tcgtttcccg ttccggtaca    7020
ctgacctatg aagcggttaa acagaccacg gattacggtt tcggtcagtc gacctgtgtc    7080
ggtatcggcg gtgacccgat cccgggctct aactttatcg acattctcga aatgttcgaa    7140
aaagatccgc agaccgaagc gatcgtgatg atcggtgaga tcggcggtag cgctgaagaa    7200
gaagcagctg cgtacatcaa agagcacgtt accaagccag ttgtgggtta catcgctggt    7260
gtgactgcgc cgaaaggcaa acgtatgggc cacgcgggtg ccatcattgc cggtgggaaa    7320
gggactgcgg atgagaaatt cgctgctctg gaagccgcag gcgtgaaaac cgttcgcagc    7380
ctggcggata tcggtgaagc actgaaaact gttctgaaat aaaggtccag gcatcaaata    7440
```

| | |
|---|---|
| aaacgaaagg ctcagtcgaa agactgggcc tttcgtttta tctgttgttt gtcggtgaac | 7500 |
| gctctctact agagtcacac tggctcacct tcgggtgggc ctttctgcgt ttatactcga | 7560 |
| gtgccacctg acgtctaaga aaccattatt atcatgacat taacctataa aaataggcgt | 7620 |
| atcacgaggc agaatttcag ataaaaaaaa tccttagctt tcgctaagga tgatttctgg | 7680 |
| aattcgcggc cgcttctaga gactagtgga agacatcgct agagacctgc accatatgcg | 7740 |
| gtgtgaaata ccgcacagat gcgtaaggag aaaataccgc atcaggcgcc attcgccatt | 7800 |
| caggctgcgc aactgttggg aagggcgatc ggtgcgggcc tcttcgctat tacgccagct | 7860 |
| ggcgaaaggg ggatgtgctg caaggcgatt aagttgggta acgccagggt ttcccagtc | 7920 |
| acgacgttgt aaaacgacgg ccagtgaatt cgagctcggt acccggggat cctctagagt | 7980 |
| cgacctgcag gcatgcaagc ttggcgtaat catggtcata gctgtttcct gtgtgaaatt | 8040 |
| gttatccgct cacaattcca cacaacatac gagccggaag cataaagtgt aaagcctggg | 8100 |
| gtgcctaatg agtgagctaa ctcacattaa ttgcgttgcg ctcactgccc gctttccagt | 8160 |
| cgggaaacct gtcgtgccag ctgcattaat gaatcggcca acgcgcgggg gtttataaaa | 8220 |
| tcccgtcaag tcagcgtaat gctctgccag tgttacaacc aattaaccaa ttctgattag | 8280 |
| aaaaactcat cgagcatcaa atgaaactgc aatttattca tatcaggatt atcaatacca | 8340 |
| tatttttgaa aaagccgttt ctgtaatgaa ggagaaaact caccgaggca gttccatagg | 8400 |
| atggcaagat cctggtatcg gtctgcgatt ccgactcgtc aacatcaat acaacctatt | 8460 |
| aatttcccct cgtcaaaaat aaggttatca agtgagaaat caccatgagt gacgactgaa | 8520 |
| tccggtgaga atggcaaaag cttatgcatt tctttccaga cttgttcaac aggccagcca | 8580 |
| ttacgctcgt catcaaaatc actcgcatca accaaaccgt tattcattcg tgattgcgcc | 8640 |
| tgagcgagac gaaatacgcg atcgctgtta aaaggacaat tacaaacagg aatcgaatgc | 8700 |
| aaccggcgca ggaacactgc cagcgcatca acaatatttt cacctgaatc aggatattct | 8760 |
| tctaatacct ggaatgctgt tttcccgggg atcgcagtgg tgagtaacca tgcatcatca | 8820 |
| ggagtacgga taaaatgctt gatggtcgga agaggcataa attccgtcag ccagtttagt | 8880 |
| ctgaccatct catctgtaac atcattggca acgctacctt tgccatgttt cagaaacaac | 8940 |
| tctggcgcat cgggcttccc atacaatcga tagattgtcg cacctgattg cccgacatta | 9000 |
| tcgcgagccc atttataccc atataaatca gcatccatgt tggaatttaa tcgcggcctg | 9060 |
| gagcaagacg tttcccgttg aatatggctc ataacacccc ttgtattact gtttatgtaa | 9120 |
| gcagacagtt ttattgttca tgatgatata tttttatctt gtgcaatgta acatcagaga | 9180 |
| ttttgagaca caacgtggct ttgttgaata atcgaactt tgctgagtt gaaggatcag | 9240 |
| ggtctcttgc catgtcttct actagtagcg gccgctgcag tccggcaaaa aagggcaagg | 9300 |
| tgtcaccacc ctgcccttt tctttaaaac cgaaagatt acttcgcgtt atgcaggctt | 9360 |
| cctcgctcac tgactcgctg cgctcggtcg ttcggctgcg gcgagcggta tcagctcact | 9420 |
| caaaggcggt aatacggtta tccacagaat caggggataa cgcaggaaag aacatgtgag | 9480 |
| caaaaggcca gcaaaaggcc aggaaccgta aaaggc | 9517 |

<210> SEQ ID NO 8
<211> LENGTH: 7116
<212> TYPE: DNA
<213> ORGANISM: Escherichia coli

```
<400> SEQUENCE: 8
tactgcgcca tccgttagca gttagcagcc tggaggaact ggcaaacggt acgttcttgc      60
cagctatcgg cgaaatcgat gaactggatc ctaaaggggt gaaacgcgtt gttatgtgtt     120
ctggtaaagt gtattatgat cttttggaac agcgtcgcaa aaataatcag cacgatgtag     180
ctattgtgcg gatcgagcag ctgtatccgt tcccgcacaa agcaatgcag gaagtgctgc     240
agcagttcgc acatgtcaaa gattttgtct ggtgtcagga ggaaccgctt aatcaggggg     300
cctggtattg tagtcagcac catttccggg aggtgatccc gtttgggcg tccttacggt      360
atgctggtcg ccctgcctcc gcaagtccgg ccgtgggata tatgagcgtt caccagaaac     420
agcagcagga tttggtgaat gatgcttttga atgtggaatg aatgtccatc ctgatcgaca     480
aaaacactaa agtaatttgt cagggcttta ccgttccca gggcacattt cactcagagc      540
aggccatcgc ttatgggacc aaaatggtgg gtggtgtaac gcctggtaaa ggaggcacca     600
cccatctggg tttgccggta tttaataccg tgcgtgaggc ggttgccgca accggtgcca     660
cggcttcagt tatctatgtt cctgccccat tttgtaaaga ttcaattctg gaagctattg     720
atgcgggcat caaattgatt attacgatta ccgaaggtat ccctacgctg gatatgttga     780
cggttaaagt gaaacttgat gaagcggggg tacgcatgat tggtccgaat tgtccgggcg     840
ttattactcc aggtgagtgc aaaattggta ttcagccggg tcatattcac aaacctggga     900
aagtcggaat tgtgtctcgt tctggcactc tgacgtatga ggcagttaaa cagaccacag     960
attatggctt tgggcagagt acctgtgtcg gcatcggagg cgatcctatt ccggggagta    1020
attttatcga tattctggaa atgtttgaga aagatccgca gaccgaggca atcgtcatga    1080
ttggcgagat tggcggttcc gcggaagaag aagctgcagc ctatatcaaa gaacatgtca    1140
caaaaccggt agtgggctat atcgcggag tcacggcccc aaaaggtaaa cgtatgggcc      1200
atgccggagc gatcatcgcg ggcggcaaag gcactgcaga tgaaaaattt gcagcccttg    1260
aggccgctgg cgtaaaaacg gtccgttccc ttgctgatat tggtgaagca ctgaaaccg     1320
tgttgaaata aggtccagg catcaaataa acgaaaggc tcagtcgaaa gactgggcct      1380
ttcgttttat ctgttgtttg tcggtgaacg ctctctacta gagtcacact ggctcacctt    1440
cgggtgggcc tttctgcgtt tatatcccgt caagtcagcg taatgctctg ccagtgttac    1500
aaccaattaa ccaattctga ttagaaaaac tcatcgagca tcaaatgaaa ctgcaattta    1560
ttcatatcag gattatcaat accatatttt tgaaaagcc gtttctgtaa tgaaggagaa     1620
aactcaccga gcagttcca taggatggca agatcctggt atcggtctgc gattccgact     1680
cgtccaacat caatacaacc tattaatttc ccctcgtcaa aaataaggtt atcaagtgag    1740
aaatcaccat gagtgacgac tgaatccggt gagaatggca aaagcttatg catttctttc    1800
cagacttgtt caacaggcca gccattacgc tcgtcatcaa aatcactcgc atcaaccaaa    1860
ccgttattca ttcgtgattg cgcctgagcg agacgaaata cgcgatcgct gttaaaagga    1920
caattacaaa caggaatcga atgcaaccgg cgcaggaaca ctgccagcgc atcaacaata    1980
ttttcacctg aatcaggata ttcttctaat acctggaatg ctgttttccc ggggatcgca    2040
gtggtgagta accatgcatc atcaggagta cggataaaat gcttgatggt cggaagaggc    2100
ataaattccg tcagccagtt tagtctgacc atctcatctg taacatcatt ggcaacgcta    2160
cctttgccat gtttcagaaa caactctggc gcatcgggct tcccatacaa tcgatagatt    2220
gtcgcacctg attgcccgac attatcgcga gcccatttat acccatataa atcagcatcc    2280
atgttggaat ttaatcgcgg cctggagcaa gacgtttccc gttgaatatg gctcataaca    2340
```

-continued

```
ccccttgtat tactgtttat gtaagcagac agttttattg ttcatgatga tatattttta    2400
tcttgtgcaa tgtaacatca gagattttga gacacaacgt ggctttgttg aataaatcga    2460
acttttgctg agttgaagga tcagctcgag tgccacctga cgtctaagaa accattatta    2520
tcatgacatt aacctataaa aataggcgta tcacgaggca gaatttcaga taaaaaaaat    2580
ccttagcttt cgctaaggat gatttctgga attcgcggcc gcttctagag actagtggaa    2640
gacatcgctg gaaagtgaaa cgtgatttca tgcgtcattt tgaacatttt gtaaatctta    2700
tttaataatg tgtgcggcaa ttcacattta atttatgaat gttttcttaa catcgcggca    2760
actcaagaaa cggcaggttc ggatcttagc tactagagaa agaggagaaa tactagatgc    2820
gtaaaggcga agagctgttc actggtgtcg tccctattct ggtggaactg gatggtgatg    2880
tcaacggtca taagttttcc gtgcgtggcg agggtgaagg tgacgcaact aatggtaaac    2940
tgacgctgaa gttcatctgt actactggta aactgccggt tccttggccg actctggtaa    3000
cgacgctgac ttatggtgtt cagtgctttg ctcgttatcc ggaccatatg aagcagcatg    3060
acttcttcaa gtccgccatg ccggaaggct atgtgcagga acgcacgatt cctttaagg     3120 atgacggcac gtacaaaacg cgtgcggaag tgaaatttga aggcgatacc ctggtaaacc    3180
gcattgagct gaaaggcatt gactttaaag aggacggcaa tatcctgggc cataagctgg    3240
aatacaattt taacagccac aatgtttaca tcaccgccga taaacaaaaa aatggcatta    3300
aagcgaattt taaaattcgc cacaacgtgg aggatgcag cgtgcagctg ctgatcact     3360 accagcaaaa cactccaatc ggtgatggtc ctgttctgct gccagacaat cactatctga    3420
gcacgcaaag cgttctgtct aaagatccga acgagaaacg cgatcatatg gttctgctgg    3480
agttcgtaac cgcagcgggc atcacgcatg gtatggatga actgtacaaa tgaccaggca    3540
tcaaataaaa cgaaaggctc agtcgaaaga ctgggccttt cgttttatct gttgtttgtc    3600
ggtgaacgct ctctactaga gtcacactgg ctcaccttcg ggtgggcctt tctgcgttta    3660
tacgtgccat gtcttctact agtagcggcc gctgcagtcc ggcaaaaaag gcaaggtgt     3720 caccacccctg ccctttttct ttaaaaccga aaagattact cgcgttatg caggcttcct    3780 cgctcactga ctcgctgcgc tcggtcgttc ggctgcggcg agcggtatca gctcactcaa    3840
aggcggtaat acggttatcc acagaatcag gggataacgc aggaaagaac atgtgagcaa    3900
aaggccagca aaaggccagg aaccgtaaaa aggccgcgtt gctggcgttt ttccacaggc    3960
tccgcccccc tgacgagcat cacaaaaatc gacgctcaag tcagaggtgg cgaaacccga    4020
caggactata aagataccag gcgtttcccc ctggaagctc cctcgtgcgc tctcctgttc    4080
cgaccctgcc gcttaccgga tacctgtccg cctttctccc ttcgggaagc gtggcgcttt    4140
ctcatagctc acgctgtagg tatctcagtt cggtgtaggt cgttcgctcc aagctgggct    4200
gtgtgcacga accccccgtt cagcccgacc gctgcgcctt atccggtaac tatcgtcttg    4260
agtccaaccc ggtaagacac gacttatcgc cactggcagc agccactggt aacaggatta    4320
gcagagcgag gtatgtaggc ggtgctacag agttcttgaa gtggtggcct aactacggct    4380
acactagaag aacagtattt ggtatctgcg ctctgctgaa gccagttacc ttcggaaaaa    4440
gagttggtag ctcttgatcc ggcaaacaaa ccaccgctgg tagcggtggt ttttttgttt    4500
gcaagcagca gattacgcgc agaaaaaaag gatctcaaga agatcctttg atcttttcta    4560
cggggtctga cgctcagtgg aacgaaaact cacgttaagg gattttggtc atgagattat    4620
caaaaaggat cttcacctag atcctttaa attaaaaatg aagttttaaa tcaatctaaa     4680
gtatatatga gtaaacttgg tctgacagct cgagtttacg gctagctcag tcctaggtat    4740
```

```
agtgctagct acttgttaga aaagagaagc acgtaatgca gaactcagca ttgaaagcat    4800
ggcttgatag ctcctatttt atcaggtgcta accagagctg gattgaacag ctgtatgaag    4860
attttctgac agatccggat tcagtggatg cgaattggcg cagcactttt cagcagttgc    4920
ctggcaccgg tgtaaaaccg gatcagtttc attcccagac gcgggagtat tttcgtcgtc    4980
tggcgaaaga tgcgagccgg tattcaagta caatttctga tccggatacg aatgtaaaac    5040
aggtgaaagt gcttcagtta attaatgcgt atcgctttag aggccatcag catgcgaatc    5100
tggatccgct gggcttatgg cagcaggata aagtcgcgga tctggatcca gttttcacg     5160
atttaacgga agctgatttt caggaaacct ttaacgtcgg ctcattcgca agtgggaaag    5220
aaacaatgaa actgggcgaa cttcttgagg cgctgaaaca gacttattgt ggccctattg    5280
gtgcggaata tatgcatatt acctcaactg aagagaaacg ttggattcag cagagaatcg    5340
agagtggccg cgcgactttt aactccgaag aaaaaaaaag attcctgtca gaactgacag    5400
ccgcggaagg cttagagcgg tatttggggtg ccaaattccc aggagcaaaa cggttcagcc    5460
tggagggcgg tgatgcgctg atcccgatgc tgaaagaaat gattcggcat gcgggaaata    5520
gcggaactcg ggaagtggtg ttaggaatgg cacaccgcgg ccgtttgaat gtactggtta    5580
acgtattagg aaaaaaacct caggatttat ttgatgagtt cgcgggaaaa cataaagaac    5640
atctgggcac tggtgatgtc aaatatcaca tgggcttctc aagtgatttt cagacggatg    5700
gaggtctggt tcacctggca ctggcatttt atccttctca tctggaaatc gtaagtccgg    5760
tcgttattgg ttccgtgcgc gctcgcttag atcggttaga tgaacctagc tcaaacaaag    5820
ttttaccaat cacgatccat ggggatgcag ctgttaccgg acagggtgtt gtgcaggaga    5880
ctttgaatat gtccaaagcg cgcgggtatg aggtgggtgg tacggtgcgt attgttatca    5940
ataatcaggt gggttttaca accagtaacc ctctggatgc tcgctctacg ccgtattgca    6000
ctgatattgg taaaatggtg caggcaccaa ttttttcacgt caatgccgat gatccggaag    6060
ctgttgcctt tgttacgcgc ctggctctgg attttcgtaa cactttcaaa cgtgatgtat    6120
ttatcgattt agtatgctat cgtcgtcatg gtcataatga ggctgatgaa cctagcgcta    6180
cccagccact gatgtatcag aaaattaaaa aacatcctac ccctcgtaaa atttatgcgg    6240
ataaactgga gcaggaaaaa gtggctactc ttgaagatgc tactgaaatg gtcaatctttt    6300
atcgggatgc attggatgcg ggtgattgcg tggtcgcgga atggcgcccg atgaatatgc    6360
attcatttac ttggtcaccg tatttaaatc atgagtggga tgaggaatat ccgaataaag    6420
tggagatgaa acgcctgcag gaattagcaa aacgtattag cacagtacct gaagcggttg    6480
agatgcagtc tagagttgcc aaaatctatg gagatcgcca ggccatggca gcagggggaaa   6540
aacttttga ttggggggga gccgaaaacc tggcatatgc gacgctggta gatgagggca    6600
ttccggtgcg ccttttctggt gaagattctg ggcgcggtac ttttttttcat cggcacgctg    6660
ttattcataa ccagtctaac ggtagtactt atactccgct gcagcacatc cacaatggtc    6720
agggtgcgtt ccgtgtatgg gattccgtgc tgagtgaaga gcggttctt gcgtttgagt     6780
atgggtatgc aactgccgag ccacgcacgc tgacgatctg ggaagcccag tttggcgatt    6840
ttgcaaatgg tgcccaggtg gtaatcgatc agtttattag ctccggcgaa cagaaatggg    6900
ggcggatgtg tggtttagtt atgttgttac cgcatggcta tgaaggtcag ggacctgagc    6960
acagctcagc gcgcctggaa cgctatcttc agctgtgtgc ggaacagaac atgcaggtat    7020
gcgttccttc cacgccggct caggtttatc atatgttaag acgtcaggcc ttgcgcggta    7080
tgcggcgccc gttggtcgtg atgtccccga aaagtt                               7116
```

```
<210> SEQ ID NO 9
<211> LENGTH: 10025
<212> TYPE: DNA
<213> ORGANISM: Escherichia coli

<400> SEQUENCE: 9
cgcgttgctg gcgttttcc  acaggctccg cccccctgac gagcatcaca aaaatcgacg      60
ctcaagtcag aggtggcgaa acccgacagg actataaaga taccaggcgt ttccccctgg     120
aagctccctc gtgcgctctc ctgttccgac cctgccgctt accggatacc tgtccgcctt     180
tctcccttcg ggaagcgtgg cgctttctca tagctcacgc tgtaggtatc tcagttcggt     240
gtaggtcgtt cgctccaagc tgggctgtgt gcacgaaccc cccgttcagc ccgaccgctg     300
cgccttatcc ggtaactatc gtcttgagtc caacccggta agacacgact tatcgccact     360
ggcagcagcc actggtaaca ggattagcag agcgaggtat gtaggcggtg ctacagagtt     420
cttgaagtgg tggcctaact acggctacac tagaagaaca gtatttggta tctgcgctct     480
gctgaagcca gttaccttcg gaaaaagagt tggtagctct tgatccggca acaaaccac      540 cgctggtagc ggtggttttt tgtttgcaa  gcagcagatt acgcgcagaa aaaaggatc      600 tcaagaagat cctttgatct tttctacggg gtctgacgct cagtggaacg aaaactcacg     660
ttaagggatt ttggtcatga gattatcaaa aaggatcttc acctagatcc ttttaaatta     720
aaaatgaagt tttaaatcaa tctaaagtat atatgagtaa acttggtctg acagctcgag     780
gtaggcctga taagacgcgc aagcgtcgca tcaggcaacc agtgccggat gcggcgtgaa     840
cgccttatcc ggcctacaag tcattacccg taggcctgat aagcgcagcg catcaggcgt     900 aacaagaaa  tgcaggaaat ctttaaaaac tgcccctgac actaagacag tttttaaagg     960
ttccttcgcg agccactacg tagacaagag ctcgcaagtg aaccccggca cgcacatcac    1020
tgtgcgtggt agtatccacg gcgaagtaag cataaaaaag atgcttaagg gatcacgaat    1080
gcagaacagc gctttgaaag cctggttgga ctcttcttac ctctctggcg caaaccagag    1140
ctggatagaa cagctctatg aagatttctt aaccgatcct gactcggttg acgctaactg    1200
gcgttcgacg ttccagcagt tacctggtac gggagtcaaa ccggatcaat tccactctca    1260
aacgcgtgaa tatttccgcc gcctggcgaa agacgcttca cgttactctt caacgatctc    1320
cgaccctgac accaatgtga agcaggttaa agtcctgcag ctcattaacg cataccgctt    1380
ccgtggtcac cagcatgcga atctcgatcc gctgggactg tggcagcaag ataaagtggc    1440
cgatctggat ccgtctttcc acgatctgac cgaagcagac ttccaggaga ctttcaacgt    1500
cggttcattt gccagcggca agaaaccat  gaaactcggc gagctgctgg aagccctcaa    1560
gcaaacctac tgcggcccga ttggtgccga gtatatgcac attaccagca ccgaagaaaa    1620
acgctggatc caacagcgta tcgagtctgg tcgcgcgact ttcaatagcg aagagaaaaa    1680
acgcttctta agcgaactga ccgccgctga aggtcttgaa cgttacctcg cgcaaaatt     1740 ccctggcgca aaacgcttct cgctggaagg cgtgacgcg  ttaatcccga tgcttaaaga    1800
gatgatccgc cacgctggca acagcggcac ccgcgaagtg gttctcggga tggcgcaccg    1860
tggtcgtctg aacgtgctgg tgaacgtgct gggtaaaaaa ccgcaagact tgttcgacga    1920
gttcgccggt aaacataaag aacacctcgg cacgggtgac gtgaaatacc acatgggctt    1980
ctcgtctgac ttccagaccg atggcggcct ggtgcacctg gcgctggcgt ttaacccgtc    2040
tcaccttgag attgtaagcc cggtagttat cggttctgtt cgtgcccgtc tggacagact    2100
tgatgagccg agcagcaaca aagtgctgcc aatcaccatc cacggtgacg ccgcagtgac    2160
```

```
cgggcagggc gtggttcagg aaaccctgaa catgtcgaaa gcgcgtggtt atgaagttgg    2220
cggtacggta cgtatcgtta tcaacaacca ggttggtttc accacctcta atccgctgga    2280
tgcccgttct acgccgtact gtactgatat cggtaagatg gttcaggccc cgattttcca    2340
cgttaacgcg gacgatccgg aagccgttgc ctttgtgacc cgtctggcgc tcgatttccg    2400
taacaccttt aaacgtgatg ttttcatcga cctggtgtgc taccgccgtc acggccacaa    2460
cgaagccgac gagccgagcg caacccagcc gctgatgtat cagaaaatca aaaaacatcc    2520
gacaccgcgc aaaatctacg ctgacaagct ggagcaggaa aaagtggcga cgctggaaga    2580
tgccaccgag atggttaacc tgtaccgcga tgcgctggat gctggcgatt gcgtagtggc    2640
agagtggcgt ccgatgaaca tgcactcttt cacctggtcg ccgtacctca accacgaatg    2700
ggacgaagag tacccgaaca agttgagat gaagcgcctg caggagctgg cgaaacgcat    2760
cagcacggtg ccggaagcag ttgaaatgca gtctcgcgtt gccaagattt atggcgatcg    2820
ccaggcgatg gctgccggtg agaaactgtt cgactggggc ggtgcggaaa acctcgctta    2880
cgccacgctg gttgatgaag gcattccggt tcgcctgtcg ggtgaggact ccggtcgcgg    2940
taccttcttc caccgccacg cggtgatcca caaccagtct aacggttcca cttacacgcc    3000
gctgcaacat atccataacg ggcagggcgc gttccgtgtc tgggactccg tactgtctga    3060
agaagcagtg ctggcgtttg aatatggtta tgccaccgca gaaccacgca ctctgaccat    3120
ctgggaagcg cagttcggtg acttcgccaa cggtgcgcag gtggttatcg accagttcat    3180
ctcctctggc gaacagaaat ggggccggat gtgtggtctg gtgatgttgc tgccgcacgg    3240
ttacgaaggc caggggccgg agcactcctc cgcgcgtctg aacgttatc tgcaactttg    3300 tgctgagcaa acatgcagg tttgcgtacc gtctaccccg gcacaggttt accacatgct    3360
gcgtcgtcag gcgctgcgcg ggatgcgtcg tccgctggtc gtgatgtcgc cgaaatccct    3420
gctgcgtcat ccgctggcgg tttccagcct cgaagaactg gcgaacggca ccttcctgcc    3480
agccatcggt gaaatcgacg agcttgatcc gaagggcgtg aagcgcgtag tgatgtgttc    3540
tggtaaggtt tattacgacc tgctggaaca gcgtcgtaag aacaatcaac acgatgtcgc    3600
cattgtgcgt atcgagcaac tctacccgtt cccgcataaa gcgatgcagg aagtgttgca    3660
gcagtttgct cacgtcaagg attttgtctg gtgccaggaa gagccgctca accagggcgc    3720
atggtactgc agccagcatc atttccgtga agtgattccg tttggggctt ctctgcgtta    3780
tgcaggccgc ccggcctccg cctctccggc ggtagggtat atgtccgttc accagaaaca    3840
gcaacaagat ctggttaatg acgcgctgaa cgtcgaataa ataaaggata cacaatgagt    3900
agcgtagata ttctggtccc tgacctgcct gaatccgtag ccgatgccac cgtcgcaacc    3960
tggcataaaa aacccggcga cgcagtcgta cgtgatgaag tgctggtaga atcgaaaact    4020
gacaaagtgg tactggaagt accggcatca gcagacggca ttctggatgc ggttctggaa    4080
gatgaaggta caacggtaac gtctcgtcag atccttggtc gcctgcgtga aggcaacagc    4140
gccggtaaag aaaccagcgc caaatctgaa gagaaagcgt ccactccggc gcaacgccag    4200
caggcgtctc tggaagagca aaacaacgat gcgttaagcc cggcgatccg tcgcctgctg    4260
gctgaacaca atctcgacgc cagcgccatt aaaggcaccg tgtgggtgg tcgtctgact    4320 cgtgaagatg tggaaaaaca tctggcgaaa gccccggcga aagagtctgc tccggcagcg    4380
gctgctccgg cggcgcaacc ggctctggct gcacgtagtg aaaaacgtgt cccgatgact    4440
cgcctgcgta aacgtgtggc agagcgtctg ctggaagcga aaaactccac cgccatgctg    4500
accacgttca acgaagtcaa catgaagccg attatggatc tgcgtaagca gtacggtgaa    4560
```

```
gcgtttgaaa aacgccacgg catccgtctg ggctttatgt ccttctacgt gaaagcggtg    4620
gttgaagccc tgaaacgtta cccggaagtg aacgcttcta tcgacggcga tgacgtggtt    4680
taccacaact atttcgacgt cagcatggcg gtttctacgc cgcgcggcct ggtgacgccg    4740
gttctgcgtg atgtcgatac cctcggcatg gcagacatcg agaagaaaat caaagagctg    4800
gcagtcaaag gccgtgacgg caagctgacc gttgaagatc tgaccggtgg taacttcacc    4860
atcaccaacg gtggtgtgtt cggttccctg atgtctacgc cgatcatcaa cccgccgcag    4920
agcgcaattc tgggtatgca cgctatcaaa gatcgtccga tggcggtgaa tggtcaggtt    4980
gagatcctgc cgatgatgta cctggcgctg tcctacgatc accgtctgat cgatggtcgc    5040
gaatccgtgg gcttcctggt aacgatcaaa gagttgctgg aagatccgac gcgtctgctg    5100
ctggacgtgt agtagtttaa gtttcacctg cactgtagac cggataaggc attatcgcct    5160
tctccggcaa ttgaagcctg atgcgacgct gacgcgtctt atcaggccta cgggaccacc    5220
aatgtaggtc ggataaggcg caagcgccgc atccgacaag cgatgcctga tgtgacgttt    5280
aacgtgtctt atcaggccta cgggtgaccg acaatgcccg gaagcgatac gaaatattcg    5340
gtctacggtt taaagataa cgattactga aggatggaca gaacacatga acttacatga    5400
atatcaggca aaacaacttt tgcccgcta tggcttacca gcaccggtgg ttatgcctg    5460 tactactccg cgcgaagcag aagaagccgc ttcaaaaatc ggtgccggtc cgtgggtagt    5520
gaaatgtcag gttcacgctg gtggccgcgg taaagcgggc ggtgtgaaag ttgtaaacag    5580
caaagaggac atccgtgctt ttgcagaaaa ctggctgggc aagcgtctgg taacgtatca    5640
aacagatgcc aatggccaac cggttaacca gattctggtt gaagcagcga ccgatatcgc    5700
taaagagctg tatctcggtg ccgttgttga ccgtagttcc cgtcgtgtgg tctttatggc    5760
ctccaccgaa ggcggcgtgg aaatcgaaaa agtggcggaa gaaactccgc acctgatcca    5820
taaagttgcg cttgatccgc tgactggccc gatgccgtat cagggacgcg agctggcgtt    5880
caaactgggt ctggaaggta aactggttca gcagttcacc aaaatcttca tgggcctggc    5940
gaccattttc ctggagcgcg acctggcgtt gatcgaaatc aacccgctgg tcatcaccaa    6000
acagggcgat ctgatttgcc tcgacggcaa actgggcgct gacggcaacg cactgttccg    6060
ccagcctgat ctgcgcgaaa tgcgtgacca gtcgcaggaa gatccgcgtg aagcacaggc    6120
tgcacagtgg gaactgaact acgttgcgct ggacggtaac atcggttgta tggttaacgg    6180
cgcaggtctg gcgatgggta cgatggacat cgttaaactg cacggcggcg aaccggctaa    6240
cttccttgac gttggcggcg gcgcaaccaa agaacgtgta accgaagcgt tcaaaatcat    6300
cctctctgac gacaaagtga agccgttctc ggttaacatc ttcggcggta tcgttcgttg    6360
cgacctgatc gctgacggta tcatcggcgc ggtagcagaa gtgggtgtta acgtaccggt    6420
cgtggtacgt ctggaaggta acaacgccga actcggcgcg aagaaactgg ctgacagcgg    6480
cctgaatatt attgcagcaa aaggtctgac ggatgcagct cagcaggttg ttgccgcagt    6540 ggagggaaa taatgtccat tttaatcgat aaaaacacca aggttatctg ccagggcttt    6600
accggtagcc aggggacttt ccactcagaa caggccattg catacggcac taaaatggtt    6660
ggcggcgtaa ccccaggtaa aggcggcacc acccacctcg gcctgccggt gttcaacacc    6720
gtgcgtgaag ccgttgctgc cactggcgct accgcttctg ttatctacgt accagcaccg    6780
ttctgcaaag actccattct ggaagccatc gacgcaggca tcaaactgat tatcaccatc    6840
actgaaggca tcccgacgct ggatatgctg accgtgaaag tgaagctgga tgaagcaggc    6900
gttcgtatga tcggcccgaa ctgcccaggc gttatcactc cgggtgaatg caaaatcggt    6960
```

```
atccagcctg gtcacattca caaaccgggt aaagtgggta tcgtttcccg ttccggtaca   7020
ctgacctatg aagcggttaa acagaccacg gattacggtt tcggtcagtc gacctgtgtc   7080
ggtatcggcg gtgacccgat cccgggctct aactttatcg acattctcga aatgttcgaa   7140
aaagatccgc agaccgaagc gatcgtgatg atcggtgaga tcggcggtag cgctgaagaa   7200
gaagcagctg cgtacatcaa agagcacgtt accaagccag ttgtgggtta tcgcgctggt   7260
gtgactgcgc cgaaaggcaa acgtatgggc cacgcgggtg ccatcattgc cggtgggaaa   7320
gggactgcgg atgagaaatt cgctgctctg gaagccgcag gcgtgaaaac cgttcgcagc   7380
ctggcggata tcggtgaagc actgaaaact gttctgaaat aaaggtccag gcatcaaata   7440
aaacgaaagg ctcagtcgaa agactgggcc tttcgtttta tctgttgttt gtcggtgaac   7500
gctctctact agagtcacac tggctcacct tcgggtgggc ctttctgcgt ttatatcccg   7560
tcaagtcagc gtaatgctct gccagtgtta caaccaatta accaattctg attagaaaaa   7620
ctcatcgagc atcaaatgaa actgcaattt attcatatca ggattatcaa taccatattt   7680
ttgaaaaagc cgtttctgta atgaaggaga aaactcaccg aggcagttcc ataggatggc   7740
aagatcctgg tatcggtctg cgattccgac tcgtccaaca tcaatacaac ctattaattt   7800
cccctcgtca aaaataaggt tatcaagtga gaaatcacca tgagtgacga ctgaatccgg   7860
tgagaatggc aaaagcttat gcatttcttt ccagacttgt tcaacaggcc agccattacg   7920
ctcgtcatca aaatcactcg catcaaccaa accgttattc attcgtgatt gcgcctgagc   7980
gagacgaaat acgcgatcgc tgttaaaagg acaattacaa acaggaatcg aatgcaaccg   8040
gcgcaggaac actgccagcg catcaacaat attttcacct gaatcaggat attcttctaa   8100
tacctggaat gctgttttcc cggggatcgc agtggtgagt aaccatgcat catcaggagt   8160
acggataaaa tgcttgatgg tcggaagagg cataaattcc gtcagccagt ttagtctgac   8220
catctcatct gtaacatcat tggcaacgct acctttgcca tgtttcagaa acaactctgg   8280
cgcatcgggc ttcccataca atcgatagat tgtcgcacct gattgcccga cattatcgcg   8340
agcccattta tacccatata aatcagcatc catgttggaa tttaatcgcg gcctggagca   8400
agacgtttcc cgttgaatat ggctcataac accccttgta ttactgttta tgtaagcaga   8460
cagtttt att gttcatgatg atatattttt atcttgtgca atgtaacatc agagattttg   8520
agacacaacg tggctttgtt gaataaatcg aacttttgct gagttgaagg atcagctcga   8580
gtgccacctg acgtctaaga aaccattatt atcatgacat taacctataa aaataggcgt   8640
atcacgaggc agaatttcag ataaaaaaaa tccttagctt tcgctaagga tgatttctgg   8700
aattcgcggc cgcttctaga gactagtgga agacatcgct ggaaagtgaa acgtgatttc   8760
atgcgtcatt ttgaacattt tgtaaatctt atttaataat gtgtgcggca attcacattt   8820
aatttatgaa tgttttctta acatcgcggc aactcaagaa acggcaggtt cggatcttag   8880
ctactagaga aagaggagaa atactagatg cgtaaaggcg aagagctgtt cactggtgtc   8940
gtccctattc tggtggaact ggatggtgat gtcaacggtc ataagttttc cgtgcgtggc   9000
gagggtgaag gtgacgcaac taatggtaaa ctgacgctga agttcatctg tactactggt   9060
aaactgccgg ttccttggcc gactctggta acgacgctga cttatggtgt tcagtgcttt   9120
gctcgttatc cggaccatat gaagcagcat gacttcttca gtccgccat gccggaaggc   9180
tatgtgcagg aacgcacgat ttcctttaag gatgacggca cgtacaaaac gcgtgcggaa   9240
gtgaaatttg aaggcgatac cctggtaaac cgcattgagc tgaaaggcat tgactttaaa   9300
gaggacggca atatcctggg ccataagctg gaatacaatt ttaacagcca caatgtttac   9360
```

-continued

| | |
|---|---|
| atcaccgccg ataaacaaaa aaatggcatt aaagcgaatt ttaaaattcg ccacaacgtg | 9420 |
| gaggatggca gcgtgcagct ggctgatcac taccagcaaa acactccaat cggtgatggt | 9480 |
| cctgttctgc tgccagacaa tcactatctg agcacgcaaa gcgttctgtc taaagatccg | 9540 |
| aacgagaaac gcgatcatat ggttctgctg gagttcgtaa ccgcagcggg catcacgcat | 9600 |
| ggtatggatg aactgtacaa atgaccaggc atcaaataaa acgaaaggct cagtcgaaag | 9660 |
| actgggcctt tcgttttatc tgttgtttgt cggtgaacgc tctctactag agtcacactg | 9720 |
| gctcaccttc gggtgggcct ttctgcgttt atacgtgcca tgtcttctac tagtagcggc | 9780 |
| cgctgcagtc cggcaaaaaa gggcaaggtg tcaccaccct gccctttttc tttaaaaccg | 9840 |
| aaaagattac ttcgcgttat gcaggcttcc tcgctcactg actcgctgcg ctcggtcgtt | 9900 |
| cggctgcggc gagcggtatc agctcactca aaggcggtaa tacggttatc cacagaatca | 9960 |
| ggggataacg caggaaagaa catgtgagca aaaggccagc aaaaggccag gaaccgtaaa | 10020 |
| aaggc | 10025 |

<210> SEQ ID NO 10
<211> LENGTH: 5088
<212> TYPE: DNA
<213> ORGANISM: Escherichia coli

<400> SEQUENCE: 10

| | |
|---|---|
| ggatggacag aacacatgaa cttacatgaa tatcaggcaa acaactttt tgcccgctat | 60 |
| ggcttaccag caccggtggg ttatgcctgt actactccgc gcgaagcaga agaagccgct | 120 |
| tcaaaaatcg gtgccggtcc gtgggtagtg aaatgtcagg ttcacgctgg tggccgcggt | 180 |
| aaagcgggcg gtgtgaaagt tgtaaacagc aaagaggaca tccgtgcttt tgcagaaaac | 240 |
| tggctgggca gcgtctggt aacgtatcaa acagatgcca atggccaacc ggttaaccag | 300 |
| attctggttg aagcagcgac cgatatcgct aaagagctgt atctcggtgc cgttgttgac | 360 |
| cgtagttccc gtcgtgtggt ctttatggcc tccaccgaag cggcgtgga atcgaaaaa | 420 |
| gtggcggaag aaactccgca cctgatccat aaagttgcgc ttgatccgct gactggcccg | 480 |
| atgccgtatc agggacgcga gctggcgttc aaactgggtc tggaaggtaa actggttcag | 540 |
| cagttcacca aaatcttcat gggcctggcg accatttttcc tggagcgcga cctggcgttg | 600 |
| atcgaaatca cccgctggt catcaccaaa cagggcgatc tgatttgcct cgacggcaaa | 660 |
| ctgggcgctg acggcaacgc actgttccgc cagcctgatc tgcgcgaaat gcgtgaccag | 720 |
| tcgcaggaag atccgcgtga agcacaggct gcacagtggg aactgaacta cgttgcgctg | 780 |
| gacggtaaca tcggttgtat ggttaacggc gcaggtctgg cgatgggtac gatggacatc | 840 |
| gttaaactgc acggcggcga accggctaac ttccttgacg ttggcggcgg cgcaaccaaa | 900 |
| gaacgtgtaa ccgaagcgtt caaaatcatc ctctctgacg acaaagtgaa agccgttctg | 960 |
| gttaacatct tcggcggtat cgttcgttgc gacctgatcg ctgacggtat catcggcgcg | 1020 |
| gtagcagaag tgggtgttaa cgtaccggtc gtggtacgtc tggaaggtaa caacgccgaa | 1080 |
| ctcggcgcga gaaactggc tgacagcggc ctgaatatta ttgcagcaaa aggtctgacg | 1140 |
| gatgcagctc agcaggttgt tgccgcagtg gaggggaaat aaaggtccag gcatcaaata | 1200 |
| aaacgaaagg ctcagtcgaa agactgggcc tttcgtttta tctgttgttt gtcggtgaac | 1260 |
| gctctctact agagtcacac tggctcacct tcgggtgggc ctttctgcgt ttatagctta | 1320 |
| tgtcttctac tagtagcggc cgctgcagtc cggcaaaaaa gggcaaggtg tcaccaccct | 1380 |
| gccctttttc tttaaaaccg aaaagattac ttcgcgttat gcaggcttcc tcgctcactg | 1440 |

```
actcgctgcg ctcggtcgtt cggctgcggc gagcggtatc agctcactca aaggcggtaa    1500
tacggttatc cacagaatca ggggataacg caggaaagaa catgtgagca aaaggccagc    1560
aaaaggccag gaaccgtaaa aaggccgcgt tgctggcgtt tttccacagg ctccgccccc    1620
ctgacgagca tcacaaaaat cgacgctcaa gtcagaggtg gcgaaacccg acaggactat    1680
aaagatacca ggcgtttccc cctggaagct ccctcgtgcg ctctcctgtt ccgaccctgc    1740
cgcttaccgg atacctgtcc gcctttctcc cttcgggaag cgtggcgctt tctcatagct    1800
cacgctgtag gtatctcagt tcggtgtagg tcgttcgctc caagctgggc tgtgtgcacg    1860
aaccccccgt tcagcccgac cgctgcgcct tatccggtaa ctatcgtctt gagtccaacc    1920
cggtaagaca cgacttatcg ccactggcag cagccactgg taacaggatt agcagagcga    1980
ggtatgtagg cggtgctaca gagttcttga agtggtggcc taactacggc tacactagaa    2040
gaacagtatt tggtatctgc gctctgctga agccagttac cttcggaaaa agagttggta    2100
gctcttgatc cggcaaacaa accaccgctg gtagcggtgg ttttttttgtt tgcaagcagc    2160 agattacgcg cagaaaaaaa ggatctcaag aagatccttt gatcttttct acggggtctg    2220
acgctcagtg gaacgaaaac tcacgttaag ggattttggt catgagatta tcaaaaagga    2280
tcttcaccta gatcctttta aattaaaaat gaagttttaa atcaatctaa agtatatatg    2340
agtaaacttg gtctgacagc tcgagtcccg tcaagtcagc gtaatgctct gccagtgtta    2400
caaccaatta accaattctg attagaaaaa ctcatcgagc atcaaatgaa actgcaattt    2460
attcatatca ggattatcaa taccatattt ttgaaaaagc cgtttctgta atgaaggaga    2520
aaactcaccg aggcagttcc ataggatggc aagatcctgg tatcggtctg cgattccgac    2580
tcgtccaaca tcaatacaac ctattaattt cccctcgtca aaataaggt tatcaagtga    2640 gaaatcacca tgagtgacga ctgaatccgg tgagaatggc aaaagcttat gcatttcttt    2700
ccagacttgt tcaacaggcc agccattacg ctcgtcatca aaatcactcg catcaaccaa    2760
accgttattc attcgtgatt gcgcctgagc gagacgaaat acgcgatcgc tgttaaaagg    2820
acaattacaa acaggaatcg aatgcaaccg gcgcaggaac actgccagcg catcaacaat    2880
attttcacct gaatcaggat attcttctaa tacctggaat gctgttttcc cggggatcgc    2940
agtggtgagt aaccatgcat catcaggagt acggataaaa tgcttgatgg tcggaagagg    3000
cataaattcc gtcagccagt ttagtctgac catctcatct gtaacatcat tggcaacgct    3060
acctttgcca tgtttcagaa acaactctgg cgcatcgggc ttcccataca atcgatagat    3120
tgtcgcacct gattgcccga cattatcgcg agcccattta cccatata aatcagcatc    3180 catgttggaa tttaatcgcg gcctggagca agacgtttcc cgttgaatat ggctcataac    3240
accccttgta ttactgttta tgtaagcaga cagttttatt gttcatgatg atatattttt    3300
atcttgtgca atgtaacatc agagattttg agacacaacg tggctttgtt gaataaatcg    3360
aacttttgct gagttgaagg atcagctcga gtgccacctg acgtctaaga accattatt    3420 atcatgacat taacctataa aaataggcgt atcacgagga gaatttcag ataaaaaaa    3480 tccttagctt tcgctaagga tgatttctgg aattcgcggc cgcttctaga gactagtgga    3540
agacatggag tttacggcta gctcagtcct aggtatagtg ctagctactt gttagaaaag    3600
agaagcacgt aatgagtagc gtagatattc tggtccctga cctgcctgaa tccgtagccg    3660
atgccaccgt cgcaacctgg cataaaaaac ccggcgacgc agtcgtacgt gatgaagtgc    3720
tggtagaaat cgaaactgac aaagtggtac tggaagtacc ggcatcagca gacggcattc    3780
tggatgcggt tctggaagat gaaggtacaa cggtaacgtc tcgtcagatc cttggtcgcc    3840
```

```
tgcgtgaagg caacagcgcc ggtaaagaaa ccagcgccaa atctgaagag aaagcgtcca    3900
ctccggcgca acgccagcag gcgtctctgg aagagcaaaa caacgatgcg ttaagcccgg    3960
cgatccgtcg cctgctggct gaacacaatc tcgacgccag cgccattaaa ggcaccggtg    4020
tgggtggtcg tctgactcgt gaagatgtgg aaaaacatct ggcgaaagcc ccggcgaaag    4080
agtctgctcc ggcagcggct gctccggcgg cgcaaccggc tctggctgca cgtagtgaaa    4140
aacgtgtccc gatgactcgc ctgcgtaagc gtgtggcaga gcgtctgctg gaagcgaaaa    4200
actccaccgc catgctgacc acgttcaacg aagtcaacat gaagccgatt atggatctgc    4260
gtaagcagta cggtgaagcg tttgaaaaac gccacggcat ccgtctgggc tttatgtcct    4320
tctacgtgaa agcggtggtt gaagccctga aacgttaccc ggaagtgaac gcttctatcg    4380
acggcgatga cgtggtttac cacaactatt tcgacgtcag catggcggtt tctacgccgc    4440
gcggcctggt gacgccggtt ctgcgtgatg tcgataccct cggcatggca gacatcgaga    4500
agaaaatcaa agagctggca gtcaaaggcc gtgacggcaa gctgaccgtt gaagatctga    4560
ccggtggtaa cttcaccatc accaacggtg gtgtgttcgg ttccctgatg tctacgccga    4620
tcatcaaccc gccgcagagc gcaattctgg gtatgcacgc tatcaaagat cgtccgatgg    4680
cggtgaatgg tcaggttgag atcctgccga tgatgtacct ggcgctgtcc tacgatcacc    4740
gtctgatcga tggtcgcgaa tccgtgggct tcctggtaac gatcaaagag ttgctggaag    4800
atccgacgcg tctgctgctg gacgtgtagt agtttaagtt tcacctgcac tgtagaccgg    4860
ataaggcatt atcgccttct ccggcaattg aagcctgatg cgacgctgac gcgtcttatc    4920
aggcctacgg gaccaccaat gtaggtcgga taaggcgcaa gcgccgcatc cgacaagcga    4980
tgcctgatgt gacgtttaac gtgtcttatc aggcctacgg gtgaccgaca atgcccggaa    5040
gcgatacgaa atattcggtc tacggtttaa aagataacga ttactgaa                 5088
```

UNITED STATES PATENT AND TRADEMARK OFFICE
CERTIFICATE OF CORRECTION

PATENT NO. : 11,421,239 B2  
APPLICATION NO. : 16/036261  
DATED : August 23, 2022  
INVENTOR(S) : Matthew de la Pena Mattozzi et al.

Page 1 of 1

It is certified that error appears in the above-identified patent and that said Letters Patent is hereby corrected as shown below:

On the Title Page

Item (72) Inventors Should read: Matthew de la Pena Mattozzi, Boston, MA (US); Daniel Kim, Carlisle, MA (US); Sonya Clarkson, Beverly, MA (US)

Signed and Sealed this  
Eighth Day of November, 2022

Katherine Kelly Vidal  
*Director of the United States Patent and Trademark Office*